US009043217B2

(12) United States Patent
Cashman et al.

(10) Patent No.: US 9,043,217 B2
(45) Date of Patent: May 26, 2015

(54) MEDICAL KIOSK AND METHOD OF USE

(71) Applicants: Steve Cashman, Powell, OH (US); John W. Spirk, Gates Mills, OH (US); Jason G. Tilk, Cleveland Heights, OH (US); John R. Nottingham, Bratenahl, OH (US); Jeffrey Kalman, Cleveland Heights, OH (US)

(72) Inventors: Steve Cashman, Powell, OH (US); John W. Spirk, Gates Mills, OH (US); Jason G. Tilk, Cleveland Heights, OH (US); John R. Nottingham, Bratenahl, OH (US); Jeffrey Kalman, Cleveland Heights, OH (US)

(73) Assignee: HealthSpot Inc., Dublin, OH (US)

( * ) Notice: Subject to any disclaimer, the term of this patent is extended or adjusted under 35 U.S.C. 154(b) by 215 days.

(21) Appl. No.: 13/760,345

(22) Filed: Feb. 6, 2013

(65) Prior Publication Data
US 2013/0173287 A1    Jul. 4, 2013

Related U.S. Application Data

(63) Continuation-in-part of application No. 13/314,473, filed on Dec. 8, 2011, now Pat. No. 8,996,392, and a continuation-in-part of application No. 29/403,857, filed on Oct. 12, 2011, now Pat. No. Des. 694,909.

(60) Provisional application No. 61/469,851, filed on Mar. 31, 2011, provisional application No. 61/541,719,
(Continued)

(51) Int. Cl.
*G06Q 50/00* (2012.01)
*G06F 19/00* (2011.01)
*G06Q 50/22* (2012.01)
*E04H 3/08* (2006.01)
*G06Q 10/10* (2012.01)
*H04N 7/14* (2006.01)
*E04H 1/12* (2006.01)

(52) U.S. Cl.
CPC ............... *G06F 19/30* (2013.01); *G06Q 50/22* (2013.01); *E04H 3/08* (2013.01); *G06F 19/3418* (2013.01); *G06Q 10/10* (2013.01); *H04N 7/141* (2013.01); *E04H 1/1222* (2013.01)

(58) Field of Classification Search
USPC ............ 705/2; 600/300; 340/825.31; 378/62
See application file for complete search history.

(56) References Cited

U.S. PATENT DOCUMENTS

| 4,884,514 | A | 12/1989 | Shockey et al. |
| 5,036,779 | A | 8/1991 | Capraro |
| D334,985 | S | 4/1993 | D'Agostino et al. |
| D344,140 | S | 2/1994 | Webster |
| 5,393,964 | A | 2/1995 | Hamilton et al. |
| 5,441,047 | A | 8/1995 | David et al. |
| 5,544,649 | A | 8/1996 | David et al. |
| 5,558,638 | A | 9/1996 | Evers et al. |

(Continued)

OTHER PUBLICATIONS

U.S. Searching Authority, International Search Report and Written Opinion, dated Apr. 19, 2013, for related application PCT/US13/24911.

*Primary Examiner* — John Pauls
(74) *Attorney, Agent, or Firm* — Fay Sharpe LLP

(57) ABSTRACT

A medical kiosk designed to provide tele-med services, check-in services, and/or prescription services for a user. The medical kiosk can include a user video conferencing system that is designed to enable the user to have a real-time or near real-time tele-conference with a medical provider located remotely from the medical kiosk.

22 Claims, 13 Drawing Sheets

Related U.S. Application Data filed on Sep. 30, 2011, provisional application No. 61/755,662, filed on Jan. 23, 2013, provisional application No. 61/596,306, filed on Feb. 8, 2012, provisional application No. 61/596,304, filed on Feb. 8, 2012, provisional application No. 61/596,203, filed on Feb. 8, 2012, provisional application No. 61/596,298, filed on Feb. 8, 2012, provisional application No. 61/596,294, filed on Feb. 8, 2012, provisional application No. 61/596,290, filed on Feb. 8, 2012, provisional application No. 61/596,288, filed on Feb. 8, 2012, provisional application No. 61/595,919, filed on Feb. 7, 2012, provisional application No. 61/595,913, filed on Feb. 7, 2012, provisional application No. 61/595,886, filed on Feb. 7, 2012, provisional application No. 61/595,879, filed on Feb. 7, 2012, provisional application No. 61/595,876, filed on Feb. 7, 2012, provisional application No. 61/595,871, filed on Feb. 7, 2012, provisional application No. 61/595,863, filed on Feb. 7, 2012.

(56) References Cited

U.S. PATENT DOCUMENTS

| | | | |
|---|---|---|---|
| 5,619,991 A | | 4/1997 | Sloane |
| 5,646,605 A * | | 7/1997 | Leonaggeo et al. ......... 340/5.64 |
| 5,660,176 A | | 8/1997 | Iliff |
| 5,727,353 A | | 3/1998 | Getz et al. |
| 5,801,755 A | | 9/1998 | Echerer |
| 5,810,747 A | | 9/1998 | Brudny et al. |
| 5,868,669 A | | 2/1999 | Iliff |
| 5,897,493 A | | 4/1999 | Brown |
| 5,910,107 A | | 6/1999 | Iliff |
| 5,987,519 A | | 11/1999 | Peifer et al. |
| 5,997,476 A | | 12/1999 | Brown |
| 6,007,459 A | | 12/1999 | Burgess |
| 6,022,315 A | | 2/2000 | Iliff |
| 6,046,761 A | | 4/2000 | Echerer |
| 6,071,236 A | | 6/2000 | Iliff |
| 6,101,478 A | | 8/2000 | Brown |
| 6,113,540 A | | 9/2000 | Iliff |
| 6,205,716 B1 | | 3/2001 | Peltz |
| 6,206,829 B1 | | 3/2001 | Iliff |
| 6,224,548 B1 | | 5/2001 | Gopinathan et al. |
| 6,248,064 B1 | | 6/2001 | Gopinathan et al. |
| 6,248,065 B1 | | 6/2001 | Brown |
| 6,270,455 B1 | | 8/2001 | Brown |
| 6,295,767 B1 | | 10/2001 | Barnhill et al. |
| 6,302,844 B1 | | 10/2001 | Walker et al. |
| 6,368,273 B1 | | 4/2002 | Brown |
| 6,369,847 B1 | | 4/2002 | James et al. |
| 6,381,577 B1 | | 4/2002 | Brown |
| 6,403,897 B1 | | 6/2002 | Bluth et al. |
| 6,428,124 B1 | | 8/2002 | Bluth et al. |
| 6,449,001 B1 | | 9/2002 | Levy et al. |
| 6,511,435 B1 | | 1/2003 | Bluth et al. |
| 6,540,673 B2 | | 4/2003 | Gopinathan et al. |
| 6,594,607 B2 | | 7/2003 | Lavery |
| 6,595,918 B2 | | 7/2003 | Gopinathan et al. |
| 6,638,218 B2 | | 10/2003 | Bulat |
| 6,641,532 B2 | | 11/2003 | Iliff |
| 6,668,375 B1 | | 12/2003 | Leovac |
| 6,692,436 B1 | | 2/2004 | Bluth et al. |
| 6,725,209 B1 | | 4/2004 | Iliff |
| 6,731,324 B2 | | 5/2004 | Levy |
| 6,748,353 B1 | | 6/2004 | Iliff |
| 6,790,178 B1 | | 9/2004 | Mault et al. |
| 6,850,889 B1 | | 2/2005 | Zayas, Jr. |
| 6,968,375 B1 | | 11/2005 | Brown |
| 7,011,629 B2 | | 3/2006 | Bulat |
| D521,155 S | | 5/2006 | Shipard |
| D526,065 S | | 8/2006 | Shipard |
| 7,112,175 B2 | | 9/2006 | Gopinathan et al. |
| 7,188,151 B2 | | 3/2007 | Kumar et al. |
| 7,223,236 B2 | | 5/2007 | Brown |
| 7,252,636 B2 | | 8/2007 | Brown |
| 7,297,109 B2 | | 11/2007 | Brown |
| 7,297,111 B2 | | 11/2007 | Iliff |
| 7,300,402 B2 | | 11/2007 | Iliff |
| 7,310,668 B2 | | 12/2007 | Brown |
| 7,320,030 B2 | | 1/2008 | Brown |
| D577,127 S | | 9/2008 | Ronco |
| 7,435,222 B2 | | 10/2008 | Gopinathan et al. |
| 7,516,192 B2 | | 4/2009 | Brown |
| 7,533,171 B2 | | 5/2009 | Brown |
| 7,587,469 B2 | | 9/2009 | Brown |
| 7,613,620 B2 | | 11/2009 | Salwan |
| 7,624,028 B1 | | 11/2009 | Brown |
| 7,691,059 B2 | | 4/2010 | Bulat |
| 7,707,270 B2 | | 4/2010 | Brown |
| 7,730,177 B2 | | 6/2010 | Brown |
| 7,734,718 B2 | | 6/2010 | Brown |
| 7,753,845 B2 | | 7/2010 | Gopinathan et al. |
| 7,761,312 B2 | | 7/2010 | Brown |
| 7,818,183 B2 | | 10/2010 | Schoenberg |
| 7,822,625 B2 | | 10/2010 | Brown |
| 7,831,444 B2 | | 11/2010 | Brown |
| 7,860,725 B2 | | 12/2010 | Gopinathan et al. |
| 7,870,249 B2 | | 1/2011 | Brown |
| 7,877,271 B2 | | 1/2011 | Brown |
| 7,904,310 B2 | | 3/2011 | Brown |
| 7,912,733 B2 | | 3/2011 | Clements et al. |
| RE42,288 E | | 4/2011 | Degioanni |
| 7,921,186 B2 | | 4/2011 | Brown |
| D638,551 S | | 5/2011 | Gann |
| 7,941,323 B2 | | 5/2011 | Brown |
| 7,941,326 B2 | | 5/2011 | Brown |
| 7,941,327 B2 | | 5/2011 | Brown |
| 7,949,383 B2 | | 5/2011 | Cable et al. |
| 7,970,620 B2 | | 6/2011 | Brown |
| 7,970,633 B2 | | 6/2011 | Bulat |
| 7,979,284 B2 | | 7/2011 | Brown |
| 7,987,100 B2 | | 7/2011 | Brown |
| 8,005,691 B2 | | 8/2011 | Kumar et al. |
| 8,015,025 B2 | | 9/2011 | Brown |
| 8,015,138 B2 | | 9/2011 | Iliff |
| 8,027,809 B2 | | 9/2011 | Brown |
| 8,078,407 B1 | | 12/2011 | Brown |
| 8,078,431 B2 | | 12/2011 | Brown |
| 8,095,340 B2 | | 1/2012 | Brown |
| 8,096,083 B2 | | 1/2012 | Ma et al. |
| 8,140,663 B2 | | 3/2012 | Brown |
| D664,667 S | | 7/2012 | Krymov et al. |
| 8,260,630 B2 | | 9/2012 | Brown |
| 8,285,560 B2 | | 10/2012 | Gopinathan et al. |
| 8,321,284 B2 | | 11/2012 | Clements et al. |
| 8,337,409 B2 | | 12/2012 | Iliff |
| 2001/0011224 A1 | | 8/2001 | Brown |
| 2003/0028399 A1 | | 2/2003 | Davis et al. |
| 2003/0088441 A1 | | 5/2003 | McNerney |
| 2003/0163351 A1 | | 8/2003 | Brown et al. |
| 2004/0006496 A1 | | 1/2004 | Nickerson |
| 2004/0019259 A1 | | 1/2004 | Brown |
| 2004/0019261 A1 | | 1/2004 | Gopinathan et al. |
| 2004/0019505 A1 | | 1/2004 | Bowman et al. |
| 2004/0107116 A1 | | 6/2004 | Brown |
| 2004/0230458 A1 | | 11/2004 | Takayama et al. |
| 2004/0249778 A1 | | 12/2004 | Iliff |
| 2005/0228883 A1 | | 10/2005 | Brown |
| 2005/0256739 A1 | | 11/2005 | Brown |
| 2006/0010014 A1 | | 1/2006 | Brown |
| 2006/0069753 A1 | | 3/2006 | Hu et al. |
| 2006/0080152 A1 | | 4/2006 | Brown |
| 2006/0189853 A1 | | 8/2006 | Brown |
| 2006/0200319 A1 | | 9/2006 | Brown |
| 2006/0235722 A1 | | 10/2006 | Brown |
| 2006/0241975 A1 | | 10/2006 | Brown |
| 2006/0259201 A1 | | 11/2006 | Brown |
| 2006/0259332 A1 | | 11/2006 | Brown |
| 2006/0271214 A1 | | 11/2006 | Brown |
| 2006/0285660 A1 | | 12/2006 | Brown |
| 2006/0285736 A1 | | 12/2006 | Brown |

Related U.S. Application Data

| | | |
|---|---|---|
| 2006/0287889 A1 | 12/2006 | Brown |
| 2006/0287931 A1 | 12/2006 | Brown |
| 2006/0293572 A1 | 12/2006 | Bulat |
| 2007/0011320 A1 | 1/2007 | Brown |
| 2007/0016445 A1 | 1/2007 | Brown |
| 2007/0021984 A1 | 1/2007 | Brown |
| 2007/0061167 A1 | 3/2007 | Brown |
| 2007/0073113 A1 | 3/2007 | Squilla et al. |
| 2007/0118588 A1 | 5/2007 | Brown |
| 2007/0130287 A1 | 6/2007 | Kumar et al. |
| 2007/0156893 A1 | 7/2007 | Brown |
| 2007/0168242 A1 | 7/2007 | Brown |
| 2007/0168504 A1 | 7/2007 | Brown |
| 2007/0213605 A1 | 9/2007 | Brown |
| 2007/0265869 A1 | 11/2007 | Ryckman et al. |
| 2007/0299321 A1 | 12/2007 | Brown |
| 2008/0051638 A1 | 2/2008 | Iliff |
| 2008/0051640 A1 | 2/2008 | Iliff |
| 2008/0052119 A1 | 2/2008 | Iliff |
| 2008/0052318 A1 | 2/2008 | Iliff |
| 2008/0059247 A1 | 3/2008 | Iliff |
| 2008/0162393 A1 | 7/2008 | Iliff |
| 2009/0083066 A1 | 3/2009 | Bailey et al. |
| 2009/0240115 A1 | 9/2009 | Bluth |
| 2009/0240116 A1 | 9/2009 | Bluth |
| 2009/0240524 A1 | 9/2009 | Bluth |
| 2009/0240527 A1 | 9/2009 | Bluth |
| 2009/0240528 A1 | 9/2009 | Bluth |
| 2009/0240702 A1 | 9/2009 | Bluth |
| 2009/0241177 A1 | 9/2009 | Bluth |
| 2010/0030580 A1 | 2/2010 | Salwan |
| 2010/0146300 A1 | 6/2010 | Brown |
| 2010/0274835 A1 | 10/2010 | Brown |
| 2011/0004487 A1 | 1/2011 | Schoenberg |
| 2011/0009707 A1* | 1/2011 | Kaundinya et al. ........... 600/300 |
| 2011/0106557 A1 | 5/2011 | Gazula |
| 2011/0122995 A1* | 5/2011 | Ferro, Jr. ..................... 378/62 |
| 2011/0161475 A1 | 6/2011 | Raghavendran et al. |
| 2011/0191117 A1 | 8/2011 | Hashim-Waris |
| 2011/0288888 A1 | 11/2011 | Gazula |
| 2012/0004525 A1 | 1/2012 | Brown |
| 2012/0130647 A1 | 5/2012 | Brown |
| 2012/0130739 A1 | 5/2012 | Crane |
| 2012/0179479 A1* | 7/2012 | Waterson et al. ................. 705/2 |
| 2012/0185278 A1 | 7/2012 | Brown |
| 2012/0203466 A1 | 8/2012 | Brown |
| 2012/0253837 A1 | 10/2012 | Cashman |
| 2013/0013333 A1 | 1/2013 | Gopinathan et al. |

* cited by examiner

MEDICAL KIOSK AND METHOD OF USE

The present invention is a continuation-in-part of U.S. Ser. No. 13,314,473 filed Dec. 8, 2011, which in turn claims priority on U.S. patent application Ser. Nos. 61/469,851 file Mar. 31, 2011 and 61/541,719 filed Sep. 30, 2011, which are both incorporated herein by reference.

The present invention is a continuation-in-part of U.S. Ser. No. 13,314,473 filed Dec. 8, 2011, which in turn is a continuation-in-part of U.S. Design patent application Ser. No. 29/403,857 filed Oct. 12, 2011, which are both incorporated herein by reference.

The present invention claims priority on U.S. patent application Ser. Nos. 61/755,662 filed Jan. 23, 2013; 61/596,306 filed Feb. 8, 2012; 61/596,304 filed Feb. 8, 2012; 61/596,302 filed Feb. 8, 2012; 61/596,298 filed Feb. 8, 2012; 61/596,294 filed Feb. 8, 2012; 61/596,290 filed Feb. 8, 2012; 61/596,288 filed Feb. 8, 2012; 61/595,919 filed Feb. 7, 2012; 61/595,913 filed Feb. 7, 2012; 61/595,886 filed Feb. 7, 2012; 61/595,879 filed Feb. 7, 2012; 61/595,876 filed Feb. 7, 2012; 61/595,871 file Feb. 7, 2012; 61/595,863 filed Feb. 7, 2012, which are all incorporated herein by reference.

The present invention is directed to medical services, more particularly to a method and device for providing medical services to individuals, even more particularly to a method and device for providing medical services to individuals at locations that traditionally have not provided medical services, and still even more particularly to a medical kiosk and method for using a medical kiosk to providing medical services to individuals at locations that are remote from a medical provider.

BACKGROUND OF THE INVENTION

Medical services are traditionally provided to individuals at a doctor's office or medical facility. Typically, an individual contacts his/her medical provider when the individual requires some type of medical assistance. The medical provider then sets an appointment time and date for the individual to see the medical provider. Many times, the time and date of the appointment are inconvenient for the individual. Furthermore, the individual seeking medical assistance may desire or need more immediate medical assistance and cannot wait for the time and date set by the medical provider. In such situations, the individual goes to the emergency room of a hospital or some type of medical clinic (e.g., Minute Clinic, Take Care Clinic, Urgent Care Clinic, etc.), assuming that such clinics are available or convenient to visit. In other situations, especially in smaller towns and rural areas, a medical facility may be located many miles away thus making a visit to such a facility very inconvenient. As such, many individuals who should seek medical care decide to not seek the advice of medical personnel due to the inconvenience of having to travel large distances to a medical facility.

The costs associated with visiting a medical provider can be costly depending on the type of insurance, if any, the individual carries. When an individual visits the emergency room of a hospital, the medical costs can be substantially higher and insurance coverage may be limited to various types of visits. Insurance coverage and the cost of the visit may also vary at various clinics. In many communities, clinics are not readily available, thus the individual must either visit the medical provider or go to the hospital.

Various pharmacy and drug stores have begun offering medical services on their premises. These locations generally offer flu shots and very basic medical services, and are typically provided by a nurse practitioner, not a doctor. As such, only very limited types of medical services are offered at such locations. Also, these locations are not offered in a private environment. Generally, the services are provided in a side corridor or partitioned location in the facility.

In view of the current state of the medical services, there is a need for providing medical services in a more convenient, desirable, timely and cost effective manner.

SUMMARY OF THE INVENTION

The present invention is directed to a method and apparatus for providing medical services, diagnoses, health, and/or wellness advice to individuals in a convenient, desirable, timely and cost effective manner. The novel medical apparatus of the present invention and the novel method for providing medical services, diagnoses, health advice, and/or wellness advice addresses the current deficiencies that exist for providing medical services to individuals.

In one non-limiting aspect of the invention, there is provided a method and apparatus for providing medical services, diagnoses, health, and/or wellness advice to individuals that includes a remote medical service arrangement wherein a patient can receive various types of medical advice and services remotely from one or more medical providers (e.g., doctor, nurse practitioner, nurse, psychologist, psychiatrist, optometrist, physician assistant, pharmacist, health coach, dietitian, medical assistant, etc.). Traditionally, a patient was required to go to a medical facility (e.g., hospital, medical clinic, doctor's office, etc.) to personally meet with and be diagnosed by the medical provider. The present invention is directed to a method wherein medical services, diagnoses, health advice, and/or wellness advice can be dispensed by a medical provider at a location that is remote from the patient. The present invention can be used to provide services in one or more different medical specialties (e.g., Allergology; Andrology; Anesthesia; Angiology; Athletic training; Aviation medicine; Cardiology; Dentistry; Dermatology; Disaster medicine; Emergency medicine; Endocrinology; Family medicine; Gastroenterology; General practice; Medical genetics; Geriatrics; Gerontology; Gynaecology; Hematology; Hepatology; Immunology; Infectious diseases; Intensive care medicine; Internal medicine; Military medicine; Nephrology; Neurology; Nuclear medicine; Obstetrics; Oncology; Ophthalmology; Oral and maxillofacial surgery; Orthopedics; Otolaryngology; Paleopathology; Palliative medicine; Pathology; Pediatrics; Podiatry; Psychiatric specialties; Psychiatry; Pulmonology; Radiology; Rehabilitation medicine; Rheumatology; Serology; Sexual health; Sleep medicine; Space medicine; Sports medicine; Surgery; Toxicology; Transplantation medicine; Tropical medicine; Urology; Wilderness medical emergencies; and/or Wilderness medicine). The method and device of the present invention can be used to provide initial screening, treatment, and/or follow-up treatment for a patient. The method and device of the present invention can be used in many situations as an alternative for a patient visiting a medical facility or a doctor's office. However, it can be appreciated that the device of the present invention could be located in a lobby or special region of a doctor's office or medical facility. In one non-limiting arrangement of the present invention, there is provided an audio and/or video link between one or more medical providers located at one or more locations (e.g., medical provider's office, medical provider's home, hospital, etc.) and the patient is located at some other location (e.g., shopping mall, shopping center, drug store, grocery store, department store, warehouse store, discount retailer, discount department store, truck trailer, mobile office, mobile home, office space location, etc.) that is remote from the one or more medical providers. The novel method of the present invention for providing medical services, diagnoses, health advice, and/or wellness advice enables a medical provider to provide medical services, diagnoses, health advice, and/or wellness advice to patients without the patient having to physically visit the medical provider and/or having to go to the medical provider's office or place of work. As can be appreciated, the audio and/or video link that is used by the medical provider can enable the medical provider to provide medical services, diagnoses, health advice, and/or wellness advice at a single remote location or a plurality of remote locations. When the audio and/or video link enables the medical provider to provide medical services, diagnoses, health advice, and/or wellness advice to a plurality of remote locations, a single medical provider and/or a plurality of medical providers can be used to provide medical services, diagnoses, health advice, and/or wellness advice to patients that are located at a variety of different remote locations. When a plurality of medical providers is used, the medical providers can be located at the same or different locations. As can be appreciated, the novel method for providing medical services allows for more flexibility for a patient to obtain medical services, diagnoses, health advice, and/or wellness advice. The site at which the patient obtains the medical services, diagnoses, health advice, and/or wellness advice via the method and device of the present invention can be located in a) non-traditional locations that are more convenient to a patient (e.g., shopping mall, public park, department store, retail store, grocery store, museum, office building, business office, business facility, big box stores, government base or facility, drug stores, boat, airplane, train, etc.), and/or b) traditional locations (e.g., doctor's office, hospital, urgent care facility, etc.) so as to provide easier and/or more convenient access to such medical services, diagnoses, health advice, and/or wellness advice. The geographic location for the device of the present invention can be in a single neighborhood, multiple neighborhoods, a single town or city, multiple towns or cities, a single state or province, multiple states or provinces, a single country, or multiple countries. The novel method can also be used to provide medical services, diagnoses, health advice, and/or wellness advice at standard times (e.g., 9 am-5 pm Monday through Friday, etc.) and/or non-standard times (e.g., early morning hours, evening hours, weekend hours, holiday hours, etc.) to enable a patient to obtain medical services, diagnoses, health advice, and/or wellness advice that are more convenient and timely to the patient.

In another and/or alternative non-limiting aspect of the invention, the novel method and apparatus for providing medical services, diagnoses, health, and/or wellness advice to individuals can be used to provide a variety of different medical services, diagnoses, health advice, and/or wellness advice. Non-limiting examples of such medical services, diagnoses, health advise, wellness advise and/or medical conditions that can be identified, treated and/or addressed include, but are not limited to Acid Reflux; Hypertension Management; Allergies; Athlete's Foot; Acne; Mental Health Counseling; Wellness Counseling; Asthma; Cold Sores; Vaccinations; Arthritis; Bronchitis; Impetigo; Wellness Coaching; Weight Loss; Eating Disorders; Bladder Infections; Insect Stings; Allergic Reactions; Rashes; Hemorrhoids; Minor Burns; Health Risk Management; Migraine Headaches; Common Colds; Virus Infections; Bacterial Infections; Minor Skin Infections; Chronic Disease Management; Coughs; Poison Oak/Ivy; Diarrhea; Rashes; Diabetes; Ringworm; Lice; Ear Infections; Sties; Flu; Fever; Gout; Headache (minor); Pink Eye; Sinus Infections; Sore Throat; Ear Infections; Cramps; STDs; Strep Throat; Throat Infections; Feeding Problems For Newborns; Vomiting; Teething; Gastrointestinal Problems; Anxiety; Depression, Formula Advice For Newborns; Concussion; Head Injuries; Bone Fractures; Sprains; Hair Loss; Alopecia; Eye Infections; Urinary Tract Infections; Constipation; Appendicitis; Pharyngitis; Medication Therapy Management; Acid Reflux Disease; Acne; Alcohol abuse; Allergies; Antisocial Personality Disorder; Attention Deficit Disorder; Altitude Sickness; Alzheimer's Disease; Andropause; Anger management; Anorexia Nervosa; Arthritis; Aspergers Syndrome; Asthma; Autism; Back Pain; Bad Breath (Halitosis); Baldness; Bedwetting; Bipolar Disorder; Bladder Cancer; Body Dysmorphic Disorder; Bone Cancer; Brain Cancer; Breast Cancer; Brain Tumors; Brain Injury; Bronchitis; Burns; Bursitis; Cancer; Canker Sores; Carpal Tunnel Syndrome; Celiac Disease; Cervical Cancer; Cholesterol; Chronic Obstructive Pulmonary Disease; Colon Cancer; Congestive Heart Failure; Cradle Cap; Crohn's Disease; Dandruff; Deep Vein Thrombosis; Dehydration; Depression; Diabetes; Diaper Rash; Diarrhea; Disabilities; Diverticulitis; Down Syndrome; Drug Abuse; Smoking Cessation; Dysfunctional Uterine Bleeding; Dyslexia; Ear Infections; Ear Problems; Eating Disorders; Eczema; Endometriosis; Enlarged Prostate; Epilepsy; Erectile Dysfunction; Eye Problems; Fibromyalgia; Fracture; Gallbladder Disease; Gallstones; Generalized Anxiety Disorder; Genital Herpes; Genital Warts; Glomerulonephritis; Gonorrhea; Gout; Gum Diseases; Gynecomastia; Head Lice; Headache; Hearing Loss; Heart Attacks; Heart Disease; Heartburn; Heat Stroke; Heel Pain; Hemorrhage; Hemorrhoids; Hepatitis; Herniated Discs; Hiatal Hernia; HIV/AIDS; Hives; Hyperglycemia; Hyperkalemia; Hypertension; Hyperthyroidism; Hypothyroidism; Infectious Diseases; Infectious Mononucleosis; Influenza; Infertility; Insulin Dependent Diabetes Mellitus; Iron Deficiency Anemia; Irritable Bowel Syndrome; Irritable Male Syndrome; Itching; Joint Pain; Juvenile Diabetesl; Juvenile Rheumatoid Arthritis; Kidney Diseases; Kidney Stones; Leukemia; Liver Cancer; Lung Cancer; Mad Cow Disease; Malaria; Medication Management; Melena; Memory Loss; Menopause; Mesothelioma; Migraine; Miscarriages; Mucus In Stool; Multiple Personality Disorder; Multiple Sclerosis; Muscle Cramps; Muscle Fatigue; Muscle Pain; Nail Biting; Narcissistic Personality Disorder; Neck Pain; Obesity; Obsessive Compulsive Disorder; Osteoarthritis; Osteomyelitis; Osteoporosis; Ovarian Cancer; Ovarian Cyst; Pain; Pain Management; Panic Attack; Parkinson's Disease; Peripheral Artery Disease; Personality Disorders; Pervasive Developmental Disorder; Peyronie's Disease; Phobias; Pink Eye; Polio; Pneumonia; Post Nasal Drip; Post Traumatic Stress Disorder; Premature Baby; Premenstrual Syndrome; Prostate Cancer; Psoriasis; Reactive Attachment Disorder; Renal Failure; Restless Legs Syndrome; Rheumatoid Arthritis; Rheumatic Fever; Ringworm; Rosacea; Rotator Cuff; Scabies; Scars; Sciatica; Schizophrenia; Sexually Transmitted Disease; Sinus Infections; Skin Cancer; Skin Rash; Sleep Apnea; Sleep Disorders; Smallpox; Snoring; Social Anxiety; Staph Infection; Stomach Cancer; Strep Throat; Sudden Infant Death Syndrome; Sunburn; Syphilis; Systemic Lupus Erythematosus; Tennis Elbow; Termination of Pregnancy; Testicular Cancer; Tooth Decay; Tuberculosis; Ulcers; Urinary Tract Infection; Varicose Veins; Vertigo; Warts; Williams Syndrome; Yeast Infection; Yellow Fever, etc. As can be appreciated, other or additional types of medical services and/or health care services can be provided. The medical services and/or health care services that can be provided can include, but are not limited to, 1) providing advice and/or recommendations about a medical condition, 2) diagnosing and/or treating a medical condition, 3) providing referral services for a medical condition, 4) prescribing medicine for a medical condition, 5) periodically monitoring a medical condition, 6) providing follow-up checks for a medical condition, 7) providing routine check-up services, 8) providing advice, counseling, and/or recommendations about medical and/or health matters, 9) providing a course of treatment for a medical condition, 8) providing health counseling, 10) providing health information, 12) providing wellness counseling, and/or 13) providing wellness information. As can be appreciated, other or additional services can be provided to the patient. In essence, any type of medical condition, medical concern, health concern, wellness concern, etc. can be addressed in whole or part by the novel method and apparatus for providing medical services of the present invention. Hereinafter, these services will be collectively referred to as medical services. As can be appreciated, the type of services provided to a patient will depend on the specific medical condition, medical concern or need, wellness concern or need, and/or health concern or need of the patient. In many instances, the medical provider will be able to diagnose, address, advise, consult and/or treat the specific medical condition or need, medical concern or need, wellness concern or need, health concern or need, etc. of the patient. In some instances, the specific medical condition or need, medical concern or need, wellness concern or need, health concern or need, etc. of the patient may be too complicated and/or complex to address via an audio and/or video link, thus the medical provider in such situations may have to refer the patient to a hospital, a doctor's office, counselor, psychiatrist/psychologist, medical specialist, health professional, dietician, rehabilitation facility, or a traditional medical clinic for further counseling, treatment and/or diagnosis, or some other location or professional that can address the patient's needs and/or requirements.

In still another and/or alternative non-limiting aspect of the invention, the novel method and apparatus for providing medical services, diagnoses, health, and/or wellness advice to individuals can include the use of a medical kiosk to enable the patient to conveniently communicate with one or more medical providers. One or more medical kiosks can be used in the present invention. Generally, a plurality of medical kiosks which are located at one or more locations are used in the method of the present invention; however, it can be appreciated that a single medical kiosk can be used in accordance with the present invention. Typically one or more medical providers provide services to one or more medical kiosks. The size, shape, configuration and look of the medical kiosk are non-limiting. In one non-limiting embodiment of the invention, the medical kiosk provides a private or semi-private environment for a patient to communicate with one or more medical providers that are located remotely from the medical kiosk. In one non-limiting arrangement, the medical kiosk includes an enclosure that is designed to enable a patient to enter the enclosure and to communicate with the medical provider in a private or semi-private manner while in the enclosure of the medical kiosk. The size, shape and configuration of the enclosure of the medical kiosk are non-limiting. In another and/or alternative non-limiting arrangement, the medical kiosk includes one or more walls that form all or a portion of the sides of the enclosure of the medical kiosk. The enclosure may include one or more doors or entry points to enable a patient to enter and/or exit the enclosure. In another and/or alternative non-limiting arrangement, the medical kiosk typically includes a floor and/or a ceiling. The ceiling, when included, can include a portion that is partially or fully transparent; however, this is not required. In another and/or alternative non-limiting arrangement, the medical kiosk can have a modular configuration to enable the parts of the medical kiosk to be set up in various configurations to enable the medical kiosk to be used in various types of spaces and/or to be set up in various types of configurations. The medical kiosk can be formed of any number of materials (e.g., plastic, foam, metal, wood, composite materials, fiber board, etc.). The one or more walls of the medical kiosk can be designed to be interchangeable to enable the door, when used, to be positioned on various locations on the medical kiosk; however, this is not required. The medical kiosk can include a floor and/or ceiling to provide for increased privacy for the patient when the patient is inside the room, cavity or enclosure of the medical kiosk; however, this is not required. The medical kiosk can include one or more tables, ledges, benches, and/or seats in the interior and/or exterior of the medical kiosk; however, this is not required. Such table, ledge, bench, and/or seat, when used, can be designed to be connected in multiple locations on the exterior and/or interior of the medical kiosk; however, this is not required. The modular configuration of the medical kiosk can be such that it can be easily assembled and/or disassembled so that the medical kiosk can be easily brought into a location and easily set up, and/or be easily removed from a location; however, this is not required.

In yet another and/or alternative non-limiting aspect of the invention, the novel method and apparatus for providing medical services, diagnoses, health, and/or wellness advice to individuals can include the use of a medical kiosk that includes one or more data input terminals. The one or more data input terminals can be located on one or more locations on the exterior of the medical kiosk; however, this is not required. Alternatively or additionally, the one or more data input terminals can be located on one or more locations in the interior or enclosure of the medical kiosk; however, this is not required. The one or more data input terminals can include a video display to display information regarding identification and/or data entry, a camera and/or video camera used to collect information for identification and/or data entry, a key pad or key board for identification and/or data entry, a touch screen for identification and/or data entry, microphone and voice recognition software for identification and/or data entry, fingerprint scanner for identification and/or data entry, retina scanner for identification and/or data entry, and/or face and/or body scanners for identification and/or data entry. As can be appreciated, other or additional devices can be included on the medical kiosk to display and/or obtain information regarding identification and/or data entry. The medical kiosk can be used by the patient to enter/convey basic information about the patient. Such information includes, but is not limited to, a) patient name, b) patient address, c) patient contact information (e.g., home address, work address, phone number, email address, pager number, work number, etc.), d) patient age, e) patient sex, f) patient height, g) patient weight, h) patient medical history, i) current medicines used by patient, j) reason(s) for visit by patient, k) patient current symptoms, l) patient insurance information, m) patient payment information, n) patient's current doctor, o) guardian or patent information, p) next of kin information, q) desired medical provider for visit, r) allergy information, s) information about a prior visit, t) medical records information, and/or u) pharmacy information. As can be appreciated, other or additional information can be inputted/conveyed by the patient.

In still another and/or alternative non-limiting aspect of the invention, the novel method and apparatus for providing medical services, diagnoses, health, and/or wellness advice to individuals can include a medial kiosk that can be designed to provide information to the patient prior to and/or during the inputting/conveying of information by the patient to the medical kiosk. In one non-limiting embodiment of the invention, the medical kiosk can include audio and/or visual instructions and/or displays used to provide a) information about the medical kiosk, b) how to use the medial kiosk, c) how to properly input/convey information to the medical kiosk, d) provide instructions and/or interactions with the patient during the inputting/conveying of information by the patient to the medical kiosk, e) the wait time for the patient's use of the medical kiosk, f) a list of patient's waiting to use the medical kiosk, g) available medical providers, h) types of medical issues that can be addressed by use of the medical kiosk, i) insurance providers that can be used to partially or fully pay for a visit in the medical kiosk, j) payment options for use of the medical kiosk, k) information regarding when the medical kiosk in the future is available, and/or l) information regarding whether the medical kiosk is in use or is available. In another and/or alternative non-limiting embodiment of the invention, the medical kiosk can include light, sound indicators, and/or digital displays to provide information regarding whether the medical kiosk is in use or is available; however, this is not required. In still another and/or alternative non-limiting embodiment of the invention, the medical kiosk can include a notification system to a patient that the medical kiosk is available or will soon be available; however, this is not required. Such notification can be sent via email, text, phone, pager, internet, digital display, etc. Such notification system can be useful when the medical kiosk is not currently available to the patient. The patient can input the information into the medical kiosk and then go home, run other errands, etc., and then be later notified when the medical kiosk is available or will soon be available. The medical kiosk and/or notification system can also be used to inform the patient when and/or where other medical kiosks are available; however, this is not required. This service, when available, can be used to inform the patient that a nearby medical kiosk has a shorter wait period or is currently available, thus providing the patient with the option of traveling to another available medical kiosk instead of waiting for the current medical kiosk to become available; however, this is not required. This service, when available, can also be used to inform the patient when a prescription is ready for pickup and/or for conveying prescription information to the patient; however, this is not required. This service, when available, can also be used to inform the patient when a follow-up visit is due and/or scheduled; however, this is not required. As can be appreciated, the notification system can be used for other or additional services.

In yet another and/or alternative non-limiting aspect of the invention, the novel method and apparatus for providing medical services, diagnoses, health, and/or wellness advice to individuals can include a scheduling system for use of the medical kiosk. The schedule system allows a patient to schedule an appointment with a medical provider when the patient uses the medical kiosk. The scheduling system can be used to 1) enable a patient to select a particular medical provider, 2) make an appointment on a medical kiosk at a particular time and place, 3) enable a patient to select a medical provider or type of medical provide based on the particular need of the patient (e.g., select a medical provider that specializes in dermatology to address a rash issue on the patient, select a medical provider that specializes in orthopedics to address a sports injury to the knee, etc.), 4) locate available locations of medical kiosks, 5) enable a patient to enter basic information about the patient, 6) check a past, current or future appointment of the patient regarding use of the medical kiosk, 7) enter a partial or fully payment for use of the medical kiosk, 8) enter medical insurance information, etc. The scheduling system can be designed to be accessed by a patient on a data entry device on a medical kiosk, via a computer or phone or smart device, and/or by phone. The scheduling system can optionally be designed to enable a patient to request assistance if there a question regarding the use of the scheduling system.

In still yet another and/or alternative non-limiting aspect of the invention, the novel method and apparatus for providing medical services, diagnoses, health, and/or wellness advice to individuals can include one of more software applications (e.g., patent registration application, attendant application, patient appointment or registration application, medical provider application, administrator application, patient portal, provider portal, etc.). For example, the Patient Appointment or Registration Application can include the screens the patient navigates through during the patient registration process; however, this is not required. These screens can optionally appear on the registration station of the exterior of the medical kiosk. The Attendant Application can include screens that the medical attendant, when used, navigates through during the patient appointment; however, this is not required. These screens can optionally appear on a laptop, computer screen, tablet, smart phone, etc. located with the medical attendant and/or at or near the attendant desk on the exterior of the medical kiosk; however, this is not required. The Patient Appointment or Registration Application can include screens the patient navigates through during the patient consultation; however, this is not required. These screens can optionally appear on the medical provider screen and/or patient screen in the interior of the medical kiosk. The Provider Application can include the screens the medical provider navigates through during the patient appointment; however, this is not required. These screens can optionally appear on the medical provider's computer, laptop, tablet, smart phone, etc. at his/her remote location. As can be appreciated, other or additional software and/or hardware application can be used with the medical kiosk of the present invention. The Patient Appointment or Registration Application can allow the patient to select a language to be displayed (e.g., English, Spanish, German, French, Chinese, Japanese, etc.); however, this is not required.

In another and/or alternative non-limiting aspect of the invention, the novel method and apparatus for providing medical services, diagnoses, health, and/or wellness advice to individuals can include the use of a Patient Appointment or Registration Application. The Patient Appointment or Registration Application can include one or more navigational buttons (e.g., back, next, cancel, request assistance, etc.) for use by the patient during the registration process; however, this is not required). For example, the Back button can be designed to allow the patient to return to the previous screen, the Next button can be designed to allow the patient to proceed to the next screen, the Cancel button can be designed to allow the patient to cancel a process and return to the beginning of the process (e.g., patient receives a pop-up box asking them if they are sure they want to cancel and return to the beginning of the process. They may choose "Yes" or "No". "Yes" returns them to the beginning of the process. "No" returns them to the screen they were on when they hit the "Cancel" button), and the Request Assistance button can be designed to allow the patient to request assistance from the Attendant (e.g., the patient can receive a pop-up box notifying them that the attendant will be with them in a moment and the attendant also receive a notice that the patient requires assistance. The notice provided to the attendant can optionally be color coded and/or generate a certain sound to indicate the source and/or seriousness of the request by a patient and/or medical provider, etc.). The Patient Appointment or Registration Application can include a process through which the patient identifies themselves as a new and/or returning patient and either schedules an appointment at one or more medical kiosks or registers for an existing appointment at one or more medical kiosks. The medical kiosk can optionally be staffed by a medical assistant or attendant at all times. During the patient registration process, the medical assistant or attendant responsibilities, when used, can include welcoming the patient, offering assistance, validating patient identification, initiating/finalizing the patient consultation, and/or completing the sanitization process. As can be appreciated, the medical assistant or attendant can have other or additional responsibilities (e.g., check operation of medical kiosk, report a malfunction of a medical kiosk, monitor appointment status of medical kiosk, assist the patient in the medical kiosk, reload software, etc.). The Patient Appointment or Registration Application can optionally be designed to enable a patient to register and schedule appointments through one or more methods (e.g., on-line registration, calling a registration location, visiting a medical kiosk, etc.). During the patient registration process, the Patient Appointment or Registration Application can include scheduling software that provides a scheduling system for a patient to register with one or more medical kiosks. The scheduling system can be designed to be accessed by a patient on a data entry device on a medical kiosk, via a computer or phone or smart device, and/or by phone. The patient registration system can be designed to 1) schedule a new appoint for a patient, 2) schedule an appointment for a returning patient, and/or 3) welcome a patient that has already scheduled an appointment. In one non-limiting arrangement, the patient registration system generally asks if the patient is a returning patient, a new patient or if the patient requires assistance. The patient registration system generally provides the patient with a privacy policy associated with the use of the medical kiosk; however, this is not required. When a privacy policy is presented to the patient, the patient generally must acknowledge or accept the privacy policy before the patient can proceed further with the registration process; however, this is not required. The patient registration system generally provides the patient with terms of service policy associated with the use of the medical kiosk; however, this is not required. When the terms of service policy is presented to the patient, the patient generally must acknowledge or accept the terms of service policy before the patient can proceed further with the registration process; however, this is not required. The patient registration system generally asks why the patient is using the patient registration system (e.g., Medical kiosk tour, Medical kiosk demo, Medical kiosk payment demo, check-in for a medical visit, etc.). The patient registration system generally asks the patient to enter a password, phone number, pin number, name, email address, address, date or birth, sex, or the like to identify the patient; however, this is not required. The patient registration system generally asks the patient to verify if the patient is at least a certain age (e.g., at least two years old, etc.) before medical services can be provided by the medical kiosk; however, this is not required. The patient registration system generally asks the patient to identify one or more symptoms (e.g., body aches, chest congestion, cough, diarrhea, ear ache or pain, eye itching or swelling, fatigue, fever, headache, nasal congestion, nausea, pink eye, shortness of breath, skin rash, urinary problems, constipation, wheezing, cramps, pulled muscle, stomach pains, indigestion, gas problems, swelling, etc.) that the patient is experiencing in which the patient is seeking medical assistance; however, this is not required. The patient registration system may optionally ask one or more follow-up questions after the patient enters the one or more symptoms and/or may inform the patient to seek an in-person visit by a medical provider; however, this is not required. The patient registration system may optionally ask the patient to identify one or more known allergies of the patient (e.g., none, amoxicillin, aspirin, bee stings, cosmetics, eggs, fish, hay fever, hives, latex, metals, milk, mold, MSG, nuts, drugs, penicillin, pets, poison ivy, shellfish, soy, sulfa, sun, wheat, other, etc.); however, this is not required. The patient registration system may optionally ask the patient to identify one or more known medical conditions of the patient (e.g., none, alcoholism, arthritis, asthma, breast cancer, chronic ear infections, diabetes, emphysema, enlarged prostate, glaucoma, heat attach, high blood pressure, high cholesterol, liver problems, other cancer, skin cancer, stroke, thyroid problems, tuberculosis, other, etc.); however, this is not required. The patient registration system may optionally ask the patient to identify one or more past medical procedures that have been performed on the patient; however, this is not required. The patient registration system may optionally ask the patient to identify one or more medications the patient is taking; however, this is not required. The patient registration system may optionally ask the patient if the patient has medical insurance; however, this is not required. If medical insurance is inquired about and the patient indicates that he/she has medical insurance, the patient registration system may optionally ask the patient to enter in the medical insurance information (e.g., insurer name, ID number, policy number, etc.) and/or to scan the insurance card; however, this is not required. The patient registration system may optionally ask the patient to make a copay based the medical insurance or to fully pay for the medical visit; however, this is not required. Such payments, if any, can be by cash, check, debit card, credit card, smart device, etc.). For debit and credit cards and smart devices, the medical kiosk may include a card reader or scanner or RFID system, and/or may include a key pad to enter the charge or credit information; however, this is not required. A medical assistant or attendant of the medical kiosk can optionally assist the patient with the payment of services and/or with any other check-in step of the patient registration system; however, this is not required. For example, the patient registration system may include a button or other request arrangement to signal to a medical assistance or attendant, if used, that the patient need assistance with one or more steps of the registration process; however, this is not required. Once the patient is registered, the patient registration system will list one or more days and/or times that the medical kiosk is available for use by the patient; however, this is not required. The time intervals can be spaced by a certain time period (e.g., every twenty minutes, every thirty minutes, etc.); however, this is not required. The patient registration system can verify that an appointment has been made by the patient once all of the required information and optional payment has been made; however, this is not required. Such verification can be merely displayed on the patient registration system, printed out for the patient, emailed or texted to the patient or left on a voicemail of the patient; however, this is not required. If the patient is a returning patient, the patient may merely need to enter the ID information to access the information that patient had previously entered and then optionally update such information; however, this is not required. A previous patient may be asked about the new visit (e.g., follow-up, new symptoms, etc.); however, this is not required. The previous patient may optionally be asked to update insurance information, reenter insurance information, etc. and then optionally make the required copay or full payment. If the returning patient is merely returning to a scheduled appointment, the patient may need to enter the ID information and verify that the patient is present and is checked-in or cancelling the scheduled appointment; however, this is not required. A medical assistant or attendant can optionally provide assistance to a patient during any step of the check-in or registration process or recheck-in process; however, this is not required. The information entered and/or scanned regarding the patient can optionally be saved to a file for current and/or later access by the patient, medical provider, medical assistant, etc.; however, this is not required. Such store information is generally saved on a database, server, etc. that is located remote to the medical kiosk; however, this is not required.

In still another and/or alternative non-limiting aspect of the invention, the novel method and apparatus for providing medical services, diagnoses, health, and/or wellness advice to individuals can include the use of one or more medical assistants or attendants with the medical kiosk; however, this is not required. In one non-limiting embodiment of the invention, the medical kiosk can have one or more attendants assist a patient during the use of the medical kiosk (e.g., assist in check-in procedures, assist check-out procedures, assist in entering/exiting the medical kiosk, answering questions about the medical kiosk, assist the patient about the use of the kiosk, assist the patient during examination of the patient by the medical provider, assist in maintaining privacy/security of a patient while using the medical kiosk, assist user during payment of medical services, assist user in obtaining a prescription, assist in answering general questions about the medical kiosk, assist the remote medical provider during the examination of the patient, assist in using one or more medical devices on the patient, cleaning the medical kiosk, maintaining the systems of the medical kiosk, resetting the medical kiosk for use by another patient, assist in processing of payments and/or insurance information of a patient, monitor proper use of the medical kiosk, etc.); however, this is not required. Such attendant, when used, can be a medical provider or non-medical provider. The assistant may or may not have any formal medical education. The one or more attendants, when used, can also or alternatively clean and/or sanitize various regions of the medical kiosk prior to and/or after being used by a patient and/or set up the medical kiosk for a new user; however, this is not required. For example, prior to and/or after one or more patients have entered the medical kiosk, the one or more attendants can clean/sanitize one or more exterior surfaces and/or regions of the medical kiosk (e.g., medical kiosk door, medical kiosk check-in terminal, medical kiosk desk top, medical kiosk exterior walls, medical kiosk touch screen, medical kiosk monitors, seating/tables in waiting area near medical kiosk, etc.); however, this is not required. In an another and/or additional example, prior to and/or after one or more patients have entered the medical kiosk, the one or more attendants can clean/sanitize one or more interior surfaces of the medical kiosk (e.g., medical kiosk door, medical kiosk floor, medical kiosk bench, medical kiosk chair, medical kiosk user terminal, medical kiosk interior desk top, medical kiosk interior walls, medical kiosk touch screen, medical kiosk monitors, medical kiosk instrument doors, medical devices/instruments used by and/or touched by user when in the medical kiosk, any other surface in the interior of the medical kiosk, etc.); however, this is not required. In still another and/or additional example, prior to and/or after one or more patients have entered the medical kiosk, the one or more attendants can set up the medical kiosk for a user (e.g., clean/sanitize interior surfaces of medical kiosk; clean/sanitize medical devices/instruments used and/or touched by a prior user; reposition medical devices/instruments into device storage areas; replace disposable components on medical devices/instruments; replenish paper in a printer; clear a paper jam in a printer; replace batteries for one or more electronic components; close medical device/instrument compartments doors in the medical kiosk; reset user touch screen for next user in the medical kiosk; fix, repair and/or replace non-operating, damaged or broken medical devices/instruments in the medical kiosk; fix, repair and/or replace electronic components, computers, fans, light bulbs, UV bulbs, UV devices, etc. in the interior and/or exterior of the medical kiosk; refill cleaning and/or sanitizing fluid; etc.); however, this is not required. In yet another and/or additional example, the one or more attendants can be used to assist one or more users in the medical kiosk. Generally, such assistance will occur only after requested by the user in the medical kiosk or by the medical provider that is assisting the user while in the medical kiosk; however, this is not required. For instance, the one or more attendants can assist a user in the medical kiosk if the one or more attendants hear a verbal request from the user, receive notice (e.g., light indicator activated by user, sound indicator activated by user, hear user talking via a speaker to attendant, hear user talking through walls of medical kiosk, receive a notice from the medical provider [e.g., phone call, email, light indicator, etc.], etc.); however, this is not required. The one or more medical assistants can be positioned at a desk or table that is positioned adjacent to or connected to the exterior of the medical kiosk; however, this is not required. The medical assistant can be provided with a computer, tablet, etc. to monitor the appointment for the medical kiosk, to cancel an appointment, to reschedule and appointment, to indicate if a patient missed an appoint or is late for an appointment, validate the ID of a patient, to view appointment information of the medical kiosk, to validate a patient's insurance, to monitor the need for the assistant to assist a patient via patient or medical provider request, to monitor the status of the visit by the patient (e.g., medical kiosk cleaned for patient, the patient has properly checked-in, appointed has started and vitals capture process has begun, vitals capture process completed, video consultation by medical provider with patient has begun, the video consultation with the medical provider has been completed, the medical provider is completing the patient report, the visit by the patient in the medical kiosk is completed, etc.), to assist in insurance and information processing and/or scheduling of a patient, to assist in the payment by the patient for medical services, to print out reports and/or email reports to patient that provides a summary or complete report to the patient regarding the visit to the medical kiosk, to activate the sanitation system of the medical kiosk (e.g., UV sanitation system, etc.), to keep a record of when the kiosk was cleaned/sanitized and/or what was cleaned/sanitized by the assistance (e.g., clean patient counter, clean patient touch screen desk, clean patient bench, clean entry doors, clean thermometer, clean dermascope, clean patient chair, clean interior walls, clean medical doors and handles, clean otoscope, clean pulse-ox, clean floor, clean scale, clean video monitor, clean exterior of the medical kiosk, clean the medical assistant desk, clean the check-in screen on the exterior of the medical kiosk, clean walk-in mat, clean door tracks, clean UVC panel, clean inside ceiling, clean top of medical kiosk, clean UVC lights, clean medical device compartments, etc.), to enter information about the operation of the medical kiosk, to schedule a service call for the medical kiosk, to order parts or accessories for the medical kiosk, to verify the start and completion of an appointment, to process comment information by a patient, to create and/or send reports regarding the use of the medical kiosk, to escort the patient into and/or out of the medical kiosk, to begin the vitals capture of the patient, provide information and/or instructions to a patient regarding the medical kiosk and/or regarding the proper use of the medical kiosk, to assist a potential patient in a tour of the medical kiosk, etc.

In yet another and/or alternative non-limiting aspect of the invention, the novel method and apparatus for providing medical services, diagnoses, health, and/or wellness advice to individuals can include the use of an Attendant Application. The Attendant Application includes software and/or hardware that enables the attendant to 1) monitor, modify and/or cancel existing appointments for a medical kiosk, 2) monitor whether a patient requires assistance, 3) monitor and/or assistant a patient during registration with the medical kiosk, 4) provide procedures and/or check lists for the medical assistant, and/or 5) provide information on the status of the medical kiosk. As can be appreciated, the Attendant Application can have other and/or additional functions. In one non-limiting arrangement, the initial Attendant's screen, displays one or more appointment fields (e.g., time, patient name, medical provider name, status, action, etc.). For examples, the time field, when used, can be designed to display the time of upcoming appointments on the medical kiosk; the patient name field, when used, can be designed to display the name of the patients for upcoming appointments on the medical kiosk, the provider name field, when used, can be designed to display the name of the providers for upcoming appointments on the medical kiosk, the status field, when used, can be designed to display the status of upcoming appointments on the medical kiosk (e.g., Ready—The medical kiosk has been sanitized and is ready for the next patient appointment, Checked-In—The patient has been checked-in and their appointment is pending, Pre Consult—The appointment has started and vitals capture process is in progress, In Visit—The vitals capture process has been completed and the video consultation with the medical provider is in progress, Post Consult—The video consultation with the medical provider has been completed and the medical provider is completing the visit, Completed—The appointment has been completed, etc.), and the actions field, when used, can be designed to display the available of the Attendant functions. The actions field, when used, can be designed to allow for one or more actions (e.g., "X" Icon, Clock Icon, Printer Icon, Emergency Clean-Up Icon, etc. The "X" Icon, when used, can be design to perform one or more functions such as to cancel an upcoming appointment; however, this is not required. The "X" Icon can also allow entry and/or selection of a reason for cancellation (e.g., No Show—This action cancels the appointment, but maintains the patient record; Can't Make Appointment (Not Rescheduling)—This action cancels the appointment, but maintains the patient record; Patient Changed Mind—This action cancels the appointment, but maintains the patient record; Cancel Cancellation—This action cancels the cancellation; etc.). The "Clock" Icon, when used, can be designed to reschedule an upcoming appointment; however, this is not required. When this Icon is selected, entry and/or selection of one or more types of data can be allowed (e.g., input a date and time to reschedule an appointment, etc.); however, this is not required. The "Printer" Icon, when used, can be designed to print a visit summary and/or some other type of information (e.g., prescription, coupons, follow-up visit information, survey and/or survey results, etc.); however, this is not required. This Icon can be designed to only appear after an appointment has been completed and/or scheduled; however, this is not required. The "Emergency Clean-Up" Icon, when used, can be designed to allow the medical attendant to associate an emergency clean-up with a patient appointment so as to be used for tracking purposes and/or some other purpose; however, this is not required. Upon selection of the "Emergency Clean-Up" Icon, the medical attendant can be allowed to type a note regarding the emergency clean-up; however, this is not required.

In still yet another and/or alternative non-limiting aspect of the invention, the novel method and apparatus for providing medical services, diagnoses, health, and/or wellness advice to individuals can include the use of an Attendant Application that allows the medical attendant to 1) view appointment information, 2) validate patient IDs, 3) validate patient insurance, 4) reschedule or cancel an appointment, and/or 5) perform the sanitization process for the medical kiosk; however, this is not required. In one non-limiting embodiment of the invention, once the patient is "Checked-In" via the patient registration process, the appointment status changes to "Pending." At that time, the medical attendant can be required to validate the patient's ID; however, this is not required. For example, the medical attendant can 1) select the patient records (e.g., from the computer screen or monitor, etc.) and 2) select the "Validate Patient ID" button or similar type of button or selection; however, this is not required. If the patient is a new patient, the medical attendant can be prompted to insert and scan the patient's identification for the first time to be saved in the patient's electronic file. If the patient is a returning patient, the medical attendant can be prompted to "Update Patient ID". If "Update Patient ID" is selected, the medical attendant can be prompted to "Start Scan" of updated patient ID. Once the patient's ID is validated and scanned, the medical attendant may be required to rescan the ID (if image quality is compromised) or save the image in the patient's file; however, this is not required. As can be appreciated, other or additional methods can be used to validate a patient's ID. In one non-limiting arrangement, the patient's identification is validated by use of a valid driver's license, US passport, military ID, and/or photo ID card issued by Federal, State, or Local government. As can be appreciated, other or additional types of IDs can be used. If the patient is under 18 or some other age designating a minor, the patient may be required to be accompanied by a parent or legal guardian; however, this is not required. If the patient is not accompanied by a parent or legal guardian, the patient may not be allowed to proceed with the visit. The medical assistant may be required to inform the under 18 or minor age patient of certain rights when using the medical kiosk (e.g., It is not necessary for the parent or legal guardian to accompany the under 18 patient into the consultation; Anyone under 18 years of age needs to have parent or legal guardian to use the medical kiosk, etc.); however, this is not required. If the patient is under a certain age (e.g., 2 years old, etc.), the medical attendant may be required to inform the patient, parent and/or guardian that the patient to too young to use the medical kiosk, thus cannot proceed with the visit; however, this is not required. If a new patient indicates that they have insurance or a returning patient indicates their insurance information has changed, the patient may be prompted to see the medical attendant and/or be required to enter the insurance information; however, this is not required. The Attendant Application can prompt the medical attendant to for entry of a copay amount and/or to scan the insurance card into the patient record; however, this is not required. As can be appreciated, the patient can enter the insurance information without a medical attendant and/or make a copayment without the medical attendant; however, this is not required. Once the patient's insurance is validated and entered and/or scanned, the medical attendant or patient may be required to rescan the ID (if image quality is compromised) and/or reenter the information if not entered properly or save the image and/or entered insurance information into the patient's file; however, this is not required. If the insurance information is not verified at a first try, the patient or medical attendant can attempt to reverify the insurance information; however, this is not required. Once the patient insurance is saved, the patient can be prompted to "Check in" for the next available appointment or select some appointment time and/or day in the future; however, this is not required. Once the patient is checked-in for a visit to the kiosk, the appointment status will change to "Pre Consult" or some other statement on the screen of the Attendant Application; however, this is not required. At that time, the medical attendant may be required to recite a "Pre-Visit Summary" (e.g., "After your appointment is verified, you will step into the medical kiosk, your vitals are captured and you will meet with a medical provider over a video connection. The medical provider will provide the diagnoses and you may receive a prescription. The prescription can be sent to a pharmacy of your choice, etc.); however, this is not required. Once the patient is checked-in and after any optional statement is made to the patient, the patient can enter the medical kiosk. The medical attendant may be required to escort the patient into the medical kiosk to initiate the vitals capture and/or consultation; however, this is not required. The medical attendant and/or patient can cause the Provider Application to prompts the medical provider to start the medical visit; however, this is not required. Once the medical provider completes the appointment via the Provider Application, the appointment status on the Attendant Application for a particular patient can be designed to change to "Completed". Once the patient visit has completed the medical visit and exited the medical kiosk, the medical attendant may be required to perform a sanitization process; however, this is not required. Such sanitation process can include the medical attendant 1) selecting the patient record on the screen, and 2) selecting the "Start Sanitization" button or similar labeled button or selection. The medical attendant can enter the medical kiosk and perform the sanitization process. A screen that includes a check list or a paper check list can be used by the medical attendant to check off items that have been sanitized. For example, a screen inside the medical kiosk can include a check list and the medical assistant checks off each item as such item is sanitized by the medical attendant; however, this is not required. When all items are sanitized and optionally checked off, the medical attendant can select a button on the Attendant Application that the sanitation step is completed; however, this is not required. The medical attendant can optionally select to "Run UVC Light" or some other or additional automated sanitation system if such option is available; however, this is not required. Areas of the medical kiosk that can be cleaned after each visit and/or cleaned at period times based on some protocol are: patient counter, patient monitor screen, physician monitor screen, patient chair, seat at rear of station, kiosk wall panels, medical devices, medical device doors and handles, interior of kiosk, entry door of kiosk, internal wood surfaces in kiosk, attendant station, walk in door mat, floor of kiosk, door track of kiosk, external display monitor of kiosk, external surfaces of kiosk, UVC panel in kiosk, and/or UVC lights. The surfaces can be cleaned with wipes (e.g., Virox wipes [Towelettes with disinfecting chemicals that kill 99% of viruses and bacteria], glass cleaner, surface cleaners, floor cleaners, duster, dusting cloth, etc. Upon completion of the sanitization process, the medical kiosk status can return to "Ready" on the Attendant Application; however, this is not required. At that point, the medical attendant can start validation of the next patient's ID.

In another and/or alternative non-limiting aspect of the invention, the novel method and apparatus for providing medical services, diagnoses, health, and/or wellness advice to individuals can include the use of a Patient Appointment or Registration Application to navigate patients through the vitals capture process, patient consultation, and/or survey; however, this is not required. The Patient Appointment or Registration Application can contain one or more navigational buttons on the patient screen that is located inside the medical kiosk (e.g., back, next, cancel, request assistance, etc.); however, this is not required. The "Back" button, when used, allows the patient to return to the previous screen. The "Next" button, when used, allows the patient to proceed to the next screen. The "Cancel" button, when used, allows the patient to cancel a process and return to the beginning of the process. The patient can optionally receive a request to confirm the cancel procedure; however, this is not required. The "Request Assistance" button, when used, allows the patient to request assistance from the medical attendant. The selection of this button can be designed to also notify the patient that the medical attendant will be with them in a moment; however, this is not required. The selection of the "Request Assistance" button by the patient can result in the Attendant Application displaying on a screen a notice or generating a warning sound, etc. that the patient has requested assistance. For example, when the patient initiates the "Request Assistance" button, a pop-up box (e.g., orange box, red box, blue box, etc.) can appear on the medical attendant's screen that is labeled "kiosk," colored orange, and indicates the patient requires assistance. As can be appreciated, the screen of the Provider Application, when used, can include an "Alert Attendant" button to notify the medical attendant that the patient requires assistance; however, this is not required. If the medical provider initiates the "Alert Attendant" button from the Provider Application, a pop-up box can be designed to appear on the medical attendant's screen that indicates the patient requires assistance. The pop-up box can be a colored box (e.g., red box, green box, orange box, etc.); however, this is not required. A sound can also or alternatively be generated by the Attendant Application, when used, to notify the medical attendant that the medical provider has selected the "Alert Attendant" button; however, this is not required. The Patient Appointment or Registration Application, when used, can be designed to allow the patient to 1) capture vitals, 2) perform the provider consultation, and/or 3) perform the survey. As can be appreciated, the Patient Appointment or Registration Application, when used, can be designed to allow the patient to perform other or additional functions. The Patient Appointment or Registration Application can be designed to appear on the Patient Screen and/or Provider Screen that are located in the interior of the medical kiosk; however, this is not required. The Provider Screen, when used, is the screen that is located above or adjacent to the Patient Screen; however, this is not required. The medical provider generally appears on the Provider Screen when the consultation starts; however, this is not required. The Patient Screen, when used, can provide information to the patient while located in the kiosk and/or allow the patient to enter information (e.g., patient receives vitals capture instructions on the Patient Screen and enters information as prompted, etc.). The Patient Appointment or Registration Application can be designed to capture vitals of the patient. The Patient Appointment or Registration Application can be designed to require the patient to initiate the capture vital procedure and/or the medical attendant can the capture vital procedure for the patient. The Patient Appointment or Registration Application can be designed to navigate the patient and/or provide instructions to the patient for one or more of the vital capture procedures; however, this is not required. During the vital capture process, the patient can request that the medical assistant assist the patient in one or more of the procedures for capturing the vital; however, this is not required. The Patient Appointment or Registration Application can be designed require the patient to confirm that instructions for a particular vital capture procedure have been read and/or understood before proceeding with the next vital capture step; however, this is not required. The Patient Appointment or Registration Application can be designed to have the patient enter his/her height on the Provider Screen and/or Patient Screen; however, this is not required. The interior of the medical kiosk can include a height marker or height tape to enable a patient to determine his/her height; however, this is not required. The medical kiosk can include a camera or some other type of arrangement that can be used to automatically determine the height of the patient while the patient is positioned in the medical kiosk; however, this is not required. The Patient Appointment or Registration Application can be designed have the patient enter his/her weight on the Provider Screen and/or Patient Screen; however, this is not required. The interior of the medical kiosk can include a scale (e.g., built-in floor scale, etc.) that can be used by the patient to determine the patient's weight; however, this is not required. When a scale is provided in the medical kiosk, the weight can be automatically transferred to the Patient Appointment or Registration Application and/or can be manually entered by the patient. The Patient Appointment or Registration Application can be designed to have the patient obtain his/her temperature. The Patient Appointment or Registration Application can be designed to open a medical device cabinet that contains a thermometer; however, this is not required. The Patient Appointment or Registration Application can be designed to provide instructions and/or a video on how to use the thermometer (e.g., a) remove thermometer from open medical cabinet, b) place thermometer in ear, c) remove thermometer from ear after hearing a beep sound or other indicator that indicates procedure is completed, d) return thermometer to medical cabinet, etc.); however, this is not required. The Patient Appointment or Registration Application can be designed to have the patient obtain his/her blood pressure. The Patient Appointment or Registration Application can be designed to open a medical device cabinet that contains a blood pressure cuff and/or allows the blood pressure cuff to be plugged into the medical kiosk; however, this is not required. The Patient Appointment or Registration Application can be designed to provide instructions and/or a video on how to use the blood pressure cuff; however, this is not required. As can be appreciated, the medical attendant can place the blood pressure cuff on the patient entering the medical kiosk and/or after the patient has entered the medical kiosk; however, this is not required. If the blood pressure cuff requires that it be connected to the medical kiosk, the medical attendant or the patient can perform such connection. The patient or the medical attendant can start the blood pressure reading by selecting a button on the Patient Appointment or Registration Application; however, this is not required. The blood pressure cuff can be used to measure the blood pressure/heart rate of a patient. A real-time reading of the blood pressure/heart rate of a patient can be displayed on the Patient Screen and/or Provider Screen; however, this is not required. The patient or medical attendant can stop the process of capturing the blood pressure/heart rate of the patient; however, this is not required. After the completion of capturing of all the vitals, The Patient Appointment or Registration Application can be designed to display on the Patient Screen and/or Provider Screen a summary of one or more of the captured vitals. Patient Appointment or Registration Application can be designed to allow a patient to manually change one or more of the collected vials; however, this is not required. Once the vital capture process is completed, the patient can be prompted (e.g., "I'm Ready" button, etc.) to indicate that the patient is ready for the conference with the medical provider; however, this is not required. The Patient Appointment or Registration Application can be designed to notify the patient that the medical provider will be with them shortly; however, this is not required. Once the consultation has begun, the Patient Appointment or Registration Application can be designed to cause the medical provider to appear on the lower half of the Provider Screen and the patient's vitals appear on the upper half of the Provider Screen; however, this is not required. As can be appreciated, the full Provider Screen can only include the medical provider. The Patient Appointment or Registration Application can be designed to allow the patient to adjust the volume by use of volume buttons on the Patient Screen; however, this is not required. As can be appreciated, volume control can be located in other or additional locations in the medical kiosk. After the completion of the consultation, the Patient Appointment or Registration Application can be designed to ask the patient to complete a survey; however, this is not required. The Patient Appointment or Registration Application can be designed to allow the patient to skip the survey, when used, or to proceed with the survey; however, this is not required. If the patient selects the survey, when offered, one or more questions can be displayed on the Patient Screen and/or Provider Screen; however, this is not required. As can be appreciated, the medical attendant can provide the patient with a written survey and/or ask verbal survey questions; however, this is not required. At the completion of the survey, or if the patient chooses to skip the survey when such survey is offered, the Patient Appointment or Registration Application can be designed display a final screen thanking the patient for his/her visit and/or prompting them to request a visit summary from the medical attendant; however, this is not required.

In still another and/or alternative non-limiting aspect of the invention, the novel method and apparatus for providing medical services, diagnoses, health, and/or wellness advice to individuals can include the use of a Provider Application that is designed to enable the medical provider to navigate through the appoint process during the patient appointment. The Provider Application can be designed to allow the medical provider to a) display appointment, b) display patient information, c) view and/or modify visit information, d) perform the consultation, and/or e) utilize one or more medical devices in the medical kiosk. The Provider Application can be designed to cause screens to appear on the medical provider's computer, smart phone, tablet, etc. at the medical provider's remote location; however, this is not required. Upon entering the Provider Application, the medical provider, the Provider Application can be designed to enable the medical provider to view appointments that have been completed by the medical provider, that are in progress by the medical provider and/or which are future appointments. In one non-limiting arrangement, the Provider Application can be designed to enable the medical provider to view appointments that have been completed by the medical provider or are in progress for a certain day (e.g., today, last Monday, etc.). In another non-limiting arrangement, the Provider Application can be designed to enable the medical provider to view appointments that have been made for a future time (e.g., two hours from the present, the next day, etc.). For example, the Provider Application can be designed to display on one portion of the screen (e.g., left side, right side, center, etc.) appointments for "Today" and "Future." In one non-limiting arrangement, the "Today" tab can be designed to display one or more types of patient appointment information (e.g., Time—Time of appointment, Patient Name—Patient Name for appointment, Status—Status of appointment, Pending—Patient started the registration process, but has not yet been approved for payment, Checked-In—Patient has been checked-in, Pre Consult—Appointment has started and vitals are being collected, In Visit—Vitals have been collected and the video consultation is in-progress, Post Consult—Video consultation has been completed and medical provider completion is pending, Completed—Appointment has been completed, etc.). The "Future" tab can be designed to display one or more types of patient appointment information (e.g., Date—Date of appointment, Time—Time of appointment, Patient Name—Patient Name for appointment, etc.). The Provider Application can be designed to enable the medical provider to view a selected record on another portion of the screen; however, this is not required. The selected record can provide the medical provider one or more types of information (e.g., Patient Name, Patient Date of Birth, Patient Sex, Symptoms, Medical Conditions, Date of Last Visit, Diagnosis, Allergies, Medications, Prior Visit Record of Patient, Medical Records of Patient, etc.). The Provider Application can be designed to enable the medical provider notify the medical attendant that the patient requires assistance; however, this is not required. The Provider Application can be designed to enable the medical provider to view the appointment and/or patient information prior to the vitals capture process. The Provider Application can be designed to limit access to a patient's information until a certain point (e.g., patient status is "Checked-In", etc.); however, this is not required. The Provider Application can be designed to enable the medical provider to refuse an appointment that has been created for the medical provider; however, this is not required. Generally, such refusal should occur prior to the patient status of "Checked-In" to enable the system to locate another available medical provider; however, this is not required. The Provider Application can be designed to allow the medical provider to begin the conference with the patient once the patient is ready in the medical kiosk (e.g., after "Check-In", after "Capture of Vitals", etc.); however, this is not required. The Provider Application can be designed to cause a "Start Visit" button or similar button to appear on the medical provider's screen to allow the medical provider to begin the consultation with patient; however, this is not required. Once the visit or consultation has been initiated, the Provider Application can be designed to update the appointment status to "In Visit"; however, this is not required. Once the visit or consultation has begun, the patient appears on a portion of the medical provider's screen (e.g., right side of screen, center of screen, left side of screen, etc.); however, this is not required. The medical provider may greet the patient in the medical kiosk with a greeting (e.g., "Welcome to HealthSpot's Station at _____, can you see me ok? Can you hear me ok?", etc.); however, this is not required. The Provider Application can be designed to cause an "End Consultation" or similar button to appear on the medical provider's screen to terminate the consultation or visit with the patient and thereby terminate the video link between the medical provider and patient in the medical kiosk; however, this is not required. Once the consultation or visit with the patient is terminated, the Provider Application can be designed to cause the status of the patient to change to "Post Consult"; however, this is not required "Post Consult" means the video consultation has been completed and the medical provider is completing the visit summary. Once the medical provider has completed the visit summary and written any require prescriptions, the Provider Application can be designed to cause a "Complete Appointment" or similar button to appear on the medical provider's screen; however, this is not required. The selection of the "Complete Appointment" button or similar button after completion of the video consultation can result in the status of the patient to change to "Completed"; however, this is not required "Completed" means the medical provider has completed input of all information and is ready to commence the next appointment. The Provider Application can be designed to allow the medical provider to view the patient records, including the vitals capture process that has occurred or is occurring in the medical kiosk. The Provider Application can be designed to cause one or more tabs to be displayed on the medical provider's screen once a patient record has been selected (e.g., Patient Information, Current Visit, Previous Visit, etc.). The "Patient Information" tab, when used, can list one or more types of information of the patient on the medical provider's screen (e.g., Personal Information, Medications, Allergies, Medical Conditions, etc.). One or more of these categories of information can be further expanded upon selection by the medical provider; however, this is not required. For example, selection of the Personal Information category can cause further information about the patient to be displayed (e.g., date of birth, sex, alcohol usage, smoker status, race, eye color, native language, citizenship, address, etc.); however, this is not required. The "Current Visit" tab, when used, can list one or more types of information of the patient on the medical provider's screen (e.g., Medications, Notes, Vitals, Devices, Visit Summary, Attendant Instruction, etc.). One or more of these categories of information can be further expanded upon selection by the medical provider; however, this is not required. For example, selection of the Medications category can cause further information about medications used by the patient (e.g., past medications used, past medications prescribed to patient, current medications used by the patient, etc.). The "Previous Visit" tab, when used, can list one or more types of information of the patient on the medical provider's screen (e.g., Symptoms, Notes, Vitals, Visit Summary, etc.). One or more of these categories of information can be further expanded upon selection by the medical provider; however, this is not required. For example, selection of the Vitals category can cause further information about the vitals that were captured during a previous visit to the current medical kiosk, some other medical kiosk, or at some other medical facility. In one non-limiting embodiment of the invention, the Provider Application is designed to cause at least three tabs to be displayed on the medical provider's screen once a patient record has been selected, namely Patient Information, Current Visit, and Previous Visit. The "Patient Information" tabs contains sections for Personal Information, Medications, Allergies, and Medical conditions; however, it can be appreciated that other or additional tab sections can be included. The "Personal Information" section contains one or more sub-sections, of which some or all the information was entered by the patient during the registration process. This information generally cannot be modified by the medical provider; however, this is not required. Non-limiting examples of information that can be displayed in the "Personal Information" section includes Date of Birth, Gender—Male or Female, Alcohol Use, Smoker, Race, Eye Color, Hair Color, Native Language, Citizenship, Address, etc. The "Medications" section allows the medical provider to see previously entered medications, search and select new medications, and/or remove medications the patient is no longer taking. The Provider Application can be designed to allow a medical provider to add a medication by having the medical provider type in the medication and/or to start typing the medication name in the "Search Medications" drop down and allow a listing of matching medication names to appear for selection and then to select the proper medication. The Provider Application can be designed to allow a medical provider to delete a medication by having the medical provider select an "X" next to the medication. As can be appreciated, other or additional arrangements can be used to add and/or delete medications in a patient's record. The "Allergies" section allows the medical provider to view allergies as input by the patient. This function allows the medical provider to see previously entered allergies, search and select new allergies, and/or remove allergies. The Provider Application can be designed to allow a medical provider to add an allergy by having the medical provider type in the allergy and/or to start typing the allergy name in the "Add Allergy" drop down and allow a listing of matching allergy names to appear for selection and then to select the proper allergy. The Provider Application can be designed to allow a medical provider to delete an allergy by having the medical provider select an "X" next to the allergy. As can be appreciated, other or additional arrangements can be used to add and/or delete allergies in a patient's record. The "Medical Conditions" section allows the medical provider to view patient medical conditions as input by the patient. This function allows the medical provider to see previously entered medical conditions, search and select new medical conditions, and/or remove medical conditions. The Provider Application can be designed to allow a medical provider to add a medical condition by having the medical provider type in the medical condition and/or to start typing the medical condition in the "Add Medical Condition" drop down and allow a listing of matching medical condition names to appear for selection and then to select the proper medical condition. The Provider Application can be designed to allow a medical provider to delete a medical condition by having the medical provider select an "X" next to the medical condition. As can be appreciated, other or additional arrangements can be used to add and/or delete medical conditions in a patient's record. The "Current Visit" tab contains sections for Symptoms, Notes, Vitals, Devices, Visit Summary, and Attendant; however, it can be appreciated that other or additional tab sections can be included. The "Symptoms" section contains all of the patient's symptoms for the current visit as input by the patient. This function allows the medical provider to see entered symptoms, search and select new symptoms, and remove symptoms. The Provider Application can be designed to allow a medical provider to add a symptom by having the medical provider type in the symptom and/or to start typing the symptom in the "Symptoms" drop down and allow a listing of matching symptom names to appear for selection and then to select the proper symptom. The Provider Application can be designed to allow a medical provider to delete a symptom by having the medical provider select an "X" next to the symptom. As can be appreciated, other or additional arrangements can be used to add and/or delete symptoms in a patient's record. The "Notes" section allows the medical provider to enter notes for the current visit. This information generally does not appear on the Appointment Summary and is intended for internal reference only; however, this is not required. The Provider Application can be designed to allow a medical provider to add or delete a note by type a note in the note texted box or by deleting a note in the note text box. As can be appreciated, other or additional arrangements can be used to add and/or delete notes in a patient's record. The "Vitals" section contains the patient's vitals for the current visit. They are displayed dynamically on the provider's screen as the vitals capture process takes place; however, this is not required. This function allows the medical provider to see the below vitals prior to starting and during the consultation; however, this is not required. This information is generally only displayed and cannot be updated; however, this is not required. Non-limiting vitals can include Height, Weight, Blood Pressure, Heart Rate, Oxygen Saturation, and Temperature. The "Devices" section contains icons of the medical devices that are located in the medical kiosk and/or can be used with the medical kiosk. On the interior of the medical kiosk there can be one or more medical containers (e.g., 1-10, 2, 4, 6, etc.), wherein one or more can be locked upon patient entry into the medical kiosk. The medical provider has the capability to unlock one or more of the medical cabinets in the medical kiosk as necessary. When the medical provider wants to unlock a medical device cabinet, the medical provider clicks on or selects the appropriate medical device icon on the medical provider's computer screen. This selection action can result in the activation of the medical device and/or the opening of the medical cabinet door that includes the selected medical device. An audible sound can be generated (e.g., sound of dropping door, sound of a lock unlocking, etc.) when access to a medical cabinet is granted to a patient; however, this is not required. As can be appreciated, a visual indicator can also or alternatively be used to indicate that a patient can access a particular medical cabinet; however, this is not required. Non-limiting medical devices can be included in the medical kiosk can be selected by the medical provider for use in a patient visit (e.g., Thermometer, Otoscope, Stethoscope, Dermascope, Pulse Oximeter, Spirometer, Blood Pressure Cuff, blood sugar analyzer, etc.). As can be appreciated, the medical attendant can provide one or more medical devices to a patient prior to and/or during the visit (e.g., Blood Pressure Cuff, etc.). The "Visit Summary" section is comprised of one or more sub-sections, some or all of which are input by the medical provider (e.g., Current Diagnoses, Treatment Plan, Follow-Up Care, Visit Documents, etc.). The "Current Diagnoses" section, when used, allows for the provider to input diagnoses codes and descriptions for the current visit. The medical provider can update and/or enter a diagnoses by entering the name of the diagnoses and/or an ICD code in a drop down menu and/or search menu. Once the diagnoses name has been entered and/or searched and located, the medical provider can add the diagnoses to the patient's record. More than one diagnoses can be added to a patient's record during a single visit. Once the one or more diagnoses are entered, such diagnoses can be optionally displayed under the "Current Diagnoses" section. The "Treatment Plan" section, when used, allows for the medical provider to input a treatment plan for the current visit. Such treatment plan can be typed by the medical provider into a text box and this information can appear on the Appointment Summary for the patient to reference; however, this is not required. The "Follow-Up Care" section, when used, allows for the medical provider to input follow-up care for the current visit. Such follow-up care plan can be typed by the medical provider into text box; however, this is not required. This information can appear on the Appointment Summary for the patient to reference; however, this is not required. The "Visit Document" section, when used, allows for the medical provider to input follow-up care for the current visit. The medical provider can include one or more visit documents and/or other types of documents (e.g., documents about the common cold, documents about rashes, documents about the flu, documents about lice, documents bout acne, etc.) which can be provided to the patient along with the Appointment Summary; however, this is not required. The "Attendant Instructions" section, when used, allows for the medical provider to input attendant instructions for the current visit. Such information can be entered into a text box by the medical provider. This information may or may not be provided to the patient. The "Previous Visit" tab contains information about prior medical visits by the patient. When the "Previous Visit" tab is selected, a drop-down box appears containing the dates of all previous visits. The medical provider can select a previous visit and then review information about the previous visit. In one non-limiting arrangement, when the previous visit date is selected, one or more sections are displayed (e.g., Symptoms, Notes, Vitals, Visit summary, etc.). The "Symptoms" section, when used, allows for the medical provider to view all of the patient's symptoms from the previous visit as input by the patient and/or medical provider. The "Notes" section, when used, allows the medical provider to view all notes for the previous visit that were inputted by the medical provider in the prior visit. The "Vitals" section, when used, allows for the medical provider to view all of the patient's vitals that were captured during previous visit. The "Visit Summary" section, when used, allows for the medical provider to view all visit summary information input during a prior visit. This section can include one or more subsections (e.g., Treatment Plan, Follow-up Care, Visit Documents, etc.).

In yet another and/or alternative non-limiting aspect of the invention, the novel method and apparatus for providing medical services, diagnoses, health, and/or wellness advice to individuals can include a method and a kiosk wherein before the video-conference between the medical provider and the patient begins, each patient starts with a Vitals Check to capture the following one or more of the information: Height, Weight, Temperature, Blood Pressure and/or Heart Rate.

In still yet another and/or alternative non-limiting aspect of the invention, the novel method and apparatus for providing medical services, diagnoses, health, and/or wellness advice to individuals can include a method and a kiosk wherein the kiosk includes six advanced medical device cabinets which are locked upon patient entry. During the patient consultation, the medical provider has the capability to unlock and lower these cabinets from the Provider Application on the Provider's computer. The following medical devices can be contained within the cabinets, namely a thermometer, an otoscope, a stethoscope, a dermascope, a pulse oximeteren and/or a blood pressure cuff. Additional medical devices can be included in the medical kiosk (e.g., scale, height tape, eye chart, blood sugar analyzer, etc.). The stethoscope, when used, is used for detecting sounds produced in the body that are conveyed to the ears of the listener. The medical kiosk stethoscope sounds are transmitted from the stethoscope in the medical device (e.g., hardwire, USB, Bluetooth, etc.) to the medical provider's stethoscope. On the interior of the medical kiosk, the stethoscope can be contained in the first medical device cabinet on the left; however, this is not required. The stethoscope can be activated by the medical provider via the Provider Application by the medical provider selecting the stethoscope icon the provider's screen; however, the stethoscope can be activate by other or additional arrangements. In one non-limiting arrangement, when the medical provider via the Provider Application selects the stethoscope icon on the provider's screen, the stethoscope in the medical kiosk is activated and the cabinet door in the medical kiosk for the stethoscope opens or drops down to enable the patient in the medical kiosk to access the stethoscope; however, this is not required. The medical provider can provide instructions to the patient on how to use the stethoscope (e.g., Once the patient has removed the device, request for patient to turn on the stethoscope on the stethoscope device. The "On" button is the lower most button on the device; it looks like a smiley face with one eye. Tell the patient to attempt to hold the device on the sides, while using it, so other buttons are not depressed, etc.) and/or instructions for use of the stethoscope can be provided on the Patient Screen and/or Provider Screen in the medical kiosk; however, this is not required. When the stethoscope is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the stethoscope and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider via the Provider Application can increase and/or decrease the volume received from the stethoscope; however, this is not required. As can be appreciated, the patient can increase and/or decrease the volume from the stethoscope; however, this is not required. The medical provider and/or patient can request assistance by the medical assistant related to the stethoscope if so required. The otoscope, when used, is a device used for examining the internal ear. The image generated by the otoscope in the medical kiosk can be displayed on the Patient's Screen and/or Provider's Screen in the medical kiosk and/or on the screen being used by the medical provider; however, this is not required. The transmission of the signal can be by various means (e.g., hardwire, USB, Bluetooth, etc.). On the interior of the medical kiosk, the otoscope can be contained in the second medical device cabinet on the left in the medical kiosk; however, this is not required. The otoscope can be activated by the medical provider via the Provider Application by the medical provider selecting the otoscope icon the provider's screen; however, the otoscope can be activated by other or additional arrangements. In one non-limiting arrangement, when the medical provider via the Provider Application selects the otoscope icon on the provider's screen, the otoscope in the medical kiosk is activated and the cabinet door in the medical kiosk for the otoscope opens or drops down to enable the patient in the medical kiosk to access the otoscope; however, this is not required. The medical provider can provide instructions to the patient on how to use the otoscope (e.g., Once the patient has pulled out the device, request for patient to place the otoscope in the appropriate ear lobe, then adjust the focus dial. The focus dial is on the top of the otoscope. The patient can push it to the top and then dial it down to determine to focus; To direct the patient to maneuver the otoscope for best image capture, use the interior of the medical kiosk as reference points. Once the device is in the patient's ear canal, instruct them (or the individual assisting them) to move the device towards the front, back, bottom, and top of the medical kiosk, etc.) and/or instructions for use of the otoscope can be provided on the Patient Screen and/or Provider Screen in the medical kiosk; however, this is not required. When the otoscope is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the otoscope and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider via the Provider Application can adjust the focus of the otoscope; however, this is not required. As can be appreciated, the patient can adjust the focus of the otoscope; however, this is not required. The medical provider and/or patient can request assistance by the medical assistant related to the otoscope if so required. The thermometer, when used, is used for detecting human internal heat. The temperature that is transmitted by the thermometer can be displayed on the Patient's Screen and/or Provider's Screen in the medical kiosk and/or on the screen being used by the medical provider; however, this is not required. The transmission of the signal can be by various means (e.g., hardwire, USB, Bluetooth, etc.). On the interior of the medical kiosk, the thermometer can be contained in the third medical device cabinet on the left in the medical kiosk; however, this is not required. The patient's temperature can be collected during the vitals capture process which is prior to the consultation with the medical provider; however, this is not required. If the medical providers wants the temperature to be retaken or if the temperature of the patient has not already been taken, the thermometer can be activated or reactivated by the medical provider via the Provider Application by the medical provider selecting the thermometer icon the provider's screen; however, the thermometer can be activate by other or additional arrangements. In one non-limiting arrangement, when the medical provider via the Provider Application selects the thermometer icon on the provider's screen, the thermometer in the medical kiosk is activated and the cabinet door in the medical kiosk for the thermometer opens or drops down, if not already open, to enable the patient in the medical kiosk to access the thermometer; however, this is not required. The medical provider can provide instructions to the patient on how to use the thermometer (e.g., Once the patient has pulled out the device, request for patient to turn on the thermometer. The "On" button is on the inside handle of the device; Request for the patient to insert the thermometer into their ear and press the button on top of the handle to start the reading. Once the patient's temperature is collected, a beep will sound; Once the beep is sounded to indicate the temperature reading has completed, the patient can hit the "Temperature Recorded" button on the patient screen, etc.) and/or instructions for use of the thermometer can be provided on the Patient Screen and/or Provider Screen in the medical kiosk; however, this is not required. When the thermometer is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the thermometer and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider and/or patient can request assistance by the medical assistant if so required. In one non-limiting arrangement, the temperature must register between 95.0 degrees and 105.9 degrees; however, this is not required. Temperatures under or above 95.0 degrees and 105.9 degrees can be designed to create an error and request the patient to manually enter their temperature, request the patient to try again to take a proper temperature, and/or request the medical assistant to assist the patient related to the thermometer; however, this is not required. The dermascope, when used, is used to visualize body surface, skin, hair, scalp, eyes, and/or throat with magnification and/or illumination. The image generated by the dermascope in the medical kiosk can be displayed on the Patient's Screen and/or Provider's Screen in the medical kiosk and/or on the screen being used by the medical provider; however, this is not required. The transmission of the signal can be by various means (e.g., hardwire, USB, Bluetooth, etc.). On the interior of the medical kiosk, the dermascope can be contained in the first medical device cabinet on the right in the medical kiosk; however, this is not required. The dermascope can be activated by the medical provider via the Provider Application by the medical provider selecting the dermascope icon the provider's screen; however, the dermascope can be activate by other or additional arrangements. In one non-limiting arrangement, when the medical provider via the Provider Application selects the dermascope icon on the provider's screen, the dermascope in the medical kiosk is activated and the cabinet door in the medical kiosk for the dermascope opens or drops down to enable the patient in the medical kiosk to access the dermascope; however, this is not required. The medical provider can provide instructions to the patient on how to use the dermascope (e.g., Once the patient has pulled out the device, request for patient to place the dermascope device at the appropriate place, then request for the patient to adjust the focus dial. The focus dial is on the top handle of the dermascope. The patient can push it to the top and then dial it down to determine appropriate focus, etc.) and/or instructions for use of the dermascope can be provided on the Patient Screen and/or Provider Screen in the medical kiosk; however, this is not required. When the dermascope is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the dermascope and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider via the Provider Application can adjust the focus of the dermascope; however, this is not required. As can be appreciated, the patient can adjust the focus of the dermascope; however, this is not required. The medical provider and/or patient can request assistance by the medical assistant related to the dermascope if so required. The pulse oximiter, when used, is used for measuring the amount of saturated hemoglobin in the tissue capillaries by transmitting a beam of light through the tissue to a receiver. The image generated by the pulse oximiter in the medical kiosk can be displayed on the Patient's Screen and/or Provider's Screen in the medical kiosk and/or on the screen being used by the medical provider; however, this is not required. The transmission of the signal can be by various means (e.g., hardwire, USB, Bluetooth, etc.). On the interior of the medical kiosk, the pulse oximiter can be contained in the second medical device cabinet on the right in the medical kiosk; however, this is not required. The pulse oximiter can be activated by the medical provider via the Provider Application by the medical provider selecting the pulse oximiter icon the provider's screen; however, the pulse oximiter can be activate by other or additional arrangements. In one non-limiting arrangement, when the medical provider via the Provider Application selects the pulse oximiter icon on the provider's screen, the pulse oximiter in the medical kiosk is activated and the cabinet door in the medical kiosk for the pulse oximiter opens or drops down to enable the patient in the medical kiosk to access the pulse oximiter; however, this is not required. The medical provider can provide instructions to the patient on how to use the pulse oximiter (e.g., Provider: Once the patient has pulled out the device, request for patient to place the device on their index finger as illustrated by the diagram on the top on the device. The picture is a finger nail print which should align to the patient's finger nail, etc.) and/or instructions for use of the pulse oximiter can be provided on the Patient Screen and/or Provider Screen in the medical kiosk; however, this is not required. When the pulse oximiter is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the pulse oximiter and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider via the Provider Application can adjust the focus of the pulse oximiter; however, this is not required. As can be appreciated, the patient can adjust the focus of the pulse oximiter; however, this is not required. The medical provider and/or patient can request assistance by the medical assistant related to the pulse oximiter if so required. The scale, when used, is used to obtain the weight of the patient. The weight that is transmitted by the scale can be displayed on the Patient's Screen and/or Provider's Screen in the medical kiosk and/or on the screen being used by the medical provider; however, this is not required. The transmission of the signal from the scale can be by various means (e.g., hardwire, USB, Bluetooth, etc.). On the interior of the medical kiosk, the scale can be located on the floor of the medical kiosk; however, this is not required. The patient's weight can be collected during the vitals capture process which is prior to the consultation with the medical provider; however, this is not required. If the medical providers wants the patient's weight to be retaken or if the patient's weight has not already been taken, the scale can be activated or reactivated by the medical provider via the Provider Application by the medical provider selecting the thermometer icon the provider's screen; however, the scale can be activate by other or additional arrangements. In one non-limiting arrangement, when the medical provider via the Provider Application selects the scale icon on the provider's screen, the scale in the medical kiosk is activated to enable the patient in the medical kiosk to obtain the weight of the patient; however, this is not required. The medical provider can provide instructions to the patient on how to use the scale (e.g., Request for the patient to step on the scale and wait for the recording to be completed, etc.) and/or instructions for use of the scale can be provided on the Patient Screen and/or Provider Screen in the medical kiosk; however, this is not required. When the scale is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the scale and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider and/or patient can request assistance by the medical assistant if so required. In one non-limiting arrangement, the weight must register no greater than 501 pound or some other upper limit; however, this is not required. Weights that are above the upper weight limit can be designed to create an error and request the patient to manually enter their weight, request the patient to try again to take a proper weight, and/or request the medical assistant to assist the patient related to the scale; however, this is not required. The scale can be positioned in any location in the medical kiosk (e.g., floor, bench, chair, etc.). In one non-limiting embodiment, the can be integrated into the medical kiosk in such a way that it at least partially incorporated in on the floor of the medical kiosk. In one non-limiting design, the scale is positioned flush with the floor so that it poses no safety challenges for the user/patient in the medical kiosk; however, this is not required. As can be appreciated, the size, shape, and type of scale are non-limiting. The scale in the floor of the kiosk can also optionally be used as designated standing location of a patient so that a height of the patient can be obtained by used of one or more cameras and/or other electron devices in the medical kiosk; however, this is not required. The blood pressure cuff, when used, is used to determine the arterial pressure of the systemic circulation. The information that is transmitted by the blood pressure cuff can be displayed on the Patient's Screen and/or Provider's Screen in the medical kiosk and/or on the screen being used by the medical provider; however, this is not required. The transmission of the signal from the scale can be by various means (e.g., hardwire, USB, Bluetooth, etc.). On the interior of the medical kiosk, the blood pressure cuff can be contained in the third medical device cabinet on the right in the medical kiosk; however, this is not required. Alternatively, the blood pressure cuff can be kept with the medical attendant, and the medical attendant then assists the patient in placing the blood pressure cuff on the patient prior to the patient entering the medical kiosk or while the patient is located in the medical kiosk; however, this is not required. The patient's blood pressure can be collected during the vitals capture process which is prior to the consultation with the medical provider; however, this is not required. If the medical providers wants the patient's blood pressure to be retaken or if the patient's blood pressure has not already been taken, the blood pressure cuff can be activated or reactivated by the medical provider via the Provider Application by the medical provider selecting the blood pressure cuff icon the provider's screen; however, the blood pressure cuff can be activate by other or additional arrangements. In one non-limiting arrangement, when the medical provider via the Provider Application selects the blood pressure cuff icon on the provider's screen, the blood pressure cuff in the medical kiosk is activated and the cabinet door in the medical kiosk for the blood pressure cuff opens or drops down to enable the patient in the medical kiosk to access the blood pressure cuff; however, this is not required. As can be appreciated, if the blood pressure cuff is not located in a medical cabinet, that patient can obtain the blood pressure cuff from the location that the blood pressure cuff currently exists in the medical kiosk or the medical assistant can provide the blood pressure cuff to the patient if the medical attendant is retaining the blood pressure cuff. In another non-limiting arrangement, the medical kiosk includes an ambidextrous blood pressure cuff. The cuff arm can optionally be mounted to the desk top to enable the blood pressure cuff to be moved from side to side of the desk top; however, this is not required. Such movement of the blood pressure cuff enables the blood pressure cuff to be positioned so that the left arm or right arm of a user can be inserted into the blood pressure cuff when the user is facing the desk top. As can be appreciated, when a blood pressure cuff is included in the medical kiosk, it can be mounted and/or positioned in the medical kiosk in a variety of ways. Information to and from the blood pressure cuff, when used, can be transmitted by wire and/or wirelessly to one or more computers, processors, storage devices, etc. in the medical kiosk and/or to a location remote from the medical kiosk. The ambidextrous blood pressure cuff, when used, may be made of high-strength plastic or any other sufficiently rigid and/or strong material (e.g., metal, composite material, etc.). The cuff arm can be designed to be manually moved by the patient/user, be remotely moved by the medical provider and/or medical kiosk assistant, and/or be electronically moved by the patient/user. The blood pressure cuff can be designed to be activated/deactivated by the patient/user and/or remotely by the medical provider and/or medical kiosk assistant. The medical provider can provide instructions to the patient on how to use the blood pressure cuff (e.g., The blood pressure cuff is most effective when the patient fully places their bicep in the cuff, with the palm of their hand facing the ceiling, etc.) and/or instructions for use of the blood pressure cuff can be provided on the Patient Screen and/or Provider Screen in the medical kiosk; however, this is not required. When the blood pressure cuff is activated, a video image can be designed to appear on the Provider Application (e.g., medical provider's screen) and/or the Provider Screen and/or Patient Screen that is located in the interior of the medical kiosk. If a video image option is available for display on the Provider Screen and/or Patient Screen that is located in the interior of the medical kiosk, the medical provider via the Provider Application can turn off such video image on the Provider Screen and/or Patient Screen; however, this is not required. The medical provider via the Provider Application can capture images and/or data generated by the blood pressure cuff and/or video camera in the medial kiosk for placement in the patient's file; however, this is not required. The medical provider via the Provider Application can optionally annotate an image once captured (e.g., use the paint brush and font icons to modify image, etc.) and/or show the captured image to the patient; however, this is not required. The medical provider via the Provider Application can start and/or stop the blood pressure operation; however, this is not required. As can be appreciated, the patient can start and/or stop the blood pressure operation; however, this is not required. The medical provider and/or patient can request assistance by the medical assistant related to the blood pressure cuff if so required.

In another and/or alternative non-limiting aspect of the invention, the novel method and apparatus for providing medical services, diagnoses, health, and/or wellness advice to individuals can include a scheduling application that 1) enables a medical provider to input the day and time the medical provider is available to conduct a visit with a patient in a medical kiosk, 2) obtains or collects information on appoints that have been made by one or more patients at one or more medical kiosks, and 3) assigns a medical provider to a particular appoint that has been made at a particular medical kiosk. The scheduling application can be designed to enable a patient to select a particular medical provider, gender of a medical provider, specialty of a medical provider, a medical provider that can speak a certain language, etc.; however, this is not required. The scheduling application can be designed to allow a medical provider to refuse an appointment with a particular patient; however, this is not required. If the medical provider refuses an appointment, the scheduling application can be designed to attempt to schedule a different appoint for the newly available time slot of the medical provider, or can block off such time and not reschedule a new appointment for such time period; however, this is not required. The scheduling application can be designed to select a medical provider for a particular appointment based on a set algorithm (e.g., available medical provider that has the largest time since last appointment, etc.) and/or by a random process. The scheduling application can be designed to attempt to select a new medical provider for a particular appointment if the originally selected medical provider is unable and/or unwilling to conduct a visit with a patient in the medical kiosk; however, this is not required.

In still another and/or alternative non-limiting aspect of the invention, the novel method and apparatus for providing medical services, diagnoses, health, and/or wellness advice to individuals can include a medication adherence application; however, this is not required. The medication adherence application can be designed to reduce medication errors. The medication adherence application can include a reminder for patients to take their meds and then optionally the system can automatically log when the patient takes their medication; however, this is not required. The medication adherence application can also include the ability to track a patient's compliance to taking their medication on time and/or provide automatic progress reports; however, this is not required. The medication adherence application can also include the ability to refer the patient to a pharmacist to answer any questions and/or for additional consultation; however, this is not required. Each user/patient utilizing the medical kiosk can be automatically enrolled in the e-script network, which network sends their prescriptions to the pharmacy of their choice; however, this is not required. The medication adherence application can be used to assist in improving patient outcomes and/or satisfaction. The medication adherence application of the present invention can be designed to be used on a screen in the medical kiosk, and/or on a computer screen and/or mobile device; however, this is not required. The medication adherence application of the present invention can be designed to generate a screen that includes one or more main buttons (e.g., 1) Speak to a _____ (e.g., Walgreens, CVS, Wal-Mart, etc.) Pharmacist now, 2) Change my medications alerts, 3) Learn about controlling my _____ (e.g., cholesterol, high blood pressure, diabetes, etc.), 4) Check orders status, 5) Refill Prescriptions, etc., 6) Transfer prescriptions to _____ (e.g., Walgreens, CVS, Wal-Mart, etc.), 7) Recommended dosage, 8) Period for taking medications, 9) Frequency for taking medications, 10) Information about medications, 11) Generic brands available for medications, 12) Request appointment to speak with a medical provider, 13) Entry of compliance information regarding medication usage by patient, etc.); however, this is not required. The screen can include additional buttons (e.g., help button, Finish button, etc.); however, this is not required. The screen can include advertising information; however, this is not required. The selection of one or more of the button can result in additional screens appearing based on the selected button; however, this is not required. If a user/patient needs further guidance from the pharmacist regarding the prescribed medication, the user/patient can select the first category button to request such information; however, this is not required. The patient/user can be provided a number to call and/or allow the user to send an email, make a phone call, etc. regarding the question. The user/patient can be provided the option to set a new appointment to meet with a medical provider regarding the medication; however, this is not required. The user/patient can be provided the option to change the medication alerts; however, this is not required. Such change can be requested by telephone, email, text, phone, etc. The frequency and/or type of alert and/or the manner in which the alert is sent to the user/patient (e.g., email, twitter, phone message, text, etc.) may also be modified by the user/patient; however, this is not required. The user/patient may be provided to option to obtain information about certain medical conditions (e.g., cholesterol, blood pressure, migraines, back pain, arthritis, allergies, flu, etc.); however, this is not required. The user/patient may be provided the option to obtain the order status, shipment status, etc. for a particular medication; however, this is not required. If allowable by current medication guidelines and/or medical plans, the patient may request to fill their prescriptions directly through the application; however, this is not required. The user/patient may be provided the option to change their preferred prescription location; however, this is not required. The user/patient may be provided the option to enter information as to whether the prescribed medications are being timely taken and in the proper amounts; however, this is not required. Periodic reports regarding medication compliance can be generated and provided to the user/patient via phone, email, text, twitter, etc.; however, this is not required. The medication adherence application of the present invention can be used to allow the patient to more easily obtain and understand the correct use of their prescriptions. In summary, the medication adherence software application allows a user/patient to 1) speak to a pharmacist, 2) change the patient's medications alerts, 3) learn about certain types of medical conditions, 4) check medication orders status, 5) check medication delivery status, 6) refill a prescriptions, 7) transfer prescriptions to a another location, 8) obtain information about recommended medication dosages, 9) obtain information about recommended times to take medications, 10) obtain information about recommended frequency for taking medications, 11) obtain information about medications, 12) obtain information about generic brands available for medications, 13) request an appointment to speak with a medical provider, 14) enter information regarding compliance information regarding medication usage by patient, and/or 15) receive compliance reports for patients regarding medication usage.

In yet another and/or alternative non-limiting aspect of the invention, the novel method and apparatus for providing medical services, diagnoses, health, and/or wellness advice to individuals can include an expandable mounting system for medical devices; however, this is not required. In one non-limiting embodiment of the invention, the medical kiosk includes one or more equipment chambers that can be positioned on or near the front interior wall of the medical kiosk; however, it can be appreciated that one or more equipment chambers can be positioned in other or additional regions of the medical kiosk. The equipment chambers are used to store one or more medical devices (e.g., stethoscope, otoscope, thermometer, dermascope, spirometer, pulse oximeter, heating pad, magnifying glass, tongue depressor, tweezers, blood glucometer etc.). The one or more equipment chambers can also or alternatively be used to include other types of materials (e.g., tissue, Band-Aid, gauze, cotton ball, disinfecting wipe, cortisone cream, anti-biotic cream/ointment, alcohol wipe, cotton swab, fabric wrap, etc.). The one or more equipment chambers generally include a door to limit access to the one or more equipment chambers; however, this is not required. The door, when used on one or more of the equipment chambers, can be manually openable/closeable, and/or the doors can be controllably opened/closed remotely by the medical provider and/or medical attendant. Generally, one or more of the doors are controllably opened and/or unlocked by the medical provider during the examination of the user in the medical kiosk; however, this is not required. After the user/patient has left the medical kiosk, the medical attendant can enter the medical kiosk, then clean the medical equipment that was handled or used by the prior user/patient and/or dispose of and/or replace items that were used and/or handled by the prior user/patient; however, this is not required. Thereafter, the medical attendant can restock, replace, and/or reposition the medical equipment and/or non-medical equipment in the equipment chambers and close the equipment chamber doors prior to the next user/patient entering the medical kiosk; however, this is not required. One or more types of medical equipment can be designed to transmit information by wire or wirelessly to electronic components in the medical kiosk and/or to the remotely located medical provider; however, this is not required. In one non-limiting arrangement, the medical kiosk can include six (6) equipment chambers having doors, three on each side of the desk top of the medical kiosk. As can be appreciated, a larger or smaller number of equipment chambers can be used and/or the one or more equipment chambers can be positioned in other or additional locations in the medical kiosk. As also can be appreciated, some or all of the equipment chambers can be absent doors. The door on one or more of the equipment chambers can be designed to be unlocked and/or opened remotely by the medical provider and/or medical attendant; however, this is not required. The doors can be designed to automatically lock closed when the doors are closed by the medical attendant and/or medical provider after the user/patient has left the medical kiosk; however, this is not required. Each of the equipment chambers can be designed to include a different piece of medical equipment, namely a stethoscope, an otoscope, a thermometer, a dermascope, a spirometer, and a pulse oximeter; however, other or additional equipment and/or materials can be included in one or more of the equipment chambers (e.g., wipes, blood sugar analyzer, tissue, band aide, gauze, urine sample container, medication, etc.). Alternatively, the equipment chambers can be used to store one or more integrated medical devices that can include, but are not limited to, the following integrated devices: a stethoscope to evaluate heart, lung and/or bowel sounds; a thermometer to record temperature; an otoscope to examine the ear drum, external ear canal, nasal passages, mouth and/or throat; pulse-oximeter to measure blood oxygen saturation and/or heart rate; a spirometer and transducer to measure the volume of air inspired and/or expired by the lungs; an audiometer to test hearing; a 3-lead EKG to provide a snapshot of the heart rhythm and/or data regarding stress and/or injury to the heart muscle; and/or a glucometer to measure blood glucose levels. As can be appreciated, other or additional medical devices can be included in the medical kiosk which are inside or outside of the expandable mounting system such as, but not limited to, a scale, lab-on-a-chip finger stick technology, blood analyzer (e.g., blood sugar analyzer, blood toxicity analyzer, blood oxygen content analyzer, etc.), height tape and others; however, this is not required. As can also be appreciated, a larger or smaller number of medical equipment can be used in the medical kiosk and/or different types of medical equipment can be included in the medical kiosk. The one or more equipment chambers can also or alternatively be used to include other types of material (e.g., tissue, gauze, disinfecting wipe, cotton ball, tongue depressor, tweezers, cortisone cream, urine sample container, etc.); however, this is not required. The one or more equipment chambers generally include a door to limit access to the one or more equipment chambers; however, this is not required. The door, when used, can be manually openable/closeable, and/or the doors can be controllably open/closed remotely by the medical provider or medical attendant; however, this is not required. The expandable mounting system for medical devices can be made of high-strength plastic or any other sufficiently rigid and strong material such as metal, wood, and the like. The configuration and/or size of each the equipment chambers can be the same or different. The one or more doors on the expandable mounting system can be manually opened and/or closed and/or remotely opened and/or closed by a medical provider and/or medical attendant. The one or more medical devices in the one or more chambers or bays can are activated/deactivated remotely by software and/or manually activated/deactivated. The one or more medical devices in the one or more chambers or bays can be connected to a connector in the chambers or bays so as to supply power to the medical device and/or to electronically transmit information between the medical device and a computer, network, storage device, etc. The expandable mounting system can include one or more visual indicators (e.g., light, etc.) to indicate to a user/patient which chamber is to be used and/or is active. A medical attendant and/or medical provider can be used to assist the patient in the operation of one or more medical devices; however, this is not required.

In still yet another and/or alternative non-limiting aspect of the invention, the novel method and apparatus for providing medical services, diagnoses, health, and/or wellness advice to individuals can include digital signage on the exterior of the medical kiosk; however, this is not required. The digital signage, when used, can be displayed through one or more monitors or display screens on the exterior and/or interior of the medical kiosk to able a user/patient/potential user to see one or more of the monitors or display screens. One non-limiting aspect of this invention is that the one or more monitors or display screens can be used to display advertisements that may be arranged by the originating site; however, this is not required. Another non-limiting aspect of this invention is that one or more of the monitors or display screens can be used to display the current wait time for the medical kiosk and/or the list of scheduled appointments; however, this is not required. The digital signage application can allow various companies to advertise via the medical kiosk, including the business where it is located; however, this is not required. The digital signage application can be tailored to display information for specific patients based upon their conditions; however, this is not required. The digital signage application can include the ability to display a scrolling message at the bottom of the screen, based upon the business's preference; however, this is not required. The one or more display screens and/or monitors can be used to provide various types of information (e.g., registration information, information input by the user, advertising information, information about the medical kiosk, information about wait time for a medical kiosk, information as to the order of users waiting to use the medical kiosk, information about whether a medical kiosk is available or in use, cable TV, satellite TV, local broadcast TV, infomercial, medical programs, DVD materials, Blu-ray materials, etc.). Patients waiting to enter the medical kiosk can be allowed to view the various advertisements and/or other types of information displayed on the one or more screens; however, this is not required. The patients can see the wait time for their appointment and/or their position in the appointment queue when such information is displayed on the one or more video screens; however, this is not required. Any message necessary for the patient to see can also be displayed upon the screen in the interior of the medical kiosk; however, this is not required (e.g., "Welcome (Patient Name)", "Your Medical Provider (Provider Name) Will Begin Your Visit Once You Have First Captured Some Basic Vitals", etc.). The one or more interior screens are primarily utilized for video conferencing between the patient and the provider, patient data input, and patient instructions, but can also be used to display advertisements and/or other information during periods where the medical kiosk has no appointment queued; however, this is not required. The digital signage application can allow businesses to display advertisements and/or current promotions in a way that will attract the consumer's attention; however, this is not required. The ability to tailor the signage to individual patients and/or population groups makes it very adaptable; however, this is not required. The information on the display can be any language. The information on the display can include subtitles, etc.; however, this is not required.

In another and/or alternative non-limiting aspect of the invention, the novel method and apparatus for providing medical services, diagnoses, health, and/or wellness advice to individuals can include an exterior check-in registration station via an integrated touch screen monitor; however, this is not required. The novel method of the present invention can include the use of a medical kiosk to enable the patient to conveniently communicate with the medical provider. In one non-limiting embodiment, the medical kiosk has an exterior check-in registration station. The check-in registration station can include a key pad and/or key board for identification and/or data entry, a touch screen for identification and/or data entry, microphone and/or voice recognition software for identification and/or data entry, fingerprint scanner for identification and/or data entry, and/or retina scanner for identification and/or entry; however, this is not required. As can be appreciated, other or additional devices can be included on the medical kiosk for identification and/or data entry. The medical kiosk having an exterior check-in registration station can be used by the patient to enter/convey basic information about the patient. Such information includes, but is not limited to, a) patient name, b) patient address, c) patient contact information, d) patient age, e) patient sex, f) patient height, g) patient weight, h) patient medical history, i) current medicines used by patient, j) reason(s) for visit by patient, k) patient current symptoms, l) patient insurance information, m) patient payment information, n) consent forms, and/or o) patient's current doctor. As can be appreciated, other or additional information can be inputted/conveyed by the patient. The medial kiosk can be designed to provide information to the patient prior to and/or during the inputting/conveying of information by the patient to the medical kiosk. In one non-limiting embodiment of the invention, the medical kiosk can include audio and/or visual instructions and/or displays used to provide a) information about the medical kiosk, b) how to use the medial kiosk, c) how to properly input/convey information to the medical kiosk, d) provide instructions and/or interactions with the patient during the inputting/conveying of information by the patient to the medical kiosk, e) the wait time for the patient's use of the medical kiosk, f) a list of patient's waiting to use the medical kiosk, and/or g) information regarding whether the medical kiosk is in use or is available. In another and/or alternative non-limiting embodiment of the invention, the medical kiosk can include light and/or sound indicators to provide information regarding whether the medical kiosk is in use or is available; however, this is not required. In still another and/or alternative non-limiting embodiment of the invention, the medical kiosk can include a notification system to a patient that the medical kiosk is available or will soon be available; however, this is not required. Such notification can be sent via email, phone, pager, internet, etc. Such notification system can be useful when the medical kiosk is not currently available to the patient. The patient can input the information into the medical kiosk and then go home, run other errands, etc., and then be later notified when the medical kiosk is available or will soon be available. The medical kiosk and/or notification system can also be used to inform the patient when and/or where other medical kiosks are available; however, this is not required. This service, when available, can be used to inform the patient that a nearby medical kiosk has a shorter wait period or is currently available, thus providing the patient with the option of traveling to another available medical kiosk instead of waiting for the current medical kiosk to become available; however, this is not required. This service, when available, can also be used to inform the patient when a prescription is ready for pickup and/or for conveying prescription information to the patient; however, this is not required. This service, when available, can also be used to inform the patient when a follow-up visit is due and/or scheduled; however, this is not required. As can be appreciated, the notification system can be used for other or additional services. The medical kiosk can include an exterior registration station for check-in via a touch-screen monitor (e.g., monitor, etc.). The touch-screen monitor can be mounted at a height and angle that meets ADA compliance and is easily accessible to individuals in wheel chairs; however, this is not required. The touch-screen monitor can include a built in privacy filter for HIPAA compliance; however, this is not required. In one non-limiting embodiment, the front panel of the medical kiosk includes a registration station. The registration station can include a touch screen, a display screen, and an optional frame that such components can be mounted thereto; however, this is not required. The shape of the frame, when used, is non-limiting. The frame, when used, can be designed to be easily removed from the front panel to enable servicing, repair, replacement, etc. of one or more components of the registration station; however, this is not required. As can be appreciated, the registration station can also or alternatively include other or optional features (e.g., additional display screen, additional touch screen, lights, buttons, switches, camera, speakers, microphone, keyboard, scanner, receiver, transmitter, credit card/debit card or other some other card reader, smart phone or other smart device reader/scanner, finger and/or eye scanner, shelf, printer, storage cavity, service access door, motion sensor, sound sensor, temperature sensor, logos, etc.); however, this is not required. The touch screen, when used, is generally used to allow a user to enter in information about the user (e.g., age, sex, contact information, payment information, medical history, medical issue, etc.); however, this is not required. The touch screen can be substituted for a keyboard; however, this not required. The frame can be designed to mount the touch screen at some angle (e.g., 10-80°) relative to the front plane of the front panel; however, this is not required. The frame optionally includes one or more side sections that can include one or more other or optional features of the registration station; however, this is not required. As can be appreciated, one or more other or optional features of the registration station can also or alternatively be located on other regions of the registration station. The touch screen can display various types of information (e.g., electronic keyboard, instructions on how to register, questions that are displayed during registration, instructions during registration, information displayed to user during registration, various templates, various menus, various lists of information, etc.); however, this is not required. As can be appreciated, the medical kiosk can be designed to accept voice commands during the registration process; however, this is not required. The display screen can be used to provide various types of information (e.g., registration information, information input by the user, advertising information, information about the medical kiosk, information about wait time for a medical kiosk, information as to the order of users waiting to use the medical kiosk, information about whether a medical kiosk is available or in use, cable TV, satellite TV, local broadcast TV, infomercial, medical programs, DVD materials, Blu-ray materials, etc.). Another display screen can be positioned above the screen used at the registration station and/or at some other location on the exterior of the medical kiosk; however, this is not required. This other display screen can be used to display various types of information (e.g., advertising information, information about the medical kiosk, information about wait time for a medical kiosk, information as to the order of users waiting to use the medical kiosk, information about whether a medical kiosk is available or in use, cable TV, satellite TV, local broadcast TV, infomercial, medical programs, DVD materials, Blu-ray materials, etc.); however, this is not required. In one non-limiting arrangement, the screen used at the registration station and the one or more other displays can be design to display different types of information (e.g., screen used at the registration station displays information related to the registration process and the one or more other displays are used to display one or more types of information that are different from the information displayed on the screen used at the registration station, etc.); however, this is not required. The size of the screen used at the registration station and the one or more other displays can be the same or different. In one non-limiting arrangement, a user/patient can be allowed to enter payment information at the registration station (e.g., swipes a credit or debit card, etc.); however, it can be appreciated that payment information can also or alternatively be entered inside the medical kiosk, at the optional attendant station, wirelessly or over a network via a smart phone or other device or by a computer connected to a network, etc. If a medical attendant is available, the medical attendant can assist a user during the registration process; however, this is not required. Generally, the medical kiosk includes a single registration station; however, this is not required. As can be appreciated, the registration station can alternatively be located inside the medical kiosk, at the attendant station, on other panels or sidewalls of the medical kiosk, or located remotely from the medical kiosk (e.g., central registration center for use with multiple medical kiosks, etc.). In one non-limiting arrangement, the exterior check-in registration station can be designed to be easily removed from the front panel of the medical kiosk and/or be easily access from the interior of the medical kiosk to enable servicing, repair, replacement, etc. of one or more components of the registration station; however, this is not required. The check-in system in accordance with the present invention offers a new way for organizations to meet rising consumer expectations for convenience and at the same time improve accuracy and usability of information systems; however, this is not required. The check-in system in accordance with the present invention can result in shorter waiting times for check-in, as well as efficiency gains from increased throughput and fewer errors in keeping patient demographic data up to date; however, this is not required. The check-in system in accordance with the present invention can result in the reduction of risk of patient misidentification and clerical errors at data entry; however, this is not required. The check-in system in accordance with the present invention can improve accuracy in language access for those not fluent in English by offering multiple language options during the check-in process; however, this is not required.

In still another and/or alternative non-limiting aspect of the invention, the novel method and apparatus for providing medical services, diagnoses, health, and/or wellness advice to individuals can include a sanitizing system (e.g., UV system, mist system, etc.) that can be automatically activated and/or activated by the medical attendant and/or medical provider prior to and/or after a patient has used the medical kiosk; however, this is not required. The medical kiosk can include a cleaning system designed to clean the interior of the medical kiosk and/or kill/neutralize some of or all germs and/or other micro-organisms in the medical kiosk; however, this is not required. One non-limiting cleaning system that can be used is an ultraviolet sanitizing system. As can also be appreciated, a mist sanitizer can also or alternatively be used to fully or partially clean/sanitize one or more portions of the medical kiosk. As can be appreciated, other or additional cleaning systems can be used. In another and/or alternative non-limiting aspect of the invention, the medical kiosk can be made of one or more materials that resist growth of bacteria, viruses and/or other micro-organisms; however, this is not required. In one non-limiting embodiment, the floor, walls and ceiling of the medical kiosk include or are fully made of materials that resist or prevent the growth of bacteria, viruses and/or other micro-organisms; however, this is not required. In one non-limiting arrangement, the medical kiosk includes an ultraviolet light sanitization system which can be used in the medical kiosk and which can be activated through software from a remote location and/or by a kiosk attendant; however, this is not required. The ultraviolet light sanitization system can be activated twice daily to ensure the sanitary environment is maintained; however, it can be appreciated, that the ultraviolet light sanitization system can be activated a greater or lesser number of times per day. The location of the ultraviolet light sanitization system, when used, is non-limiting. In one non-limiting arrangement, the ultraviolet light sanitization system can be located in the roof or ceiling of the medical kiosk; however, this is not required. For example, the ultraviolet light sanitization system can be connected or positioned adjacent to the ceiling panel and rear panels; however, this is not required. The ultraviolet light sanitization system can be located in the rear of the medical kiosk where it will be out of the way of the patients utilizing the medical kiosk; however, this is not required. The ultraviolet light sanitizing system generally includes one or more ultraviolet lights that are designed to kill some or all of the germs and/or other micro-organisms in the medical kiosk. The ultraviolet sanitizing system can optionally include one or more vents that allow air to flow into and/or out of the ultraviolet sanitizing system to facilitate in the cooling of the ultraviolet sanitizing system; however, this is not required. The sanitization system can be built with high-strength plastics and/or any other sufficiently rigid and strong material such as metal and constructed in a way preventing it from being tampered with by patients or anyone other than the attendant; however, this is not required. Such an arrangement, when used, can facilitate in ensuring that it is not activated incorrectly or at an inopportune time; however, this is not required. The shape, size and/or configuration of the built in sanitization system are non-limiting. The one or more medical attendants, when used, can also or alternatively clean and/or sanitize various regions of the medical kiosk prior to and/or after being used by a patient and/or set up the medical kiosk for a new user; however, this is not required. For example, prior to and/or after one or more patients have entered the medical kiosk, the one or more attendants can clean/sanitize one or more exterior surfaces and/or regions of the medical kiosk (e.g., medical kiosk door, medical kiosk check-in terminal, medical kiosk desk top, medical kiosk exterior walls, medical kiosk touch screen, medical kiosk monitors, seating/tables in waiting area near medical kiosk, etc.); however, this is not required. In an another and/or additional example, prior to and/or after one or more patients have entered the medical kiosk, the one or more medical attendants can clean/sanitize one or more interior surfaces of the medical kiosk (e.g., medical kiosk door, medical kiosk floor, medical kiosk bench, medical kiosk chair, medical kiosk user terminal, medical kiosk interior desk top, medical kiosk interior walls, medical kiosk touch screen, medical kiosk monitors, medical kiosk instrument doors, medical devices/instruments used by and/or touched by user when in the medical kiosk, any other surface in the interior of the medical kiosk, etc.); however, this is not required. In still another and/or additional example, prior to and/or after one or more patients have entered the medical kiosk, the one or more medical attendants can set up the medical kiosk for a user (e.g., clean/sanitize interior surfaces of medical kiosk; clean/sanitize medical devices/instruments used and/or touched by a prior user; reposition medical devices/instruments into device storage areas; replace disposable components on medical devices/instruments; fix, repair and/or replace fans, UV bulbs, UV devices, etc. in the interior and/or exterior of the medical kiosk; refill cleaning and/or sanitizing fluid; etc.); however, this is not required. In still yet another and/or alternative non-limiting aspect of the invention, the medical kiosk can include a sanitizing system (e.g., UV system, mist system, etc.) that can be automatically activated and/or activated by the medical attendant prior to and/or after a patient has used the medical kiosk; however, this is not required. As can also be appreciated, a mist sanitizer can also or alternatively be used to fully or partially clean/sanitize one or more portions of the medical kiosk. Generally the germs and/or other micro-organisms in the medical kiosk are treated when the interior of the medical kiosk does not include a user. The sanitizing system can optionally include one or more standard lights that can be used to provide illumination in the medical kiosk; however, this is not required. The sanitizing system can optionally include a cooling fan for the one or more components in the sanitation system; however, this is not required. The sanitizing system can optionally include both a UV and a mist sanitizing system; however, this is not required. The sanitizing system can house one or more cameras, speakers, sensors (e.g., temperature sensor, motion sensor, sound sensor, etc.), etc. for use in the medical kiosk; however, this is not required. The sanitizing system includes a shroud that includes vent/light/mist openings to house the components of the sanitizing system; however, this is not required. The shape, size and configuration of the shroud, when used, are non-limiting. When a mist sanitizing system is additionally or alternatively used, one or more mist nozzles can be located in one or more regions of the medical kiosk so as to direct the sanitizing mist to desired locations in the medical kiosk; however, this is not required. The doors to the medical kiosk can be closed and/or locked to prevent a user/patent from entering the medical kiosk during a sanitizing process; however, this is not required.

In yet another and/or alternative non-limiting aspect of the invention, the novel method and apparatus for providing medical services, diagnoses, health, and/or wellness advice to individuals can include a medical kiosk that enables a service operator to easily access the various components of the medical kiosk for purposes of service, repair, maintenance, upgrade, replacement, etc. In order to offer the comprehensive services the medical kiosk is capable of, there are multiple components that must be functioning at all times. The various devices that may need service include, but are not limited to, the display screens, the network connection, various other electronics and wiring, fans, lights, electronic switches, backup power supplies, computers, electronic storage devices, doors on the medical equipment compartments, etc. The ability to easily and conveniently access and/or performing maintenance on these components is advantageous to providing the medical kiosk services via the medical kiosk; however, this is not required. To more easily facilitate the service of these components, the medical kiosk can be designed with a moveable front panel; however, this is not required. The front panel can be built on casters, wheel, rail system, etc. to allow the front panel to be easily moved; however this is not required. The front panel can be equipped with a tamper proof lock to prevent unauthorized personnel from accessing the components located behind the front panel; however, this is not required. A portion or the entire front panel can be designed to move in order to ensure that when there is a problem with one or more components used in the medical kiosk, the repair of such components does not require the disassembly of the entire or a substantial portion of the medial kiosk to repair the components; however, this is not required. The components of the medical kiosk that are generally difficult or inaccessible when the medical kiosk is fully assemble are 1) the components that form the exterior check-in station, 2) the interior displays or monitors, 3) the interior speakers, the interior cameras, 4) the interior sound jack, 5) the doors on the medical compartments, 6) the interior microphone, 7) the electronics located behind the exterior check-in station, 8) the electronics located behind the interior AV system, and/or 9) the computer and other electronics used for network communication, control and/or storage; however, this is not required. As can be appreciated, there may be other or additional components of the medical kiosk that are generally difficult or inaccessible when the medical kiosk is fully assembled. Access to one or more of these components can be more easily accessed by the movement of the interior front panel of the medical kiosk; however, this is not required.

In still yet another and/or alternative non-limiting aspect of the invention, the novel method and apparatus for providing medical services, diagnoses, health, and/or wellness advice to individuals can include a method and a medical kiosk that enables the medical provider to generate electronic prescriptions and/or for the patient to conveniently select and/or order prescription drugs; however, this is not required. In one non-limiting embodiment, this novel method and apparatus will allow patients to 1) choose between name brand and generic drugs, 2) choose the supply quantity for the prescription (i.e., 30 days supply, 60 days supply, 90 days supply, etc.), 3) choose between picking the prescription up at the pharmacy of their choice or mail delivery of the prescription, 4) enter medical insurance for partial or full payment of the prescription, 5) enter a credit or debit card information to pay for the prescription, 6) enter information for mail delivery of the prescription, 8) enter information to provide automatic reminders to patient regarding refilled and/or follow-up medical visits, 9) enter information to enable a patient to be notified when a prescription has been mailed and/or is ready to be picked-up at the pharmacy; however, this is not required, 10) obtain a print out and/or electronic version of the prescription written by the medical provider, and/or 11) receive information about the issued prescription (e.g., prescribed use, side effects, etc.) in printout and/or electronic form; however, this is not required. Another non-limiting aspect of this method and apparatus will allow the patient to select the select the pharmacy where he/she would like to pick-up the prescription; however, this is not required. In one non-limiting embodiment of the invention, the medical provider can generate an electronic prescription for a patient. The prescription can include both the generic and name brand drugs along with the patient copay amount for each; however, this is not required. The electronic prescription can provide additional information (e.g., potential savings for selecting certain medications, the dosage amount, the medication dosage, quantity or strength, name of medical provider, help information, etc.), advertising information, etc.; however, this is not required. Once the particular medication brand is selected by the patient, another screen can optionally appear; however, this is not required. For example, the second screen can illustrate the brand of medication selected by the patient/user and/or also provides quantity supply options for the medication, etc.; however, this is not required. The second screen can optionally illustrated additional information such as, but not limited to, the copay amount for the selected medication brand and quantity, the monthly, yearly, etc. savings for selecting a particular medication brand and/or quantity, help information, go back option, advertising information, etc.; however, this is not required. The second or a third screen can optionally appear that provides an order confirmation along with the associated savings; however, this is not required. The second or third screen can optionally illustrate additional information such as, but not limited to, the monthly, yearly, etc. savings for selecting a particular medication brand and/or quantity, help information, advertising information, etc. As can be appreciated, other or additional screens can be displayed to the user/patient. This aspect of the invention has the advantage of allowing the user/patient to view and/or select brand or generic drugs thereby allowing the user/patient to decide which drug option is best for them and their budget; however, this is not required. The medical kiosk and method for using the medical kiosk can thus include a point of purchase prescription workflow application allowing a medical provider to generate prescriptions and optionally allowing patients to select and/or order prescription drugs; however, this is not required. The medical kiosk and method for using the medical kiosk can include a point of purchase prescription workflow application that allows a user/patient to choose his/her drug brand and/or quantity; however, this is not required. The medical kiosk and method for using the medical kiosk can include a point of purchase prescription workflow application that allows a user/patient to select the pharmacy from which to pick up his/her prescription; however, this is not required.

In another and/or alternative non-limiting aspect of the invention, the novel method and apparatus for providing medical services, diagnoses, health, and/or wellness advice to individuals can include headphone jacks. The one or more headphone jacks allow for hearing impaired patients to utilize headphones in order to better understand the provider's instructions; however, this is not required. The one or more headphone jacks can also be used to enable additional persons in the medical kiosk (e.g., child's parent, etc.) to listen in on the conversation between the medical provider and patient; however, this is not required. The one or more headphone jacks can also be used to provide additional privacy between the medical provider and patient; however, this is not required. The headphones may be available from the kiosk and/or the medical attendant; however, this is not required. The headphone jack can be placed at a height allowing any person to reach it if necessary; however, this is not required. The headphones generally will be sanitary either through disposable covers or through another form of sanitization; however, this is not required. The headphone jack can be a standard jack to enable a patient to use his/her own headphone; however, this is not required. The medical kiosk can include a wireless system (e.g., Bluetooth technology, IR technology, RF technology, etc.) to transmit sound wirelessly to a patient and/or other person located in the medical kiosk; however, this is not required. The kiosk can also be equipped with a wheelchair accessible ramp; however, this is not required. The medical kiosk can be designed to be fully ADA compliant as a result of these novel innovations; however, this is not required. A medical kiosk that includes one or more headphone jacks and/or a wheelchair accessible ramp can permit the medical kiosk to better serve the public at large; however, this is not required.

In still another and/or alternative non-limiting aspect of the invention, the novel method and apparatus for providing medical services, diagnoses, health, and/or wellness advice to individuals can include a medical kiosk that utilizes high definition video and/or high quality sound to create a conference link between a patient located in the medical kiosk and a medical provider that is located remotely to the medical kiosk. In one non-limiting aspect of the invention, the medical kiosk includes the use of one or more high definition cameras, one or more high definition monitor(s) and/or high quality speaker(s) built into the medical kiosk; however, this is not required. The one or more cameras located within the medical kiosk can be on an adjustable sliding bar allowing camera positioning to create ideal eye contact; however, this is not required. The one or more cameras in the medical kiosk can be used to enable a medical provider to obtain information about a user/patient in the medical kiosk (e.g., height, build, sex, skin color, alertness, body cuts, body infections, body rashes, pupil dilation, hygiene, race, physical condition, emotional condition, metal condition, etc.); however, this is not required. In one non-limiting arrangement, one or more monitors and/or display screens can be positioned on the front interior wall of the medical kiosk; however, this is not required. The monitor is generally used to view the one or more medical providers when the user/patient is located in the medical kiosk; however, this is not required. The shape, size, and thickness of the one or more monitors are non-limiting. One or more cameras can be positioned on the front interior wall, be embedded in the one or more monitor/display screens, and/or be located on a sliding bar allowing it to be positioned relative to the user/patient to create better eye contact with the user/patient in the medical kiosk; however, this is not required. The one or more cameras enable pictures of the user/patient in the medical kiosk to be transmitted to a remotely located medical provider; however, this is not required. The remotely located provider typically has a camera at his/her location so that pictures of the medical provider can be transmitted to the one or more medical screens in the medical kiosk; however, this is not required. As can be appreciated, a projector can be used as a substitute of one or more monitors in the medical kiosk; however, this is not required. One or more speakers can be positioned on the front interior wall of the medical kiosk; however, this is not required. As can be appreciated, one or more speakers can be positioned on other or additional locations in the medical kiosk; however, this is not required. The speakers can be used to enable a user/patient in the medical kiosk to listen to what the medical provider is saying to the user/patient; however, this is not required. One or more microphones are generally included in the medical kiosk to allow the user/patient to communicate with the medical provider; however, this is not required.

In yet another and/or alternative non-limiting aspect of the invention, the novel method and apparatus for providing medical services, diagnoses, health, and/or wellness advice to individuals can include a medical kiosk that is modular kiosk that is able to be partially or fully broken down; however, this is not required. In one non-limiting embodiment of the invention, the modular medical kiosk can be partially or fully broken down so as to fit through a doorway (e.g., standard 36" by 80" doorway, etc.); however, this is not required. The modular design of the medical kiosk can enables the medical kiosk to be set up in various configurations to enable the medical kiosk to be used in various types of spaces; however, this is not required. The modular design of the medical kiosk can be designed to not only accommodate multiple configurations of the medical kiosk, but can also be designed to facilitate in enabling the medical kiosk to be moved into an existing facility and then allowing the assembly of the medical kiosk in such facility without having to modifying the entry ways into or out of the facility; however, this is not required. The medical kiosk can be formed of any number of materials (e.g., plastic, foam, metal, wood, etc.). The modular configuration of the medical kiosk can be such that it can be easily assembled and disassembled so that the medical kiosk can be easily brought into a location and easily set up; however, this is not required. The medical kiosk can be designed to include a floor panel; however, this is not required. The floor panel, when used, is generally a one piece unit; however, the floor panel can be formed of multiple pieces. The floor panel, when used, can be formed of a durable material (e.g., plastic, metal, wood, composite material, man-made materials, etc.). The floor panel, when used, can be formed of a slightly compressible material to facilitate in the comfort of walking on the floor panel; however, this is not required. The floor panel can have an oval shape; however, other shapes can be used (e.g., circular, square, rectangular, polygonal, etc.). In one non-limiting design, the maximum length of the floor panel is generally 3-15 feet, typically 4-12 feet, more typically about 6-10 feet, and even more typically about 8-9 feet; however, other lengths can be used. In one non-limiting design, the maximum width of the floor panel is generally 3-10 feet, typically 4-8 feet, and more typically about 4-6 feet; however; other widths can be used. In one non-limiting design, the top surface area of the floor panel is generally 10-150 sq. ft., typically 15-80 sq. ft., and more typically about 50-60 sq. ft.; however, other surface areas of the floor panel can be used. The floor panel can be sized to enable a user in a wheelchair to enter the medical kiosk and turn and/or fully maneuver in the medical kiosk while sitting in the wheelchair; however, this is not required. In one non-limiting design, the thickness of the floor panel is generally about 0.1-5 inches, and typically about 0.25-3 inches; however, other thicknesses of the floor panel can be used. A ramp can be optionally used to facilitate entry and exiting of the medical kiosk; however, this is not required. The shape and size of the ramp are non-limiting. The ramp can be made of a similar material as the floor panel; however, this is not required. The ramp generally includes a sloped surface to facilitate in transitioning from a floor surface to the top surface of the floor panel; however, this is not required. The medical kiosk can optionally include one or more benches, stools and/or chairs. When a bench is included in the medical kiosk, the bench is generally positioned on the back interior wall of the medical kiosk; however, this is not required. The bench can be used to allow a parent, guardian, spouse, relative, friend, etc. to sit in the medical kiosk while the user is obtaining medical services in the medical kiosk. The bench can be designed to enable one or more persons to sit on the bench. The bench can optionally include a storage space under the seat of the bench that can be used to store supplies, equipment, etc. for the medical kiosk. A liftable seat section can be used to access the storage space; however, this is not required. When the bench includes a storage space, the bench can include a lock to limit access to the storage space; however, this is not required. As can be appreciated, the medical kiosk can include one or more chairs, not shown, to enable one or more users to sit in the medical kiosk while receiving medical services in the medical kiosk; however, this is not required. The bench is generally about 10-25 inches high, and typically about 16-20 inches high; however, other heights can be used. In one non-limiting arrangement, the medical kiosk can include two front panels, two rear panels, one side wall, and one door system; however, this is not required. The front panels, rear panels, side wall, and door system are generally formed of a durable material (e.g., plastic, metal, wood, composite material, man-made materials, etc.). As can be appreciated, the medical kiosk can be designed to only include a single front panel and/or a single rear panel. As can also be appreciated, the medical kiosk can be designed to include more than two front panels and/or more than two rear panels. As can be appreciated, the medical kiosk can be designed to include more than one side wall and/or more than one door system. As can also be appreciated, a side wall can be substituted for another door system; however, this is not required. The general shape and size of the front and rear panels are the same; however, this is not required. The shape of the front and rear panels can be arcuate; however, this is not required. The radius of curvature the front and rear panels can be about 10-100 inches, typically 15-50 inches, and more typically about 20-35 inches; however, other radius of curvatures can be used. The front and rear panels can have an angle of curvature of about 90° or a quarter of a circle; however, it can be appreciated that one or both rear and/or front panels can have different angles of curvature. The general shape and size of the side wall and the door system are generally the same; however, this is not required. The side wall and door system can lie in a generally flat plane; however, this is not required. The front and rear panels and the side wall and door system can form a generally oval shape for the medical kiosk; however, this is not required. The two front panels and two rear panels can have the same or similar footprint; however, this is not required. The side wall and the door system can have the same or similar footprint; however, this is not required. The similarity in the shape and footprint of the wall components of the medical kiosk, when used, enables the medical kiosk to be assembled in a manner that is convenient for the facility that will include the medical kiosk. For example, if the door system needs to be positioned on the left side of the medical kiosk, instead of the right side, the similarly shaped side wall and door system enables the medical kiosk to be assembled in such a manner. Also, if the optional registration station of the medical system needs to be placed on the left side or right side or on the rear end of the medical kiosk instead of the front end, the similarly shaped front and rear panels can be easily exchanged to create such configuration for the medical kiosk. The modular medical kiosk not only accommodates multiple configurations of the medical kiosk, it also can facilitate in enabling the medical kiosk to be moved into an existing facility and then assembling the medical kiosk in such facility without having to modify the entryways into or out of the facility; however, this is not required. The thickness and height of the front panels, rear panels, side wall and door system are non-limiting. In one non-limiting embodiment, the maximum height of the front panels, rear panels, side wall and door system is about 5-12 ft., typically about 6-9 ft., and more typically about 7-8 ft.; however, other heights can be used. In one non-limiting embodiment, the thickness of the front panels, rear panels, side wall and door system is generally about 0.5-10 inches, typically about 1-5 inches, and more typically about 1-2 inches; however, other thicknesses can be used. The front panels, rear panels, side wall and door system can optionally include insulation, sound dampening material, etc.; however, this is not required. The front panels, rear panels, side wall and door system can be designed to be connected together in a variety of ways (e.g., bolted/screwed together, latched together, snap fitted together, press fitted together, etc.). Generally, the arrangement is used to connect together the front panels, rear panels, side wall and door system is selected to enable easy connecting and disconnecting of the front panels, rear panels, side wall and door system from one another. One or more of the front panels, rear panels, side wall and door system can include openings, windows, transparent/semi-transparent regions that allow for ventilation, illumination, and/or viewing; however, this is not required. Generally, front panels, rear panels, side wall and door system are mostly or fully formed of opaque or non-transparent materials so as to ensure the privacy of the user in the medical kiosk; however, this is not required. The configuration of the door system is non-limiting. The door system can include a frame and two doors; however, it can be appreciated that the door system only includes a single door. Each door can include a handle or grasp cavity on one or both sides of the one or both doors. The one or more doors can be designed to open and close in a variety of ways (e.g., swing open and closed, slide open and closed on a top/bottom rail system, etc.). As can be appreciated, the one or more doors for the medical kiosk can also or alternatively be positioned on one or more of the front or rear panels; however, this is not required. In one non-limiting embodiment, the maximum height of the doors is generally about 5-9 ft., and typically about 6-7 ft.; however, other heights can be used. In one non-limiting embodiment, the maximum width of the entry provided by the one or more doors when fully open is generally about 15-60 inches, typically about 25-55 inches, and more typically about 30-50 inches; however, other widths can be used. The door opening is generally selected to enable a standard wheelchair to pass through the opening; however, this is not required. The medical kiosk can optionally include an exterior attendant station that is connected to and/or positioned near the medical kiosk. The exterior attendant station can be used by one or more medical attendants, medical providers, etc. A desk can be connected to and/or positioned next to an exterior wall of the medical kiosk; however, this is not required. The desk, when used, can be formed of one or more pieces. When the desk is designed to be connected to an exterior wall of the medical kiosk, such connection arrangement is not limited (e.g., screw, bolt, clamp, press fit, snap arrangement, etc.). The desk can include a desk top, one or more legs, one or more shelf regions, one or more drawers, etc.; however, this is not required. One or more chairs, not shown, can be used to allow one or more medical attendants, medical providers, etc. to sit at the desk; however, this is not required. The desk, when used, can be positioned at or adjacent to one or both front panels; however, this is not required. The desk can be designed to include one or more drawers, shelves, doors, etc. One or more locks can be included on the desk; however, this is not required. The desk can be used to support a monitor, computer, power supply, power strip, printer, router, network switcher, key board, mouse, printer paper, medical supplies, sanitation supplies, refrigerator, freezer, scanner, credit card/debit card reader, data port, lights, desk supplies, etc. The freezer and/or refrigerator, when used, can contain immunizations, medications, urine samples, blood samples, etc.

In still yet another and/or alternative non-limiting aspect of the invention, the novel method and apparatus for providing medical services, diagnoses, health, and/or wellness advice to individuals can include a medical kiosk that includes a ceiling panel. The ceiling panel can be formed of one or more pieces. The ceiling panel can be formed of a transparent or semi-transparent material to allow light to enter and illuminate the interior of the medical kiosk; however, this is not required.

In still yet another and/or alternative non-limiting aspect of the invention, the novel method and apparatus for providing medical services, diagnoses, health, and/or wellness advice to individuals can include a medical kiosk that is made of one or more materials that resist or prevent the growth of bacteria, viruses and/or other micro-organisms; however, this is not required. In one non-limiting embodiment, the floor, walls and ceiling of the medical kiosk include or are fully made of materials that resist or prevent the growth of bacteria, viruses and/or other micro-organisms; however, this is not required.

In still another and/or alternative non-limiting aspect of the invention, the novel method and apparatus for providing medical services, diagnoses, health, and/or wellness advice to individuals can include a medical kiosk that includes a payment center that enables a user to pay for medical services, prescriptions, medical equipment, medical accessories, etc. prior to and/or after the user uses the medical kiosk; however, this is not required. The payment center can be in any form (e.g., credit card reader, mobile phone scanner, transmitter/receiver device, electronic scanner, cash receiver, etc.). The payment center may include a touch pad, key board, scanner, receiver, transmitter, credit card/debit card or some other card reader, smart phone or other smart device reader/scanner, finger and/or eye scanner, monitor, chair, table, shelf, printer, instructions on how to use the payment center, etc. The payment center can be located on the exterior and/or interior of the medical kiosk. Generally, the user is required to register and pay for the medical services prior to obtaining medical services from the medical provider; however, this is not required. In one non-limiting arrangement, the medical kiosk includes a registration station on the exterior of the medical kiosk (e.g., exterior wall of the medical kiosk, on a table exterior to the medical kiosk, etc.); however, this is not required. As can be appreciated, a user can be allowed to wirelessly connect to the medical kiosk or to some other computer network so as to wirelessly register and/or enter payment information for use of the medical kiosk; however, this is not required. In such an arrangement, a user could register to use a medical kiosk, enter in payment for use of the medical kiosk, set an appointment time for use of the medical kiosk, select a particular medical kiosk to use at some particular location, etc. at some location near or remote from the medical kiosk via a smart phone or other smart device, a computer, etc.

In yet another and/or alternative non-limiting aspect of the invention, the novel method and apparatus for providing medical services, diagnoses, health, and/or wellness advice to individuals can include a medical kiosk that includes an interior cavity or room that provides privacy to the patient when inputting and/or conveying data to the medical kiosk, and/or communicating with a medical provider via an audio and/or video link. The size, configuration and/or arrangement of the interior cavity or room are non-limiting. The interior cavity or room can include a) one or more speakers, b) one or more microphones, c) one or more video displays, d) one or more data input device, e) one or more chairs and/or other types of seating areas, f) one or more tables, g) one or more doors, h) one or more shelves, i) one or more compartments used to contain medical supplies, medical instruments, etc., j) one or more light switches, k) one or more power outlets, l) sterilization system, m) one or more headphone jacks, n) one or more lights, o) one or more table tops, p) one or more chair and/or benches, q) one or more doors, r) one or more windows, s) walls, floor and/or ceiling, t) one or more vents, u) one or more power outlets, v) one or more light and/or power switches, w) one or more USB and/or data connection outlets, and/or x) one or more fans. As can be appreciated, the interior cavity or room can include other or additional items. The size and configuration of the interior cavity or room can be designed to enable wheelchair access and maneuvering inside the interior cavity or room; however, this is not required. For example, the interior cavity or room can be designed to enable a standard wheelchair to move 90°, 180° and/or 360° while in the medical kiosk. The size and configuration of the interior cavity or room can be designed to provide sufficient room for the patient so that the patient can easily move within the interior cavity or room and/or the patient does not feel cramped or claustrophobic when in the interior cavity or room; however, this is not required.

In still yet another and/or alternative non-limiting aspect of the invention, the novel method and apparatus for providing medical services, diagnoses, health, and/or wellness advice to individuals can be designed to provide a convenient and low-cost structure (e.g., medical kiosk) that can be placed in many different locations, and which enable patients to conveniently access and obtain medical advice and/or care. Medical providers that are located locally or throughout the world can be used to communicate with the patient accessing the medical kiosk. As such, the medical services can be offered year around and at all times so long as there is a qualified medical provider somewhere in the world that is available and is qualified to provide medical assistance via the medical kiosk. Such an arrangement can be more convenient to the medical provider since the medical provider can work from home or from some other convenient location. The arrangement is also convenient to the patient since the patient can access medical assistance via the medical kiosk at the time and place of choosing. Indeed, in rural areas or smaller communities that do not have a local hospital or local doctor's offices nearby, the installation of a medical kiosk in the local drug store, department store, grocery store, etc., results in more accessible and timely medical care for patients in such communities. The costs associated with providing medical care via the medical kiosk may be less than if the patient seeks medical assistance from a hospital, clinic or doctor's office, thus resulting in the patient potentially saving money. As can be appreciated, other or additional advantages may exist by the method of the present invention.

In another and/or alternative non-limiting aspect of the invention, the novel method and apparatus for providing medical services, diagnoses, health, and/or wellness advice to individuals can include the use of a mobile device (e.g., smart phone, tablet, Ipad, Ipod, PDA, etc.) and/or computer (e.g., desktop computer, laptop computer, ultralight computer, etc.) to enable a patient to 1) conveniently locate an available medical kiosk, 2) schedule an appointment (e.g., date and/or time), 3) pre-register symptoms and/or reasons for visit, 4) set and/or cancel an appointment, 5) received reminders and/or updates regarding appoints, 6) obtain information about medical kiosk availability, 7) obtain information about certain medical provider availability, 8) obtain information about the available medical provider (e.g., name, specialty, etc.), 9) enable the selection of a certain medical provider and/or medical provider in a certain field of medicine, 10) obtain map information, address information and/or hours of operation information regarding selected medical kiosk, 11) locate closest kiosk and/or kiosk availability for a certain medical provider and/or medical provider in a certain field of medicine, 12) presubmit and/or preclear medical insurance, 13) submit payment information, 14) receive information on payment status, 15) receive information on insurance coverage, 16) receive appointment reminders and/or updates, 17) receive prescription information, 18) submit payment information for medical visit and/or prescription, 19) answer surveys regarding the use of the medical kiosk, and/or 20) receive medication reminders. The size, shape, configuration and look of the medical kiosk are non-limiting. In one non-limiting embodiment, this invention will allow patients to schedule appointments using a patient portal through a computer and/or mobile device; however, this is not required. Another non-limiting aspect of the application will allow the patient to select the kiosk location for their appointment. While selecting their appointment time and/or location, the patient can also fill out the symptom survey, select the time of their appointment, and/or select a physician if they choose; however, this is not required. The application can also allow the patient to receive appointment reminders via mobile device, text, phone, cell-phone, web-page, and/or email; however, this is not required. The application may also allow for patients to cancel or change their appointment; however, this is not required.

In still another and/or alternative embodiment of the invention, the novel method and apparatus for providing medical services, diagnoses, health, and/or wellness advice to individuals can include a mobile application for a portable device (e.g., smart phone, PDA, blackberry device, mobile note device, Ipad, Kindle device, Nook device, tablet device, etc.) and/or a computer based application (e.g., desktop computer, laptop computer, ultralight computer, etc.) that when launched gives the user a series of options that can include, but are not limited to, finding a medical kiosk (e.g., medical kiosk, etc.), set medication reminders, visit the home page of the medical kiosk operator, etc. As can be appreciated other and/or additional information can be included on the welcome screen of the mobile application and/or computer based application. The mobile application and/or computer based application can be designed to enable a user to 1) search or and/or locate medical kiosks in one or more communities, towns, cities, states, countries, etc.), 2) determine the distance a patient is from a medical kiosk, 3) obtain the directions to a medical kiosk, 4) to view the waiting status and/or availability of a particular medical kiosk, 5) obtain a map to the selected kiosk, 6) obtain information about the hours available for the medical kiosk, 7) obtain information about the actual location picture of the medical kiosk, 8) allow a user to make appointment with the medical kiosk, 9) provides information on the hospitals and/or medical providers associated with the medical kiosk, 10) provides information on which insurance carriers provide coverage for use of the medical kiosk, 11) obtain information on whether a particular medical provider is part of the medical kiosk network of medical providers, 12) obtain publics comments about the medical kiosk, 13) contact a helpdesk that provides information about the medical kiosk, 14) schedule an appointment (e.g., date and/or time), 15) pre-register symptoms and/or reasons for visit, 16) enter information required to create an appointment (e.g., personal information, date and time of appointment, particular medical kiosk, particular medical provider, insurance information, payments, ID verification, insurance card, etc.), 17) set and/or cancel an appointment, 18) receive reminders and/or updates regarding appoints, 19) obtain information about the available medical provider (e.g., name, specialty, etc.), 20) enable the selection of a certain medical provider and/or medical provider in a certain field of medicine, 21) locate closest kiosk and/or kiosk availability for a certain medical provider and/or medical provider in a certain field of medicine, 22) presubmit and/or preclear medical insurance, 23) submit payment information, 24) receive information on payment status, 25) receive information on insurance coverage, 26) receive appointment reminders and/or updates, 27) receive medication reminders, and/or 28) receive visit summaries; however, this is not required. In one particular non-limiting arrangement, the mobile application and/or computer based application enables a user to schedule an appointment at a medical kiosk. The creation of the appointment can be designed to enable the user to a) select the day and/or the time of the appointment, b) select a particular medical provider or type of medical provider (e.g., pulmonary doctor, gynecologist, etc.), c) provide a reason for visit and/or provide the user's symptoms, and/or d) set appointment and medication reminders; however, this is not required. As can be appreciated, other and/or additional information can be inputted by the user when making an appointment (e.g., sex, age, weight, height, medical history, use of current medications, symptom, allergies, etc.). The mobile application and/or computer based application can be designed to create an appointment confirmation screen along with text and/or email reminder options; however, this is not required. The confirmation screen, when provided, can provide information about the medical provider; however, this is not required. The confirmation screen, when provided, can be designed to enable the patient to change/cancel the appointment; however, this is not required. Several non-limiting advantages of the present invention include allowing a patient to decide which kiosk location is most convenient for the patient. The mobile application and/or computer based application may include an override for "first available" in regards to physician selection; however, this is not required. The patient also may be able to check availability of a preferred medical provider and/or the kiosk location; however, this is not required.

In yet another and/or alternative embodiment of the invention, the novel method and apparatus for providing medical services, diagnoses, health, and/or wellness advice to individuals can include a Provider Application wherein the medical provider can contact another medical provider during a patient visit if a special need or question arises during the patient visit wherein the medical provide believes and/or the patient request a second opinion and/or an opinion from a specialist; however, this is not required. The Provider Application can be designed to enable two or more medical providers to be simultaneously viewed and/or heard by the patient in the medical kiosk; however, this is not required. The Provider Application can be designed to allow only one medical provider at a time to be viewed and/or heard by the patient in the medical kiosk; however, this is not required. The Provider Application can be designed to allow an interpreter to appear to the medical provider and/or patient (e.g., language translator, sign language translator, etc.); however, this is not required. The Provider Application can be designed to allow a medical provide to contact another party (e.g., patient, guardian, relative, etc.) to obtain information, authorization, etc. about/for a patient using the medical kiosk; however, this is not required.

In still yet another and/or alternative embodiment of the invention, the novel method and apparatus for providing medical services, diagnoses, health, and/or wellness advice to individuals can include an administrator application allowing a medical administrator to remotely access one or more components of the medical kiosk; however, this is not required. The administrator application can optionally include one or more functions selected from the group consisting of 1) allowing remote access to one or more medical devices in the medical kiosk, 2) allowing remote access to one or more computers in the medical kiosk, 3) allowing remote access to one or more routers in the medical kiosk, 4) allowing remote access to one or more displays on the medical kiosk, 5) allowing remote access to one or more power supplies in the medical kiosk, 6) allowing remote access to one or more servers in the medical kiosk, 7) allowing remote access to one or more harddrives in the medical kiosk, 8) allowing diagnostics to be executed from a remote location on one or more electronic components in the medical kiosk (e.g., computer, router, server, battery backup, harddrive, medical devices, electronic locks, fans, displays, speakers, camera, headphone jack, electronic scale, Bluetooth devices, lights, pumps, scanners, touch pad, ID verification devices, printer, etc.), 9) allowing the rebooting and/or reinitializing from a remote location of one or more electronic components in the medical kiosk, 10) allowing for review of the current and/or past status from a remote location of one or more electronic components in the medical kiosk, 11) allowing hardware and/or software updates to be remotely sent and/or loaded onto one or more electronic components in the medical kiosk, and/or 12) allowing software to be loaded onto and/or removed from one or more electronic components in the medical kiosk.

In another and/or alternative embodiment of the invention, the novel method and apparatus for providing medical services, diagnoses, health, and/or wellness advice to individuals can include a pharmaceutical dispensing system that dispenses medications to the patient; however, this is not required. The pharmaceutical dispensing system can be located on the medical kiosk or be a unit separate from the medical device. The pharmaceutical dispensing system can be designed to allow the patient to obtain the medication with or without the assistance of the medical attendant. The pharmaceutical dispensing system can be designed to only dispense medication that was authorized by the medical provider. In one non-limiting arrangement, the medical provider can use the Provider Application to send instructions to the pharmaceutical dispensing system to dispense certain types and/or amounts of medication to the patient; however, this is not required. Such information can be stored by the medical provider in the patient's record; however, this is not required. The medical provider can send notification to the medical attendant that medication is being dispensed to the patient; however, this is not required. The send information can include type and/or quantity of medication; however, this is not required. Non-limiting medication and/or other materials that can be dispensed by the pharmaceutical dispensing system include antibiotics, aspirin, hydrocodone, simvastatin, Lisinopril, levothyroxine sodium, amlodipine besylate, omeprazole, Azithromycin, Amoxicillin, metformin, Hydrochlorothiazide, Lipitor, Nexium, Plavix, Advair Diskus, Abilify, Seroquel, Singulair, Crestor, Actos, Epogen, Band-Aid, tissue, alcohol wipe, bandage, cold pack, heading pad, etc. The payment for medication and/or materials from the pharmaceutical dispensing system can be by mobile device, payment at the medical kiosk, payment at attendant's station, and/or payment at the pharmaceutical dispensing system and/or by some other method and/or at some other location.

In still another and/or alternative embodiment of the invention, the novel method and apparatus for providing medical services, diagnoses, health, and/or wellness advice to individuals can include a data port and/or wireless receiver that can be used by a patient to download and/or upload information to a medical device on a patient (e.g., heart monitor, heart pacemaker, implantable cardioverter defibrillators, etc.). Such information can be designed to be viewed by the medical provider, and/or data can be sent to the medical device by the medical provider; however, this is not required.

In yet another and/or alternative embodiment of the invention, the novel method and apparatus for providing medical services, diagnoses, health, and/or wellness advice to individuals can designed to be transported to various locations to be used an emergency medical station; however, this is not required. For example, after a natural disaster (e.g., flood, hurricane, tidal wave, earthquake, fire, tornado, etc.), the medical kiosk of the present invention can be transported to the area of the incident and then be used as an emergency medical station. As can be appreciated, the medical kiosk can be continuous transported to various locations (e.g., remote rural locations, camp sites, etc.) to enable individuals in such locations to obtain medical assistance.

In still yet another and/or alternative embodiment of the invention, the novel method and apparatus for providing medical services, diagnoses, health, and/or wellness advice to individuals can be designed to allow patients to rate the medical provider and/or to view the ratings of medical providers that have offered services to patients in the medical kiosk; however, this is not required. Such ratings can be used by patients to select a certain medical provider for a visit, if such option is available.

In another and/or alternative embodiment of the invention, the novel method and apparatus for providing medical services, diagnoses, health, and/or wellness advice to individuals can designed to allow patient to rate the experience received in the medical kiosk and/or to view the ratings of other patients that have used the medical kiosk; however, this is not required.

In still another and/or alternative embodiment of the invention, the novel method and apparatus for providing medical services, diagnoses, health, and/or wellness advice to individuals can designed to automatically order supplies for the medical kiosk based on the usage of the medical devices in the medical kiosk; however, this is not required. For example, the number of patients using the medical kiosk can be monitored. If a thermometer was used for every visit, a software program can be used to automatically order the disposable component of the thermometer after a certain number of patients have visited the medical kiosk; however, this is not required. In another and/or additional example, software can be used to monitor the number of times a medical door for a medical device has been opened. Based on such number of door openings, a software program can be used to automatically order the disposable component of the medical device in a certain medical compartment after a certain number of door openings has been detected; however, this is not required.

In still yet another and/or alternative embodiment of the invention, the novel method and apparatus for providing medical services, diagnoses, health, and/or wellness advice to individuals can designed to generate a fresh scent in the medical kiosk; however, this is not required. The type of scent and/or method of scent delivery are non-limiting.

In another and/or alternative embodiment of the invention, the novel method and apparatus for providing medical services, diagnoses, health, and/or wellness advice to individuals can designed to collect information about patients, patient retention, and/or patient referrals for use in the marketing of the medical kiosk and/or to improve/alter/enhance the services provided by the medical kiosk; however, this is not required.

In still another and/or alternative embodiment of the invention, the novel method and apparatus for providing medical services, diagnoses, health, and/or wellness advice to individuals can designed to print and/or send coupons, advertisements, marketing literature, and/or medical literature to a patient that has used the medical kiosk and/or has registered with the medical kiosk; however, this is not required. Such coupons, advertisements, marketing literature, and/or medical literature can be general in nature and/or targeted to the particular patient and/or type of diagnoses received by the patient. For example, if a prescription has been written by the medical provider, one or more pharmacies may have a coupon sent to the patient to provide the patient with a discount, etc. if the patient fills the prescription at the pharmacy; however, this is not required.

It is one non-limiting object of the invention to provide tele-med services that are convenient to a user.

It is another and/or alternative one non-limiting object of the invention to provide tele-med services that are cost effective to a user.

It is still another and/or alternative one non-limiting object of the invention to provide tele-med services that can be provided to a user via a medical kiosk.

It is yet another and/or alternative one non-limiting object of the invention to provide tele-med services that can be provided to a user via a modular medical kiosk.

It is still yet another and/or alternative one non-limiting object of the invention to provide a medical kiosk and method for using a medical kiosk that is easy to assemble and disassemble.

It is another and/or alternative one non-limiting object of the invention to provide a medical kiosk and method for using a medical kiosk that includes an easy and convenient registration system and payment system.

It is still another and/or alternative one non-limiting object of the invention to provide a medical kiosk and method for using a medical kiosk that provides privacy to a user when obtaining medical services.

It is yet another and/or alternative one non-limiting object of the invention to provide a medical kiosk and method for using a medical kiosk that is sized and shaped to accommodate disabled or handicapped users.

It is still yet another and/or alternative one non-limiting object of the invention is to provide a medical kiosk and method for using a medical kiosk that includes medical instruments that can be used by a user when obtaining medical services.

It is another and/or alternative one non-limiting object of the invention to provide a medical kiosk and method for using a medical kiosk that includes video conferencing capabilities between a user and a medical provider.

It is still another and/or alternative one non-limiting object of the invention to provide a medical kiosk and method for using a medical kiosk that provides the option to play back one or more portions of the video conference session to the user after the video conference between the user and medical provider has been completed.

It is yet another and/or alternative one non-limiting object of the invention to provide a medical kiosk and method for using a medical kiosk that includes an attendant station, digital signage, and/or a registration station on the exterior of the medical kiosk.

It is still yet another and/or alternative one non-limiting object of the invention to provide a medical kiosk and method for using a medical kiosk that includes a Provider Screen and/or Patient Screen in the interior of the medical kiosk.

It is another and/or alternative one non-limiting object of the invention to provide a medical kiosk and method for using a medical kiosk that includes one or more medical device cabinets on the interior of the medical kiosk.

It is still another and/or alternative one non-limiting object of the invention to provide a medical kiosk and method for using a medical kiosk that includes the use of a Patient Appointment or Registration Application, Attendant Application, Patient Appointment or Registration Application, Provider Application, Administrator Application, Patient Portal and/or Provider Portal.

It is yet another and/or alternative one non-limiting object of the invention to provide a medical kiosk and method for using a medical kiosk that includes a Patient Appointment or Registration Application that enables patients to schedule an appointment at a medical kiosk.

It is still yet another and/or alternative one non-limiting object of the invention to provide a medical kiosk and method for using a medical kiosk that includes Patient Appointment or Registration Application that enables a patient to enter insurance information and/or to make a payment and/or copay for the medical visit in the kiosk.

It is another and/or alternative one non-limiting object of the invention to provide a medical kiosk and method for using a medical kiosk that includes Patient Registration System that enables a patient to check-in for a preexisting appointment.

It is still another and/or alternative one non-limiting object of the invention to provide a medical kiosk and method for using a medical kiosk that includes a Patient Registration System that enables a patient to identify the patient's symptoms, medications, allergies, and/or medical conditions.

It is yet another and/or alternative one non-limiting object of the invention to provide a medical kiosk and method for using a medical kiosk that includes registration and/or check-in system that enables a patient to request assistance from a medical attendant.

It is still yet another and/or alternative one non-limiting object of the invention to provide a medical kiosk and method for using a medical kiosk that includes an Attendant Application that enables a medical attendant to monitor past, present and/or future appointments for the medical kiosk.

It is another and/or alternative one non-limiting object of the invention to provide a medical kiosk and method for using a medical kiosk that includes an Attendant Application that enables a medical attendant to monitor the status of a current visit in the medical kiosk.

It is still another and/or alternative one non-limiting object of the invention to provide a medical kiosk and method for using a medical kiosk that includes an Attendant Application that enables a medical attendant to cancel and/or reschedule an appointment to a medical kiosk.

It is yet another and/or alternative one non-limiting object of the invention to provide a medical kiosk and method for using a medical kiosk that includes an Attendant Application that informs that medical attendant that the patient requires assistance.

It is still yet another and/or alternative one non-limiting object of the invention to provide a medical kiosk and method for using a medical kiosk that includes an Attendant Application that enables the medical attendant to keep track of the clean-up of the medical kiosk.

It is another and/or alternative one non-limiting object of the invention to provide a medical kiosk and method for using a medical kiosk that enables the medical assistant to activate an automated sanitation and/or cleaning system of the medical kiosk.

It is still another and/or alternative one non-limiting object of the invention to provide a medical kiosk and method for using a medical kiosk that includes an Attendant Application that enables a medical assistant to validate the insurance and/or ID of a patient.

It is yet another and/or alternative one non-limiting object of the invention to provide a medical kiosk and method for using a medical kiosk that includes a Patient Appointment or Registration Application that helps the patient capture vitals and/or enter the vitals information during the visit.

It is still yet another and/or alternative one non-limiting object of the invention to provide a medical kiosk and method for using a medical kiosk that includes a Patient Appointment or Registration Application that enables the patient to request assistance from the medical attendant.

It is another and/or alternative one non-limiting object of the invention to provide a medical kiosk and method for using a medical kiosk that includes a Patient Appointment or Registration Application that can assist the patient during the consultation with the medical provider.

It is still another and/or alternative one non-limiting object of the invention to provide a medical kiosk and method for using a medical kiosk that includes a Patient Appointment or Registration Application that enables a patient to take a survey regarding the consultation with the medical provider and/or the use of the medical kiosk.

It is yet another and/or alternative one non-limiting object of the invention to provide a medical kiosk and method for using a medical kiosk that includes a Provider Application that assists the medical provider in providing medical services to the patient in the medical kiosk.

It is still yet another and/or alternative one non-limiting object of the invention to provide a medical kiosk and method for using a medical kiosk that includes a Provider Application that provides information to the medical provider regarding past, current and future appointment that have been schedules with the medical provider.

It is another and/or alternative one non-limiting object of the invention to provide a medical kiosk and method for using a medical kiosk that includes a Provider Application that enables the medical provider to view personal information that the patient has entered regarding the medical visit.

It is still another and/or alternative one non-limiting object of the invention to provide a medical kiosk and method for using a medical kiosk that includes a Provider Application that enables the medical provider to view vitals that have been collected on the patient.

It is yet another and/or alternative one non-limiting object of the invention to provide a medical kiosk and method for using a medical kiosk that includes a Provider Application that enables the medical provider to request that the medical attendant assist the patient in the medical kiosk.

It is still yet another and/or alternative one non-limiting object of the invention to provide a medical kiosk and method for using a medical kiosk that includes a Provider Application that enables the medical provider to control the use and/or access of one or more medical devices in the medical kiosk.

It is another and/or alternative one non-limiting object of the invention to provide a medical kiosk and method for using a medical kiosk that includes a Provider Application that enables a medical provider to create a visit summary of the patient in the medical kiosk.

It is still another and/or alternative one non-limiting object of the invention to provide a medical kiosk and method for using a medical kiosk that includes a Provider Application that enables the medical provider to update personal information, medical history information and/or symptom information about the patient.

It is yet another and/or alternative one non-limiting object of the invention to provide a medical kiosk and method for using a medical kiosk that includes a Provider Application that enables a medical provider to select and/or enter a diagnosis for a patient.

It is still yet another and/or alternative one non-limiting object of the invention to provide a medical kiosk and method for using a medical kiosk that includes a Provider Application that enables the medical provider to enter notes about a patient and/or create a treatment plan for a patient.

It is another and/or alternative one non-limiting object of the invention to provide a medical kiosk and method for using a medical kiosk that includes a Provider Application that enable a medical provider to view information about past visits by a patient.

It is still another and/or alternative one non-limiting object of the invention to provide a medical kiosk and method for using a medical kiosk that includes a mobile application and/or an on-line application that enables a patient to 1) conveniently locate an available medical kiosk, 2) schedule an appointment (e.g., date and/or time), 3) pre-register symptoms and/or reasons for visit, 4) set and/or cancel an appointment, 5) received reminders and/or updates regarding appoints, 6) obtain information about medical kiosk availability, 7) obtain information about certain medical provider availability, 8) obtain information about the available medical provider (e.g., name, specialty, etc.), 9) enable the selection of a certain medical provider and/or medical provider in a certain field of medicine, 10) obtain map information, address information and/or hours of operation information regarding selected medical kiosk, 11) located closest kiosk and/or kiosk availability for a certain medical provider and/or medical provider in a certain field of medicine, 12) presubmit and/or preclear medical insurance, 13) submit payment information, 14) receive information on payment status, 15) receive information in insurance coverage, 16) receive appointment reminders and/or updates, and/or 17) receive medication reminders, and the like.

It is yet another and/or alternative one non-limiting object of the invention to provide a medical kiosk and method for using a medical kiosk that includes a scale in the floor of the medical kiosk.

It is still yet another and/or alternative one non-limiting object of the invention to provide a medical kiosk and method for using a medical kiosk that includes a medication adherence application that allows a user/patient to 1) speak to a pharmacist, 2) change the patient's medications alerts, 3) learn about certain types of medical conditions, 4) check medication orders status, 5) check medication delivery status, 6) refill a prescriptions, 7) transfer prescriptions to a another location, 8) obtain information about recommended medication dosages, 9) obtain information about recommended times to take medications, 10) obtain information about recommended frequency for taking medications, 11) obtain information about medications, 12) obtain information about generic brands available for medications, 13) request an appointment to speak with a medical provider, 14) enter information regarding compliance information regarding medication usage by patient, and/or 15) receive compliance reports for patients regarding medication usage.

It is another and/or alternative one non-limiting object of the invention to provide a medical kiosk and method for using a medical kiosk that includes a medication adherence application that 1) sends reminders for user/patients to take their medications, 2) monitors a user's/patient's adherence to taking their meds and/or distributes progress reports to the patient, and/or 3) automatically enrolls a patient in an electronic prescriptions network which can optionally send a patient's prescriptions to their choice of pharmacy.

It is still another and/or alternative one non-limiting object of the invention to provide a medical kiosk and method for using a medical kiosk that includes one or more headphone jacks in the medical kiosk.

It is yet another and/or alternative one non-limiting object of the invention to provide a medical kiosk and method for using a medical kiosk that includes a medical kiosk having HD components and an industrial strength design.

It is still yet another and/or alternative one non-limiting object of the invention to provide a medical kiosk and method for using a medical kiosk that includes a medical kiosk having a modular configuration and/or a configuration that enables the medical kiosk to be brought in to or removed from locations having a standard sized doorway.

It is another and/or alternative one non-limiting object of the invention to provide a medical kiosk and method for using a medical kiosk that includes a medical kiosk having a check-in registration system positioned on the exterior of the medical kiosk.

It is still another and/or alternative one non-limiting object of the invention to provide a medical kiosk and method for using a medical kiosk that includes a medical kiosk having one or more medical device cabinets located in the interior of the medical kiosk.

It is yet another and/or alternative one non-limiting object of the invention to provide a medical kiosk and method for using a medical kiosk that includes a medical kiosk having digital signage on the interior and/or exterior of the medical kiosk.

It is still yet another and/or alternative one non-limiting object of the invention to provide a medical kiosk and method for using a medical kiosk that includes a medical kiosk having a built-in sanitation system.

It is another and/or alternative one non-limiting object of the invention to provide a medical kiosk and method for using a medical kiosk that allows patients to 1) choose between name brand and generic drugs, 2) choose the supply quantity for the prescription (i.e., 30 days supply, 60 days supply, 90 days supply, etc.), 3) choose between picking the prescription up at the pharmacy of their choice or mail delivery of the prescription, 4) enter medical insurance for partial or full payment of the prescription, 5) enter a credit or debit card information to pay for the prescription, 6) enter information for mail delivery of the prescription, 8) enter information to provide automatic reminders to patient regarding refilled and/or follow-up medical visits, 9) enter information to enable patient to be notified when prescription has been mailed and/or is ready to be picked-up at the pharmacy; however, this is not required, 10) obtain a print out and/or electronic version of the prescription written by the medical provider, and/or 11) receive information about the issued prescription (e.g., prescribed use, side effects, etc.) in printout and/or electronic form.

It is still another and/or alternative one non-limiting object of the invention to provide a medical kiosk and method for using a medical kiosk that includes a medical kiosk having a movable front interior wall panel to enable access to components that are positioned behind the front interior wall of the medical kiosk.

These and other objects and advantages will become apparent to those skilled in the art upon reading and following the description taken together with the accompanying drawings.

BRIEF DESCRIPTION OF THE DRAWINGS

Reference may now be made to the drawings which illustrate various preferred embodiments that the invention may take in physical form and in certain parts and arrangement of parts wherein.

DETAILED DESCRIPTION OF ONE NON-LIMITING EMBODIMENTS

Figure 1:
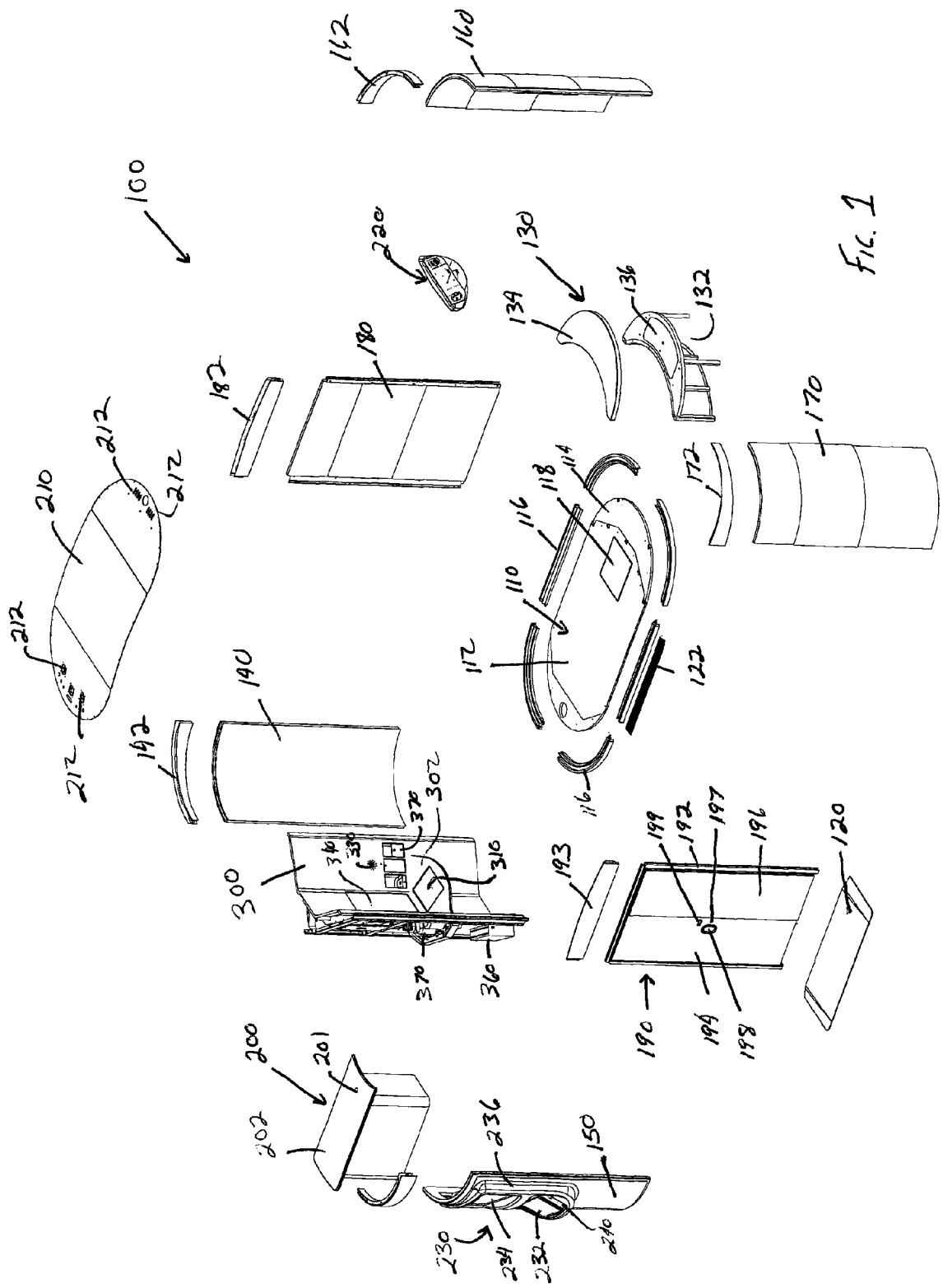
FIG. 1 is an exploded view of a medical kiosk in accordance with the present invention.

Referring now to the drawings wherein the showings are for the purpose of illustrating one non-limiting embodiments of the invention only and not for the purpose of limiting same, FIGS. 1-12 illustrate one non-limiting embodiment of the medical kiosk in accordance with the present invention. The medical kiosk 100 is designed to be used by a user to obtain medical services. Such medical services are generally tele-med services wherein one or more medical providers located at a remote location provide medical services to one or more users that are using the medical kiosk. As can be appreciated, non-tele-med services can also be provided to a user that is using the medical kiosk.

The shape, size and configuration of the medical kiosk are non-limiting. The materials and colors of the medical kiosk are also non-limiting. Generally, the materials used to form the medical kiosk include materials that resist or prevent microbial growth; however, this is not required. The medical kiosk illustrated in FIGS. 1-12 is designed to accommodate about 1-4 adults; however, it can be appreciated that the medical kiosk can be designed to accommodate additional users.

The medical kiosk is generally designed to be modular so that it can be easily assembled and disassembled; however, this is not required. FIG. 1 illustrates one non-limiting set of modular components of the medical kiosk. The medical kiosk generally includes a floor panel 110; however, this is not required. The floor panel, when used, can be a one or two piece unit; however, the floor panel can be formed of more than two pieces. As illustrated in FIG. 1, the floor panel is formed of two pieces 112, 114 that can be positioned and/or connected together in a variety of ways. A rail system 116 can be positioned about the floor panel to facilitate in connecting other components of the medical kiosk to the floor panel; however, this is not required. The rail system, when used, can be connected to the floor panel and/or other components of the medical kiosk in a variety of ways. The floor panel is generally formed of a durable material (e.g., plastic, metal, wood, composite material, man-made materials, etc.). The floor panel can be formed of a slightly compressible material to facilitate in the comfort of walking on the floor panel; however, this is not required. The floor panel is illustrated as having an oval shape; however, other shapes can be used (e.g., circular, square, rectangular, polygonal, etc.). The maximum length of the floor panel is generally 3-15 feet, typically 4-12 feet, more typically about 6-10 feet, and even more typically about 8-9 feet; however, other lengths can be used. The maximum width of the floor panel is generally 3-10 feet, typically 4-8 feet, and more typically about 4-6 feet; however, other widths can be used. The top surface area of the floor panel is generally 10-150 sq. ft., typically 15-80 sq. ft., and more typically about 50-60 sq. ft.; however, other surface areas of the floor panel can be used. The floor panel can be sized to enable a user in a wheelchair to enter the medical kiosk and turn and/or fully maneuver in the medical kiosk while sitting in the wheelchair; however, this is not required. The thickness of the floor panel is generally about 0.1-5 inches, and typically about 0.25-3 inches; however, other thicknesses of the floor panel can be used.

A weight scale 118 can optionally be partially or fully embedded in the floor panel. As can be appreciated, a weight scale can be placed on the top surface of the floor panel and/or positioned on other regions of the medical kiosk (e.g., chair, bench, etc.). The weight scale, when used, provides information about the weight of a user. The information from the scale can be electronically (e.g., wired, wirelessly) transferred to a medical provider and/or displayed to the user and/or medical provider.

A ramp 120 can be optionally used to facilitate entry and exiting of the medical kiosk; however, this is not required. The shape and size of the ramp are non-limiting. The ramp can be made of a similar material as the floor panel; however, this is not required. The ramp generally includes a sloped surface to facilitate in transitioning from a floor surface to the top surface of the floor panel; however, this is not required. A ramp connector 122 can be used to connect the ramp to the floor panel; however, this is not required.

The medical kiosk can optionally include one or more benches 130, stools and/or chairs. When bench 130 is included in the medical kiosk, the bench is generally positioned on the back interior wall of the medical kiosk; however, this is not required. The bench can be used to allow a parent, guardian, spouse, relative, friend, etc. to sit in the medical kiosk while the user is obtaining medical services in the medical kiosk. The bench can be designed to enable one or more persons to sit on the bench. The bench can optionally include a storage space 132 under the seat of the bench that can be used to store supplies, equipment, etc. for the medical kiosk. A liftable seat section 134 can be used to access the storage space. When the bench includes a storage space, the bench can include a door 136 which may or may include a lock to limit access to the storage space; however, this is not required. As can be appreciated, the medical kiosk can include one or more chairs, not shown, to enable one or more users to sit in the medical kiosk while receiving medical services in the medical kiosk. The bench is generally about 10-25 inches high, and typically about 16-20 inches high; however, other heights can be used.

Figure 3:
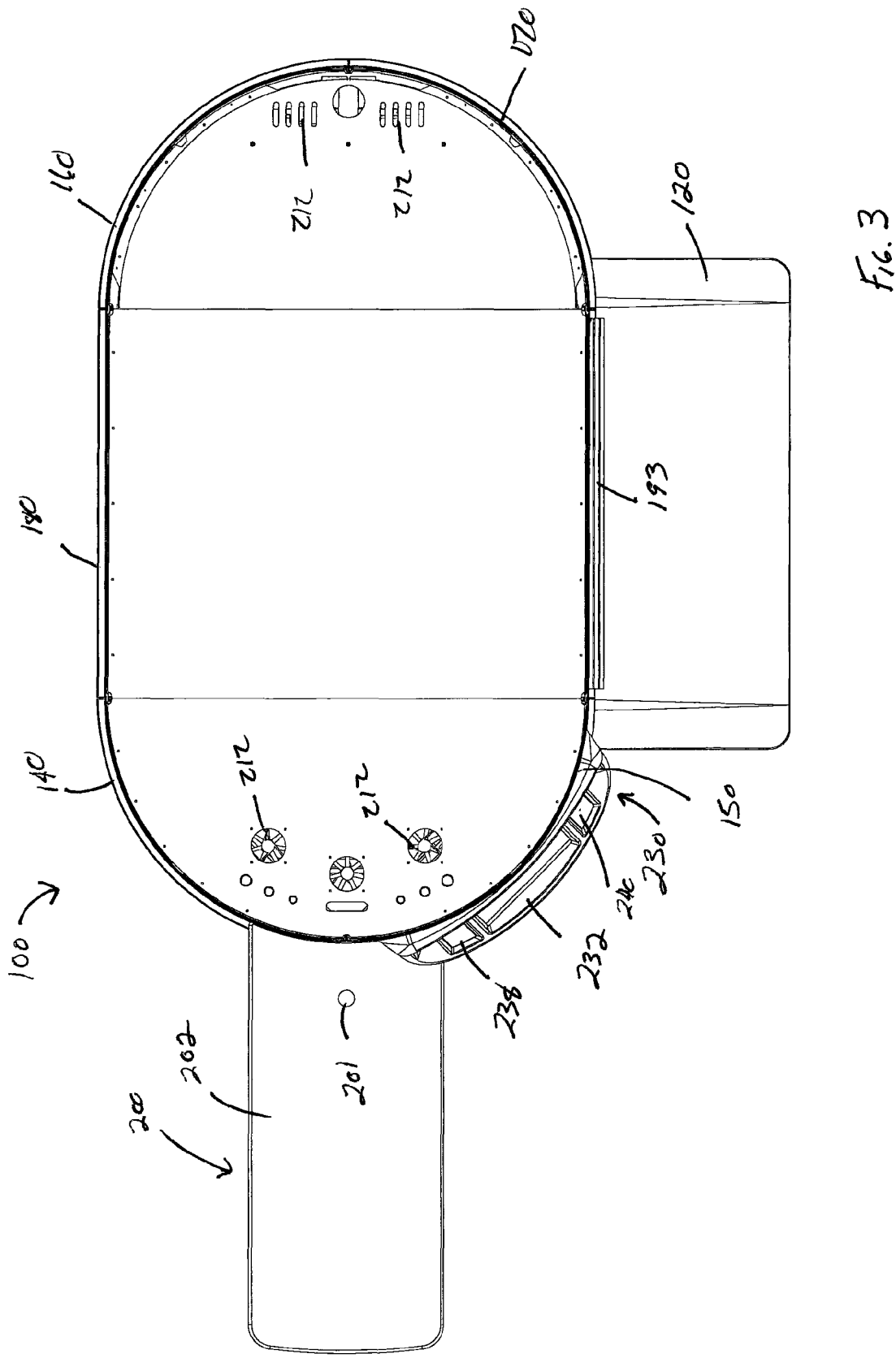
FIG. 3 is a top view of the medical kiosk of FIG. 1.
Figure 4:
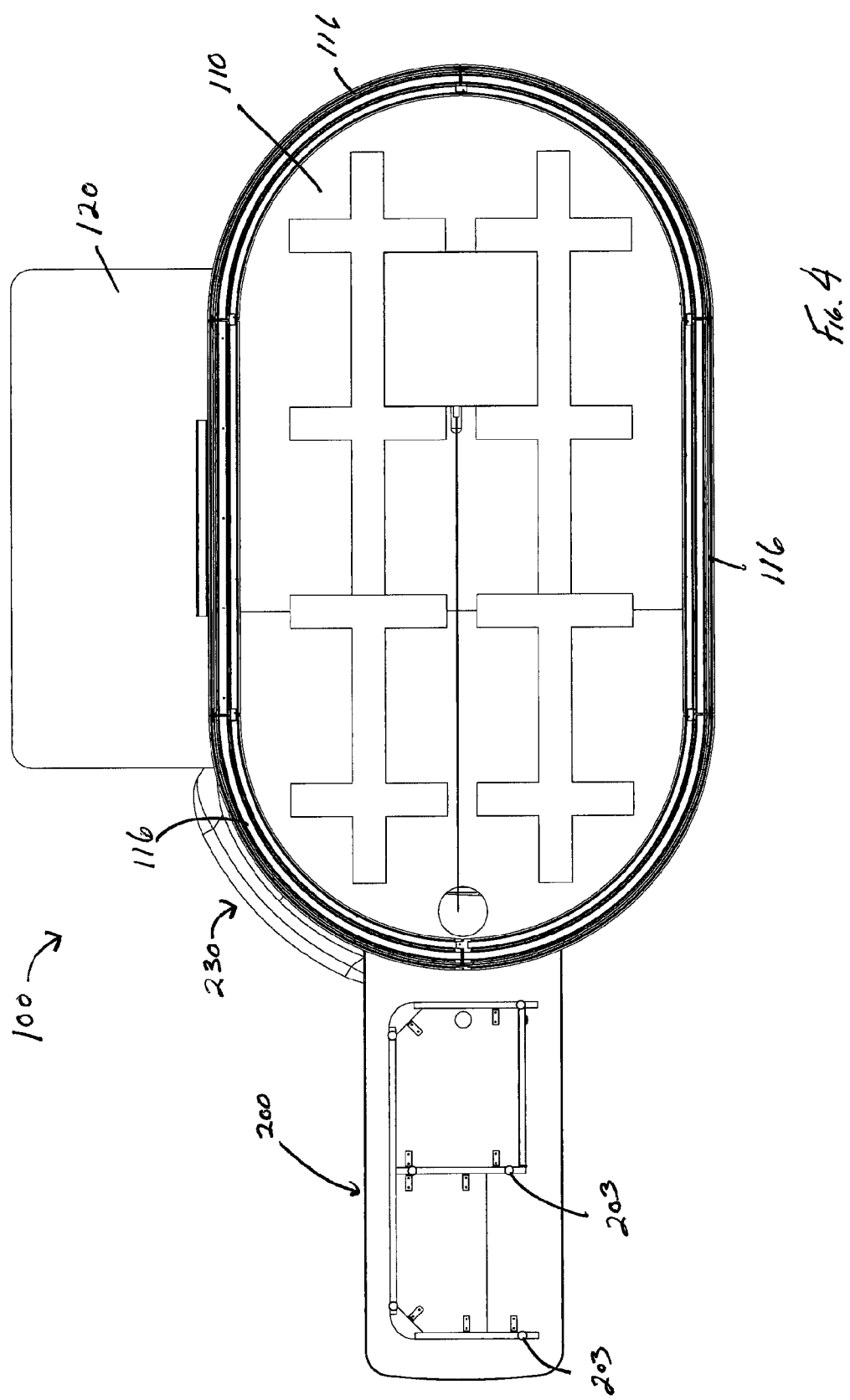
FIG. 4 is a bottom view of the medical kiosk of FIG. 1.

The medical kiosk is illustrated as having two front panels 140, 150, two rear panels 160, 170, one side wall 180, and one door system 190. The front panels, rear panels, side wall, and door system are generally formed of a durable material (e.g., plastic, metal, wood, composite material, man-made materials, etc.). The front panels, rear panels, side wall can have upper trim 142, 152, 162, 172, 182; however, this is not required. As can be appreciated, the medical kiosk can be designed to only include a single front panel and/or a single rear panel. As can also be appreciated, the medical kiosk can be designed to include more than two front panels and/or more than two rear panels. As can be appreciated, the medical kiosk can be designed to include more than one side wall and/or more than one door system. As can also be appreciated, a side wall can be substituted for another door system; however, this is not required. The general shape and size of the front and rear panels are the same; however, this is not required. As illustrated in FIG. 1, the shape of the front and rear panels is arcuate. The radius of curvature is about 10-100 inches, typically 15-50 inches, and more typically about 20-35 inches; however, other radius of curvatures can be used. As illustrated in FIGS. 1 and 3, the front and rear panels have an angle of curvature of about 90° or a quarter of a circle; however, it can be appreciated that one or both rear and/or front panels can have different angles of curvature. The general shape and size of the side wall and the door system are generally the same; however, this is not required. As illustrated in FIGS. 1 and 3, the side wall and door system lie in a generally flat plane; however, this is not required. As illustrated in FIG. 3, the assembly of the front and rear panels and the side wall and door system forms a generally oval shape for the medical kiosk. The two front panels and two rear panels are illustrated as having the same or similar footprint; however, this is not required. Likewise, the side wall and the door system have the same or similar footprint; however, this is not required. The similarity in the shape and footprint of the wall components of the medical kiosk enables the medical kiosk to be assembled in a manner that is convenient for the facility that will include the medical kiosk. For example, if the door system needs to be positioned on the left side of the medical kiosk, instead of the right side, the similarly shaped side wall and door system enables the medical kiosk to be assembled in such a manner. Also, if the registration station of the medical system needs to be placed on the left side or right side or on the rear end of the medical kiosk instead of the front end, the similarly shaped front and rear panels can be easily exchanged to create such configuration for the medical kiosk. The modular medical kiosk not only accommodates multiple configurations of the medical kiosk, it also facilitates in enabling the medical kiosk to be moved into an existing facility and then assembling the medical kiosk in such facility without having to modifying the entry ways into or out of the facility. The thickness and height of the front panels, rear panels, side wall and door system are non-limiting. Generally, the maximum height of the front panels, rear panels, side wall and door system is about 5-12 ft., typically about 6-9 ft., and more typically about 7-8 ft.; however, other heights can be used. The thickness of the front panels, rear panels, side wall and door system is generally about 0.5-10 inches, typically about 1-5 inches, and more typically about 1-2 inches; however, other thicknesses can be used. The front panels, rear panels, side wall and door system can optionally include insulation, sound dampening material, etc.; however, this is not required. The front panels, rear panels, side wall and door system can be designed to be connected together in a variety of ways (e.g., bolted/screwed together, latched together, snap fitted together, press fitted together, etc.). Generally, the arrangement is used to connect together the front panels, rear panels, side wall and door system is selected to enable easy connecting and disconnecting of the front panels, rear panels, side wall and door system from one another. One or more of the front panels, rear panels, side wall and door system can include openings, windows, transparent/semi-transparent regions that allow for ventilation, illumination, and/or viewing; however, this is not required. Generally, front panels, rear panels, side wall and door system are mostly or fully formed of opaque or non-transparent materials so as to ensure the privacy of the user in the medical kiosk; however, this is not required.

Figure 2:
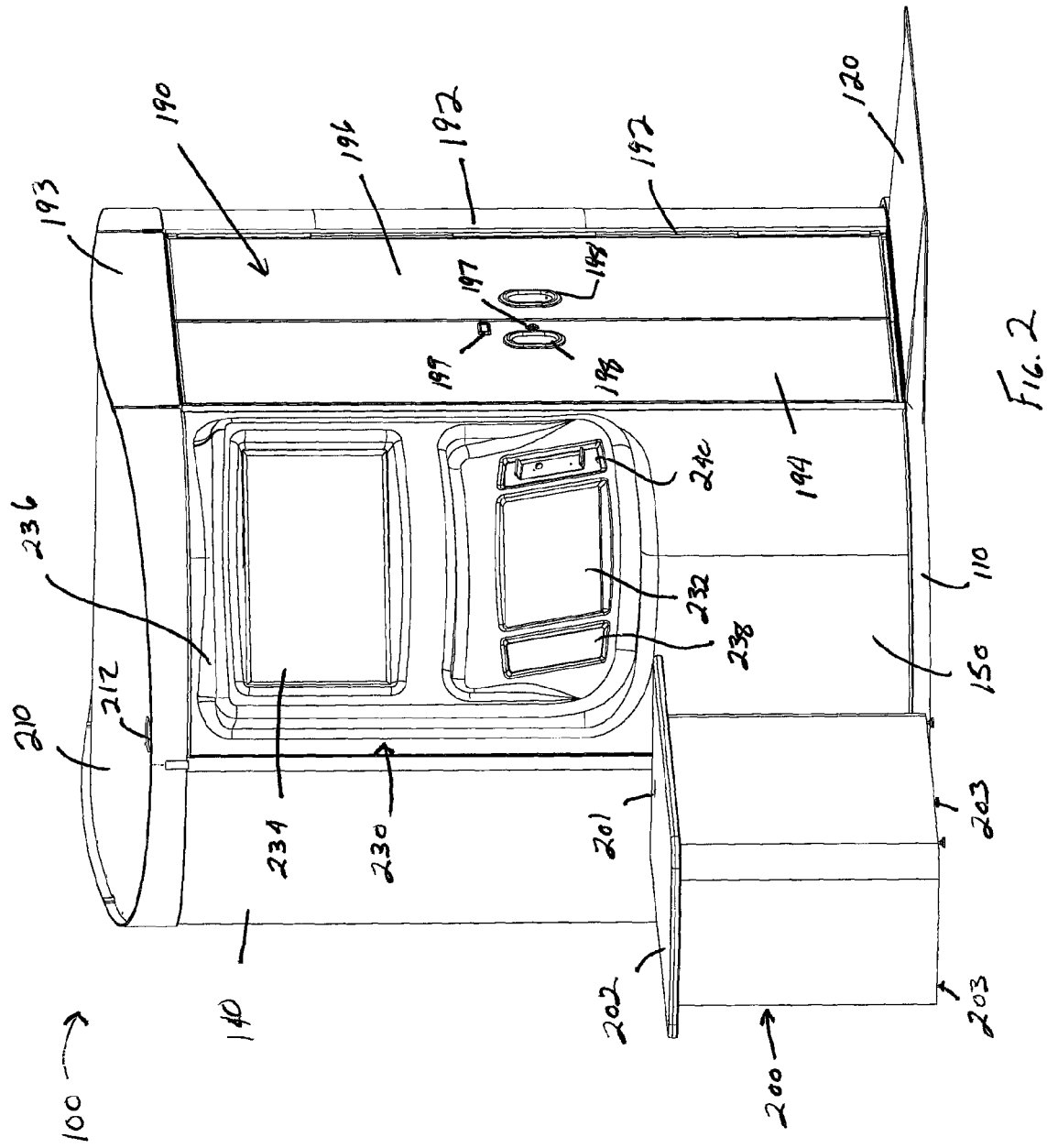
FIG. 2 is a front elevation view of the medical kiosk of FIG. 1.

The configuration of the door system 190 is non-limiting. As illustrated in FIGS. 1 and 2, the door system includes a frame 192, 193 and two doors 194, 196; however, it can be appreciated that the door system only includes a single door. One or more both doors can include a handle or grasp cavity 198 on one or both sides of the one or both doors. The one or more doors can be designed to open and close in a variety of ways (e.g., swing open and closed, slide open and closed on a top/bottom rail system, etc.). As can be appreciated, the one or more doors for the medical kiosk can also or alternatively be positioned on one or more of the front or rear panels; however, this is not required. The maximum height of the doors is generally about 5-9 ft., and typically about 6-7 ft.; however, other heights can be used. The maximum width of the entry provided by the one or more doors when fully open is generally about 15-60 inches, typically about 25-55 inches, and more typically about 30-50 inches; however, other widths can be used. The door opening is generally selected to enable a standard wheelchair to pass through the opening; however, this is not required. The door system can optionally include an indicator 199 (e.g., light, message, etc.) that indicates when the medical kiosk is in use or is available. As can be appreciated, the use indicator can be located on other or additional locations on the medical kiosk. The door system can optionally include a lock arrangement 197. The configuration of the lock arrangement is non-limiting. The lock arrangement, when used, can be designed to enable the user to lock the doors to the kiosk medical to prevent access to the interior of the medical kiosk while the user is in the medical kiosk; however, this is not required. The lock arrangement can also or alternatively be used to lock and prevent access to the interior of the medical kiosk when the medical kiosk is not in use; however, this is not required.

The medical kiosk can optionally include an exterior attendant station that is connected to and/or positioned near the medical kiosk. The exterior attendant station can be used by one or more attendants, medical providers, etc. As illustrated in FIGS. 1-5 and 7-9, a desk 200 can be connected to and/or positioned next to an exterior wall of the medical kiosk. The desk can be formed of one or more pieces. When the desk is designed to be connected to an exterior wall of the medical kiosk, such connection arrangement is not limited (e.g., screw, bolt, clamp, press fit, snap arrangement, etc.). The desk can include a desk top 202, one or more legs 203, one or more shelf regions 204, one or more cabinet doors 206, one or more shelves 208, drawers, etc. The one or more doors, when used, can optionally include a lock 207. The desk top 202 can optionally include an opening 201 for cables, etc. One or more chairs, not shown, can be used to allow one or more attendants, medical providers, etc. to sit at the desk. The desk can be used to support a computer, printer, files, supplies, medical devices, refrigerator, medicine, patient blood and/or urine samples, phone, monitor, scanner, credit card reader, etc. The one or more one or more attendants, medical providers, etc. located at the desk can assist a user in using the medical kiosk, maintain and/or clean the medical kiosk, provide medical services to a user of the medical kiosk, etc. The desk is illustrated as positioned at or adjacent to one or both front panels; however, this is not required. Generally the attendant, when used, is not a medical provider; however, this is not required. The attendant, when used, is generally trained to assist a user to use the medical kiosk; however, this is not required. The attendant can 1) provide assistance to a user during the registration process and/or payment process, 2) provide assistance to a user about the medical kiosk and/or how to use the medical kiosk, 3) provide assistance to a user regarding technology in the medical kiosk and/or how to use such technology in the medical kiosk, 4) provide assistance to a user to enter and/or exit the medical kiosk, 5) clean and/or sanitize the medical kiosk, 6) answer and/or assist the user in other ways regarding the medical kiosk and/or services provided by the medical kiosk, 7) assist in the registration, appointment and/or check-in process for a user, etc.

The medical kiosk can optionally include a ceiling panel 210. The ceiling panel can be formed of one or more pieces. The ceiling panel can be formed of a transparent or semi-transparent material to allow light to enter and illuminate the interior of the medical kiosk for partial or fully ambient lighting of the medical kiosk; however, this is not required. One or more lights, not shown, can be positioned on the ceiling panel to illuminate the interior of the medical kiosk; however, this is not required. The ceiling panel is illustrated as including a plurality of vents 212 to enable air to circulate inside the medical kiosk; however, this is not required. One or more fans can be positioned on or adjacent to one or more of the vents; however, this is not required. As can be appreciated, the location of the one or more fans, when used, is non-limiting. As can also be appreciated, one or more fan systems, when used, can also or alternatively be positioned on other components of the medical kiosk (e.g., front panel, back panel, side wall, door system, floor panel, etc.). Generally, the rear vents 212 are designed to allow air into the medical kiosk and front vents are designed to allow air to exit the medical kiosk; however, this is not required. One or more fan systems, when used, and/or vents can optionally include a filter system, to partially or fully filter dust, mites, airborne particles, micro-organisms, viruses, etc. from the air prior to the air entering into the medical kiosk and/or prior to the air exiting the medical kiosk; however, this is not required. The filter can include many different arrangements (e.g., HEPA filter, electronic filter, liquid filter, etc.).

The medical kiosk can optionally include a cleaning system that is designed to clean one or more portions of the interior of the medical kiosk and/or kill/neutralize some or all germs and/or other micro-organisms in the medical kiosk. One non-limiting cleaning system that can be used is a UV sanitizing system 220. As can also be appreciated, a mist sanitizer can also or alternatively be used to fully or partially clean/sanitize one or more portions of the medical kiosk. As illustrated in FIGS. 1, 8, 9 and 12, the UV sanitizing system 220 can be connected to or positioned adjacent to the ceiling panel and rear panels; however, this is not required. The UV sanitizing system generally includes one or more UV lights that are designed to kill some or all of the germs and/or other micro-organisms in the medical kiosk. Generally the germs and/or other micro-organisms in the medical kiosk are treated when the interior of the medical kiosk does not include a user. The UV sanitizing system can optionally include one or more standard lights that can be used to provide illumination in the medical kiosk; however, this is not required. The UV sanitizing system can optionally include one or more vents that allow air drawn into the medical kiosk by a fan system to flow into the interior of the medical kiosk; however, this is not required. The UV sanitizing system can optionally include a cooling fan for the one or more UV lights and/or optional standard lights; however, this is not required. The UV sanitizing system can optionally include all or a portion of a mist sanitizing system; however, this is not required. The UV sanitizing system can house one or more cameras, speakers, sensors (e.g., temperature sensor, motion sensor, sound sensor, etc.), etc. for use in the medical kiosk; however, this is not required. The UV sanitizing system includes a shroud 222 that includes vent/light openings 224 to house the components of the UV sanitizing system; however, this is not required. The shape, size and configuration of the shroud are non-limiting. When a mist sanitizing system is additionally or alternatively used, one or more mist nozzles can be located in one or more regions of the medical kiosk so as to direct the sanitizing mist to desired locations in the medical kiosk. The sanitizing system, when used, can be activated by an attendant and/or a medical provider while the medical kiosk is not being used by a user. The doors to the medical kiosk can be closed and/or locked to prevent a user from entering the medical kiosk during a sanitizing process; however, this is not required.

Figure 5:
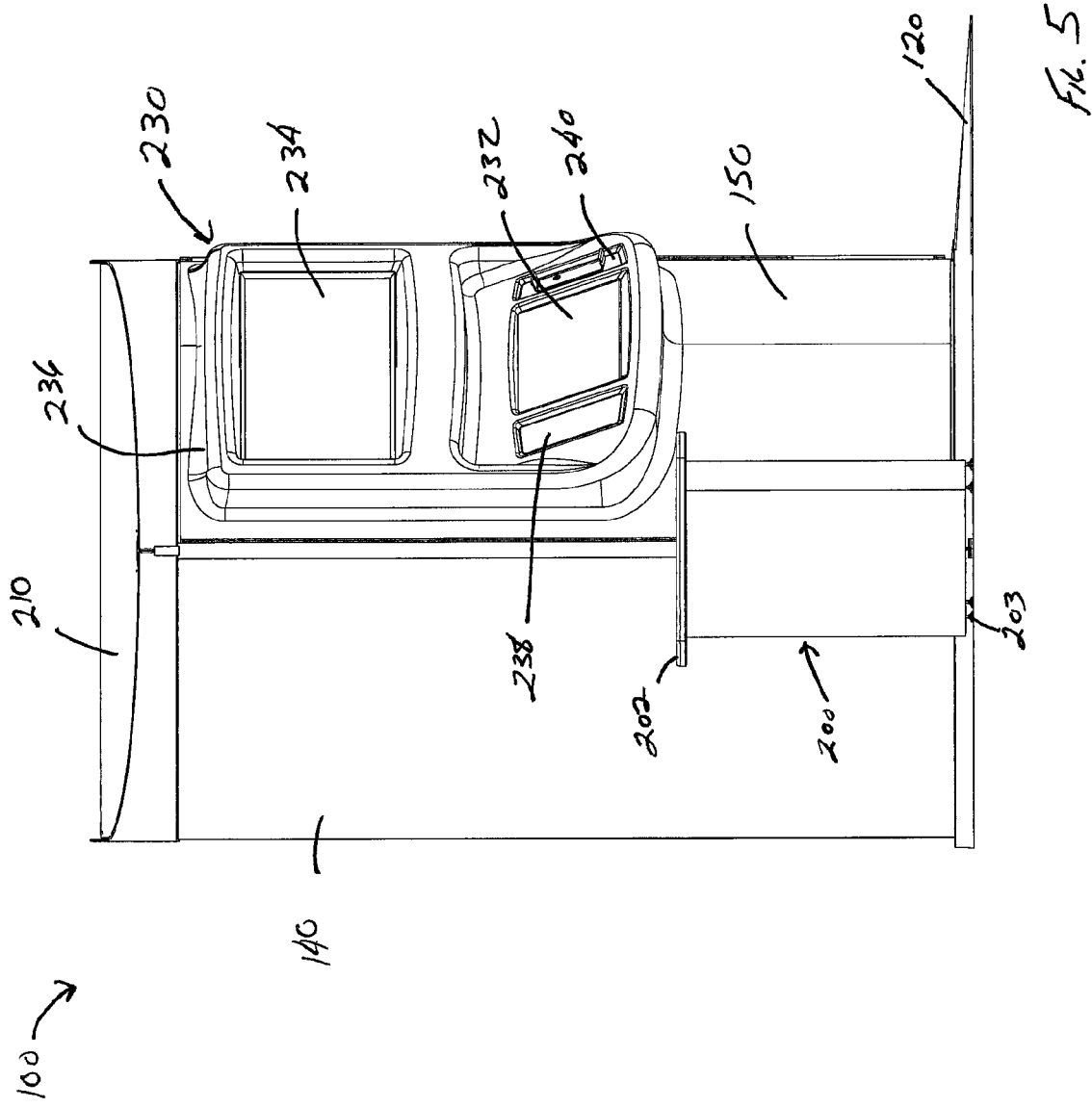
FIG. 5 is a front side view of the medical kiosk of FIG. 1.
Figure 6:
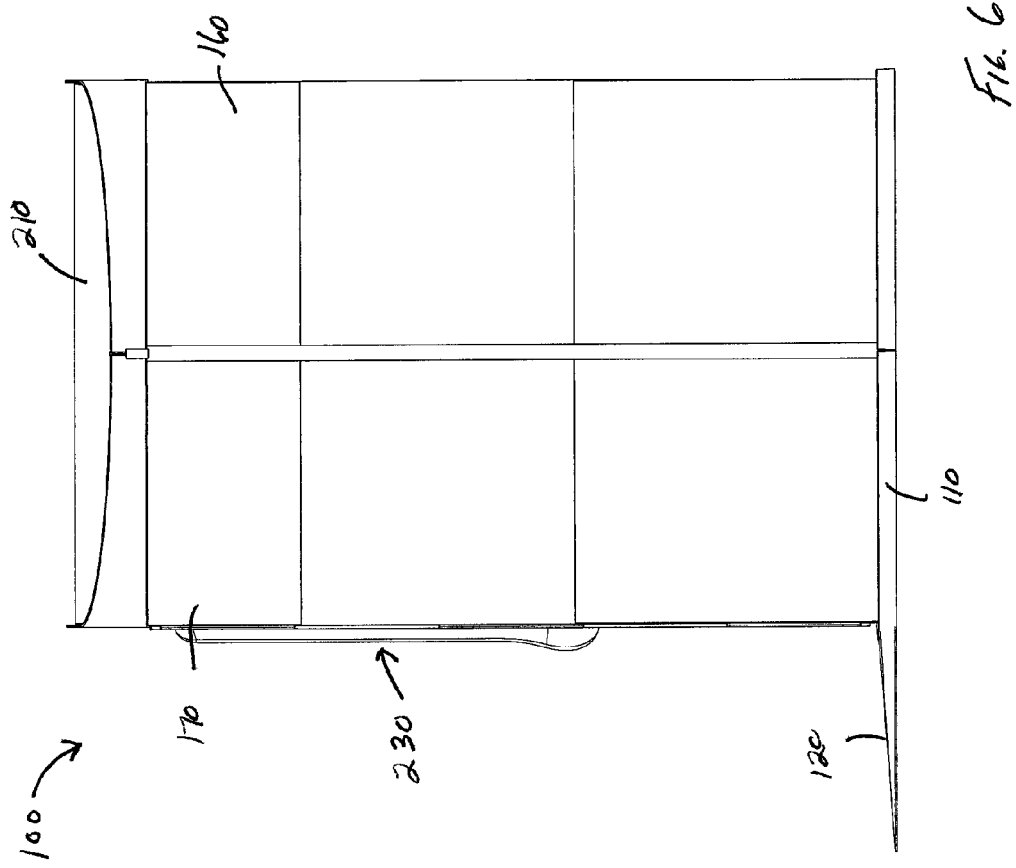
FIG. 6 is a back side view of the medical kiosk of FIG. 1.
Figure 7:
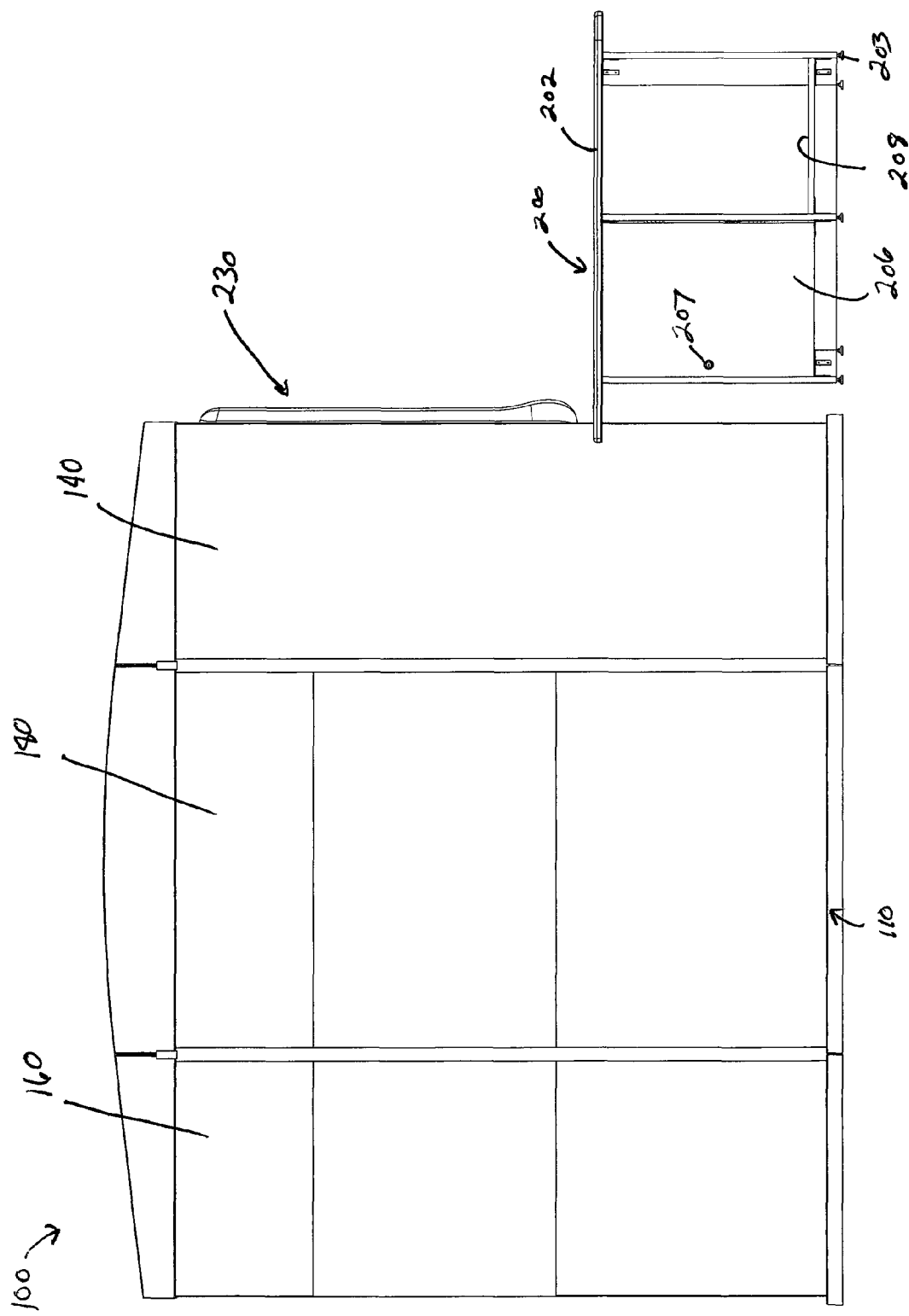
FIG. 7 is a back view of the medical kiosk of FIG. 1.

Referring now to FIGS. 1-5 and 7-10, front panel 150 includes a registration station 230. The registration station is illustrated as including a touch screen 232, a display screen 234, and an optional frame 236 that such components can be mounted thereto. The shape of the frame, when used, is non-limiting. The frame, when used, can be designed to be easily removed from the front panel to enable servicing, repair, replacement, etc. of one or more components of the registration station; however, this is not required. As can be appreciated, the registration station can also or alternatively include other or optional features (e.g., additional display screen, additional touch screen, lights, buttons, switches, camera, speakers, microphone, keyboard, scanner, receiver, transmitter, credit card/debit card or other some other card reader, smart phone or other smart device reader/scanner, finger and/or eye scanner, shelf, printer, storage cavity, service access door, motion sensor, sound sensor, temperature sensor, logos, etc.). The touch screen is generally used to allow a user to enter in information about the user (e.g., age, sex, contact information, payment information, medical history, medical issue, etc.). The touch screen can be substituted for a keyboard; however, this not required. The frame is designed to mount the touch screen at some angle (e.g., 10-80°) relative to the front plane of the front panel 150 as illustrated in FIGS. 1, 2 and 5; however, this is not required. The frame optionally includes one or more side sections 238, 240 that can include one or more other or optional features of the registration station. As can be appreciated, one or more other or optional features of the registration station can also or alternatively be located on other regions of the registration station. The touch screen can display various types of information (e.g., electronic keyboard, instructions on how to register, questions that are displayed during registration, instructions during registration, information displayed to user during registration, various templates, various menus, various lists of information, etc.). As can be appreciated, the medical kiosk can be designed to accept voice commands during the registration process; however, this is not required. The display screen can be used to provide various types of information (e.g., registration information, information input by the user, advertising information, information about the medical kiosk, information about wait time for a medical kiosk, information as to the order of users waiting to use the medical kiosk, information about whether a medical kiosk is available or in use, cable TV, satellite TV, local broadcast TV, infomercial, medical programs, DVD materials, Blu-ray materials, video streaming, etc.). Generally, a user enters payment information at the registration station (e.g., swipes a credit or debit card, etc.); however, it can be appreciated that payment information can also or alternatively be entered inside the medical kiosk, at the optional attendant station, wirelessly or over a network via a smart phone or other device or by a computer connected to a network, etc. If an attendant is available, the attendant can assist a user during the registration process; however, this is not required. Generally, the medical kiosk includes a single registration station; however, this is not required. As can be appreciated, the registration station can alternatively be located inside the medical kiosk, at the attendant station, on other panels or sidewalls of the medical kiosk, or located remotely from the medical kiosk (e.g., central registration center for use with multiple medical kiosks, etc.).

Referring now to FIGS. 1 and 8-12, a non-limiting interior of the medical kiosk is illustrated. As previously discussed, the interior room or cavity of the medical kiosk can optionally include a scale 112, a bench 130 and/or a UV sanitizing system 220.

Figure 8:
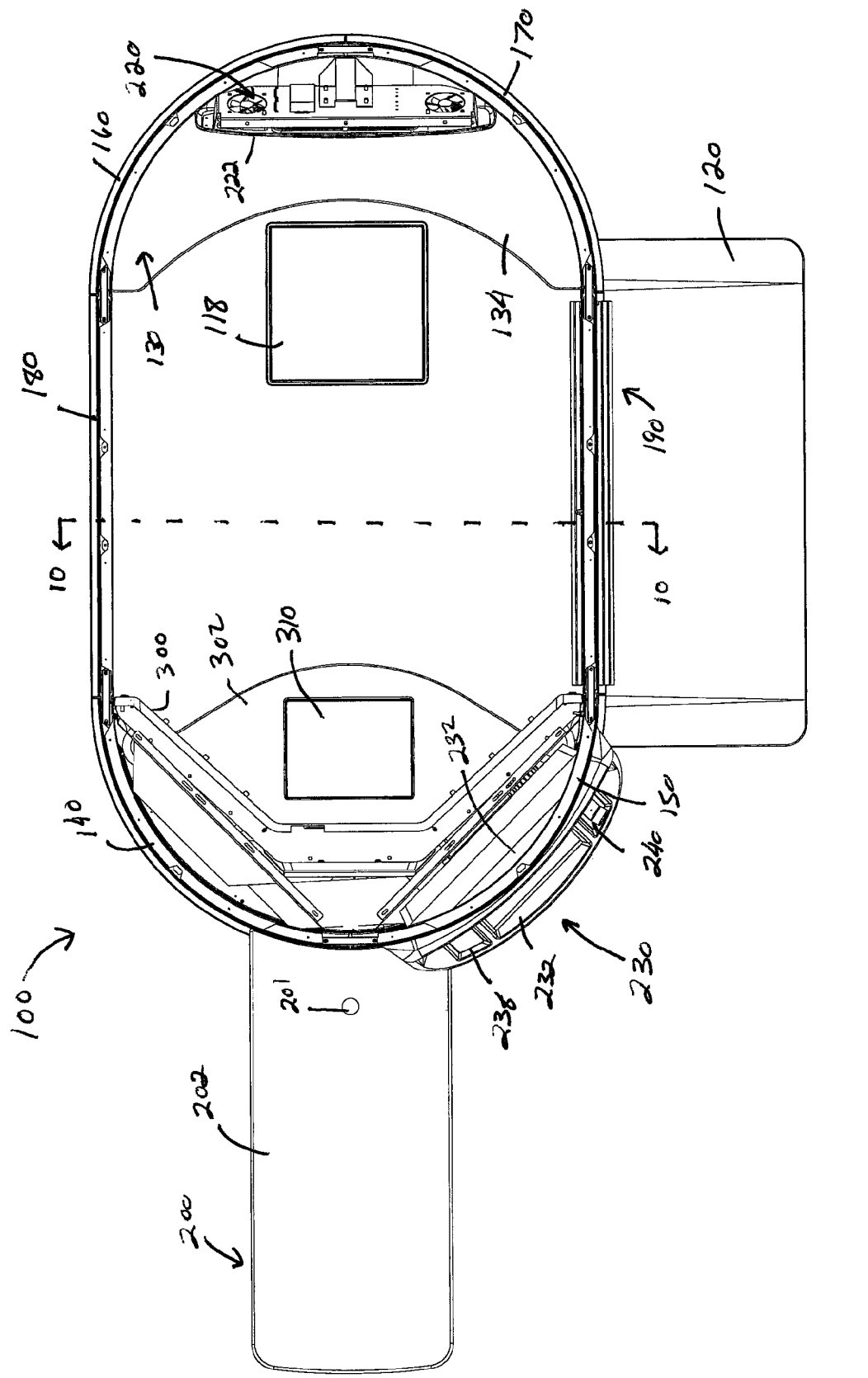
FIG. 8 is a top interior view of the medical kiosk of FIG. 1.
Figure 9:
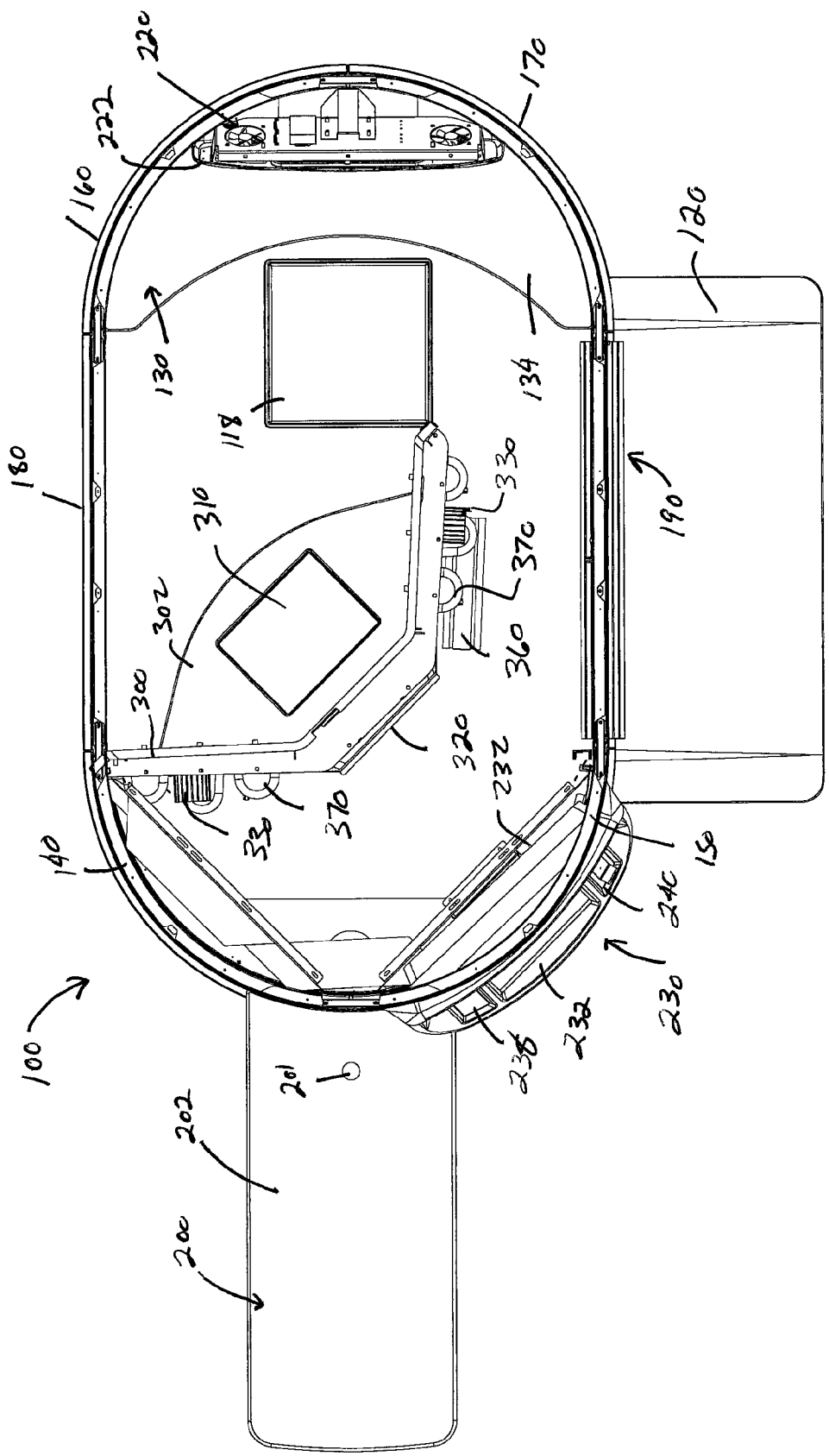
FIG. 9 is a top interior view of the medical kiosk of FIG. 1 that illustrates the front interior panel in the open position.

Referring now to FIGS. 8-11, a non-limiting interior front region of the medical kiosk is illustrated. The interior chamber of the medical kiosk includes a front interior panel 300. The front interior panel 300 can be connected to front panels 140 and/or 150. As illustrated in FIG. 9, the front interior panel can be pivotally connected to front panel 140 to enable the front interior panel to be moved away from front panel 150; however, this is not required. The movement of the front interior panel can be used to allow access to the components (e.g. computer, router, server, battery backup, harddrive, medical devices, electronic locks, fans, displays, speakers, camera, headphone jack, electronic scale, Bluetooth devices, lights, pumps, scanners, touch pad, ID verification devices, printer, etc.) that are located between front panels 140 and 150 and front interior panel 300; however, this is not required. Such access can be used to facilitate in the service, maintenance, upgrading, replacement, etc. of such components; however, this is not required. The front interior panel can include a lock; however, this is not required.

The front of the front interior panel can include a desk top 302 that is used to support one or more touch screens 310, touch pads or keyboards positioned on the desk top. The shape, thickness and size of the desk top are non-limiting. The desk top is illustrated as secured to or formed on the front interior panel 300; however, this is not required. The desk top can have one or more support legs, not shown; however, this is not required. The one or more touch screens, touch pads, keyboards, etc. on the desk top can be secured to the desk top; however, this is not required. The desk top is illustrated as sloping downward toward the front edge; however, this is not required. The size, shape and thickness of the one or more touch screens, touch pads, keyboards, etc. are non-limiting. The one or more touch screens, touch pads, keyboards, etc. are designed to be used by a user to enter various types of information (e.g., quality survey, patient history, patient medical information, payment information, questions to medical provider, vitals, etc.) before, during and/or after receiving medical services. As can be appreciated, the one or more touch screens, when used, can additionally or alternatively be used to provide information and/or instructions to the user and/or can provide other uses for the user (e.g., use policy, instructions on how to use the medical kiosk and/or medical devices, providing information on next step of medical visit, request assistance, increase/decrease speaker volume, increase/decrease headjack volume, focus medical devices, adjust volume of medical devices, adjust lighting in kiosk, etc.) during use of the medical kiosk; however, this is not required. The desk top can optionally include one or more other devices (lights, buttons, switches, camera, speakers, microphone, scanner, receiver, transmitter, credit card/debit card or other some other card reader, smart phone or other smart device reader/scanner, finger and/or eye scanner, shelf, printer, storage cavity, motion sensor, sound sensor, temperature sensor, logos, scanner, etc.); however, this is not required. A chair, not shown, can be provided to enable the user to sit when using the medical kiosk. The chair can be a free standing chair or be connected to the medical kiosk.

One or more monitors or display screens 320 can be positioned on the front of the interior front panel. As can be appreciated, one or more monitors or display screens can be positioned on other or additional locations in the medical kiosk. The shape, size and thickness of the one or more monitors are non-limiting. The monitor is generally used to view the one or more medical providers when the user is located in the medical kiosk. The one or more monitors can also or alternatively display other or additional information (e.g., instructions, questions, general medical information, time, output or results of examination of user, vitals information, results from the medical devices, advertisements, information about the medical kiosk, information being displayed and/or entered by the user on the touchscreen, etc.).

One or more cameras (e.g., video camera, etc.) can be positioned on the interior wall panel and/or be embedded in the one or more monitors or display screens 320. As can be appreciated, one or more cameras can be positioned on other or additional locations in the medical kiosk. The one or more cameras enable pictures of the user in the medical kiosk to be transmitted to a remotely located medical provider. The remotely located medical provider also typically includes a camera at his/her location so that pictures of the medical provider can be transmitted to the one or more monitors or display screens 320 in the medical kiosk. Such an arrangement can allow for real-time or near real-time video conferencing between the user and medical provider while the user is located in the medical kiosk. The one or more cameras can have other or additional functions (e.g., determine height of user when standing on scale or other locations in the medical kiosk, view one or more regions of user so as to provide a medical examination of the user in the medical kiosk, monitor occupancy of the medical kiosk, provide security monitoring for the medical kiosk, etc.). The one or more monitors or display screens 320 in the medical kiosk can also be used to replay one or more portions of the video conference between the user and medical provider after the secession with the medical provider has ended; however, this is not required. Such a feature, when available, enables the user to review or again listen to instruction, advice, etc. provided by the medical provider to the user. This video playback feature, when available, can be limited to being viewed by the user while the user remains in the medical kiosk, or can also or alternatively be accessed be the user after the user exits the medical kiosk; however, this is not required. If the user can optionally access the recorded video conference outside the medical kiosk, the video file can 1) be accessed from some central server, 2) electronically sent to a personal computer, mobile device, tablet, laptop, etc., and/or 3) mailed to the user (e.g., DVD, Blu-ray disk, video tape, USB jump drive, etc.).

One or more speakers 330 can be positioned on the front interior panel of the medical kiosk. As can be appreciated, one or more speakers can be positioned on other or additional locations in the medical kiosk. The speakers can be used to enable a user in the medical kiosk to listen to what the medical provider is saying to the user. One or more microphones are generally included in the medical kiosk to enable the user to verbally communicate with the medical provider. The medical kiosk can optionally include a braille keyboard and/or reader to enable the visually and/or hearing impaired to communicate with a medical provider while in the medical kiosk. The speakers can also or alternatively be used to play background music, sound an alarm, etc. A headphone jack 340 can be provided on the interior front panel and/or other locations in the medical kiosk to enable headphones to be connected to the medical kiosk; however, this is not required. The interior front panel and/or other locations in the medical kiosk can include one or more data ports (e.g., UBS, Ethernet, Firewire, etc.) to enable medical devices, storage devices, smart phones, computers, tablets, and/or other devices to be connected to the medical kiosk; however, this is not required. For example, the data port could be used by a patient, to download and/or upload information to a medical device on a patient (e.g., heart monitor, heart pacemaker, implantable cardioverter defibrillators, etc.).

The front interior panel 300 can optionally include one or more air vents 350. The one or more air vents, when used, can enable air to enter or exit an interior location positioned between the front wall panels and the front interior panel to thereby provide circulation in the medical kiosk. Such interior location can include one or more fans to draw air through the one or more vent and into the interior location; however, this is not required. As illustrated in FIGS. 8 and 8, the interior location can include a computer 360, a router, a server, a battery backup, a harddrive, medical devices, electronic locks, displays, speakers, camera, headphone jack, Bluetooth devices, lights, pumps, devices, printer, etc. Such devices can generate heat during operation, thus the air flow can be used to provide cooling for such devices.

Figure 10:
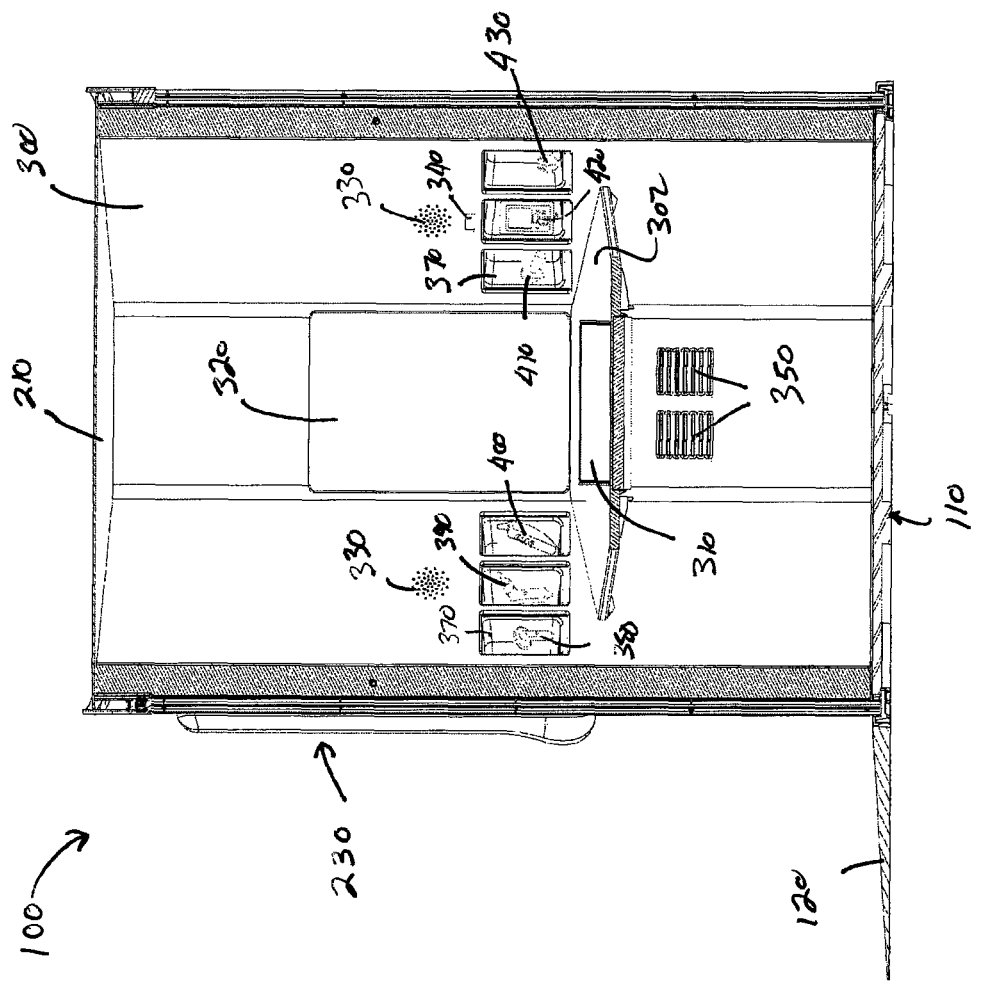
FIG. 10 is a cross-section view along line 10-10 of FIG. 8.
Figure 11:
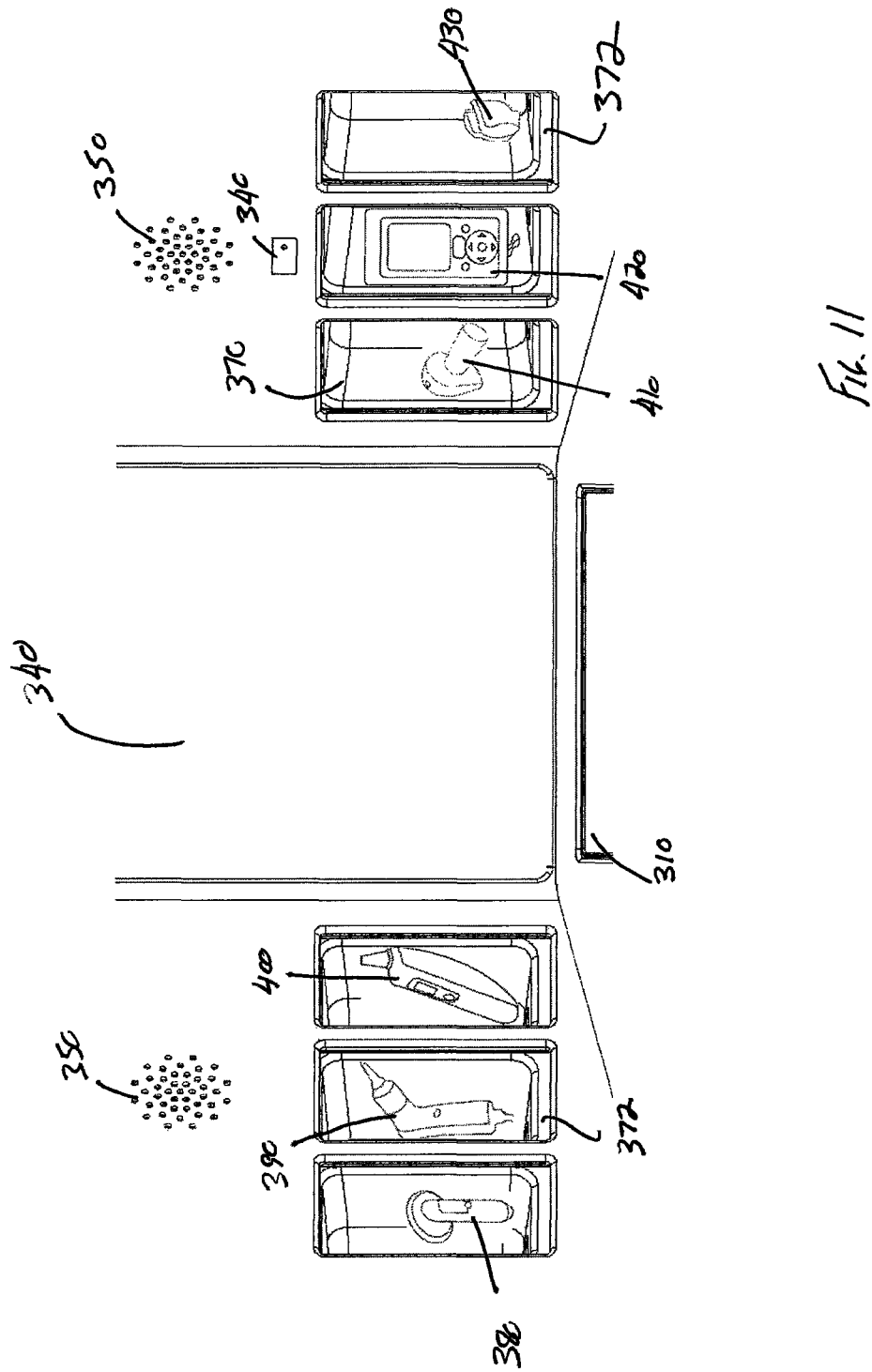
FIG. 11 is an enlarged view of the medical cabinets of FIG. 10.
Figure 12:
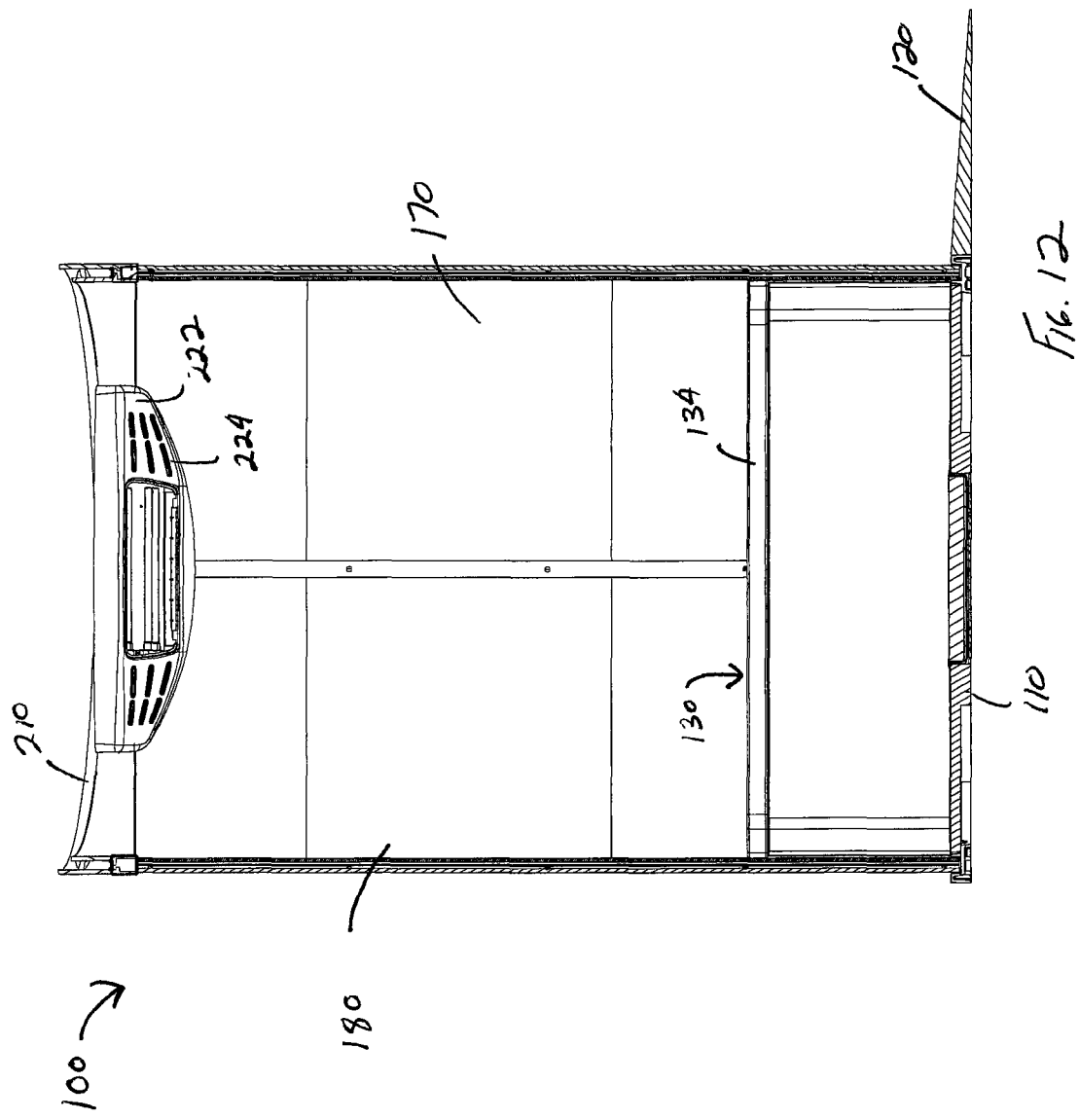
FIG. 12 is a cross-section view along line 10-10 of FIG. 8 viewed from the opposite direction; and, FIG. 13 is a front view of another embodiment of the medical kiosk.

The front interior panel can include one or more equipment chambers 370 can be positioned on or near the front interior wall. The equipment chambers are used to store one or more medical devices (e.g., stethoscope, otoscope, thermometer, dermascope, spirometer, pulse oximeter, heating pad, magnifying glass, tongue depressor, tweezers, blood glucometer etc.). The one or more equipment chambers can also or alternatively be used to include other types of materials (e.g., tissue, Band-Aid, gauze, cotton ball, disinfecting wipe, cortisone cream, anti-biotic cream/ointment, cotton swab, fabric wrap, etc.). The one or more equipment chambers generally include a door 372 to limit access to the one or more equipment chambers; however, this is not required. The door, when used, can be manually openable/closeable, and/or the doors can be controllably opened/closed remotely by the medical provider and/or attendant. Generally, the doors are controllably opened and/or unlocked by the medical provider during the examination of the user in the medical kiosk. After the user has left the medical kiosk, the attendant can enter the medical kiosk, and then clean the medical equipment that was handled or used by the prior user and/or dispose of and/or replace items that were used and/or handled by the prior user. Thereafter, the attendant can restock, replace, and/or reposition the medical equipment and/or non-medical equipment in the equipment chambers and close the equipment chamber doors prior to the next user entering the medical kiosk. One or more types of medical equipment can be designed to transmit information by wire or wirelessly to electronic components in the medical kiosk and/or to the remotely located medical provider. As illustrated in FIGS. 10 and 11, six equipment chambers having doors are included in the medical kiosk, three on each side of the desk top 300. As can be appreciated, a larger or smaller number of equipment chambers can be used. As also can be appreciated, some or all of the equipment chambers can be absent doors. The doors on the six equipment chambers are designed to be unlocked and/or opened remotely by the medical provider and/or during the taking of vitals by the patient. The doors are designed to automatically lock closed when the doors are closed by the attendant after the user has left the medical kiosk; however, this is not required. Each of the six equipment chambers is designed to include a different piece of medical equipment, namely a stethoscope 380, an otoscope 390, a thermometer 400, a dermascope 410, a spirometer 420, and a pulse oximeter 430. As can be appreciated, a larger or smaller number of medical equipment can be used in the medical kiosk and/or different types of medical equipment can be included in the medical kiosk.

Figure 13:
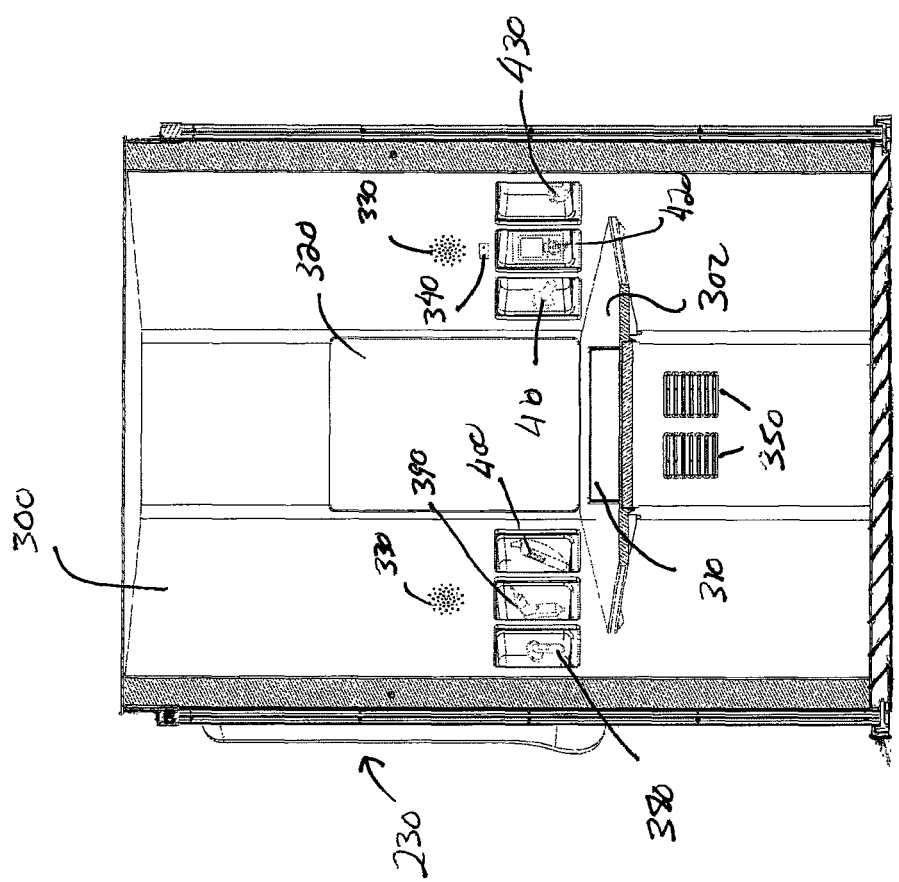

Referring now to FIG. 13, there is illustrated an alternative configuration for the medical kiosk 100 of the present invention. In this embodiment, floor 110, doors 190, panels 140, 150, 160 and 170, ceiling 210, ramp 120, bench 130 and UV sanitizer 220 are absent from the medical kiosk. The attendant desk 200 may also be absent. In this non-limiting arrangement, the medical kiosk 100 can be placed in a private room and/or some other location. The medical kiosk includes a registration station 230 that can be the same or similar as the registration station described above. The medical kiosk can include front wall panels 140 and 150 or a single wall front wall panel. The medical kiosk includes interior front panel 300 which can be the same or similar to interior front panel 300 as described above in FIGS. 1 and 8-11. The interior front panel can be pivotally connected to the one or more front wall panels; however, this is not required. The interior front panel may or may not include a Physician Screen 340. If interior front panel is the same or similar to interior front panel 300 as described above in FIGS. 1 and 8-11, then the user can have a teleconference with a medical provider. However, if interior front panel does include a Physician Screen 340 and one or more other components (e.g., speakers 330, headphone jack 340, etc.), then the user may only be able to collect one or more vitals and then proceed to another location to visit a medical provider. As can also be appreciated, the medical kiosk can also be absent the desk top, medical device compartments, Patient Screen and the like such that the medical kiosk primarily includes the registration station 230 to enable a user to check-in for a visit with a medical provider. As can be appreciated, one or more features of the medical kiosk of the present invention can be used in other ways to provide medical services to a user.

The medical kiosk and method for using the medical kiosk are a novel and advanced healthcare delivery system wherein patients and physicians can engage in real-time interactive consultations, providing convenient and affordable healthcare services. The medical kiosk includes the latest technologies in medical devices, video conferencing, and VoIP telephony so that the medical kiosk can extend traditional healthcare to convenient retail pharmacy locations or other locations in a user's neighborhood, therein enabling a user to see a medical provider and obtain a prescription, if required, in a fast and convenient manner.

Some advantageous aspect of the medical kiosk and medical method are:
  Patient Portal (Cloud Based).
  Provider Portal (Cloud Based).
  Integrated Care Station.
  Facilitates Efficient Delivery of Basic Healthcare Delivery.
  Automates All Aspects of a Check Up.
  Easy Check-In.
  Vital Signs Capture.
  Prescription Generation.
  Post Care and Outcomes.
  Convenient Locations Where Consumers Want To Be.
  Video playback of the recorded session between the user and medical provider.

The medical kiosk and medical method can be used to provide primary and/or urgent care services in four (4) simple steps:

Step 1—Patient begins/completes check-in process via web portal or at the medical kiosk. The patient can optionally begin the check-in via web portal and then later complete check-in process at the medical kiosk; however, this is not required. A medical provider can send a reminder to patient regarding an appointment and/or begin the check-in process for a patient (e.g., follow-up appointment, etc.); however, this is not required.

Step 2—Medical provider receives eligible request and accepts and/or is assigned to patient.

Step 3—Patient visits the medical kiosk and has a private appointment with a doctor via the Patient Screen.

Step 4—Visit is completed. The medical kiosk and/or medical provider can then provide additional care/services that include: prescription, billing information, education, referrals, follow up and/or EMR/PHR entry. The medical provider can cause the medical kiosk to printout a prescription and/or directly send the prescription request to a pharmacy. The medical kiosk can print out a bill after the medical services are provided and/or accept payment prior to or after medical services are provided. The medical kiosk can be designed to accept and/or process medical insurance information provided by the user. The medical kiosk can print out and/or display education materials/information relevant to/requested by the user and/or provided by the medical provider. The medical kiosk and/or medical provider and/or attendant can schedule a follow-up visit for the user. Email, twitter, Facebook, test, and/or mail reminders can be sent to the user regarding scheduled and/or follow-up visits. The medical provider and/or attendant can schedule a visit with another medical provider and/or admit the user to the hospital, contact an ambulance, etc. during or after the visit to the medical kiosk. A visit summary can be printed out and/or sent to the patient. As can be appreciated, the medical kiosk and method for using the medical kiosk can have other or additional features.

Advantageous portal features of the medical kiosk and associated medical method are:
  Practice Management Engine.
    Appointments Scheduling Engine.
    Online Eligibility, Claims, and Billing Engine.
    ePrescribing with Alerts and Reminder Engine.
    Medical Records Interface and Access.
      Personal Health Record (PHR).
      Electronic Medical record (EMR).
      Rules-Based Care Plans.
      Rules-Based Education.

Check In Pathway to Care Engine.
Secure Video Conferencing Engine.
Documentation Module.
　Appointment Storage and Analysis.
Education and Post Care.

Some non-limiting advantages to patients by use of the medical kiosk and medical method are:
　Convenient.
　　Closer to home.
　　Saves time.
　　Language and culture friendly.
　Better Access.
　　Personal doctor available while traveling.
　　Larger selection of doctors.
　　Not limited by doctor's visitation schedule.
　More Accurate.
　　Review record of appointment.
　　Automatic data entry into PHR.
　Less Exposure to Illness.

Some non-limiting advantages to medical providers by use of the medical kiosk and medical method are:
　Higher Revenues.
　　More appointments/day.
　　Less traveling.
　More Accurate.
　　Review record of appointment.
　　Automatic data entry into EMR/HER.
　Integrated Care.
　　Referral and transfer.
　Load Balancing.
　Appointment load can be shared with other doctors regardless of location.

Some non-limiting advantages to payers by use of the medical kiosk and medical method are:
　Change in Status.
　　Transition from Payer to Provider.
　Market Leverage.
　New Business Model.
　Call Center based Nurse Practitioner.
　Efficiency.
　　Market Demand.
　　Less Overhead.
　　Scalability.
　　Less Liability.

The medical kiosk of the present invention is an Integrated Care Terminal that is a highly equipped doctor's office that is built and designed to deliver urgent and minor medical care in the field utilizing a centralized team of doctors for the evaluation and treatment of patients. The medical kiosk can be fitted with the latest FDA approved medical devices used by doctors today.

Employing the latest technology that is used in physician offices and emergency rooms, the medical kiosk is able to allow patients to obtain appropriate care in locations that are convenient, accessible, and more affordable.

The medical kiosk is designed to be a comfortable, self-contained, secure, sanitary, soundproof kiosk that is approximately 5 feet wide and 9½ feet long; however, it can have other dimensions. The medical kiosk can be made of extruded plastics and related components. The interior of the medical kiosk can contain one or more of the following integrated medical devices:
　Thermometer (e.g., temperature taken via ear, temperature taken via ear, IR thermometer to scan head or other area of body, etc.).
　Scale built into the patient seat or floor for measuring the patient's weight.
　Otoscope—for examining the middle ear, exterior ear, nasal passages, mouth and throat.
　Oximeter which measures the blood oxygen saturation.
　Stethoscope for evaluation of heart, lung and bowel sounds.
　Blood Pressure Cuff to measure blood pressure.
　EKG which provides a snapshot of the heart rhythm and data regarding stress or injury to the heart muscle.
　Spirometer and transducer for measuring lung function.
　Blood glucose measuring device or monitor.
　Retinal scan device (e.g., Itronix retinal scan device, etc.).
　Dermascope.

A medical attendant (e.g., medical assistant, nurse assistant, nurse, nurse practitioner, physician, etc.) who resides outside the medical kiosk can be responsible for answering user questions, assisting with user registration/payment, thoroughly clean the medical kiosk after each use, and restock and/or reset the medical kiosk after each use. The cleaning of the medical kiosk can include sanitizing the seat, touch screen, floor, walls, seat, and all instruments as well as ensuring the medical kiosk is free of debris and any patient belongings. The medical kiosk can also be designed to be automatically sterilized after one or more users use the medical kiosk by utilizing a chemical mist sterilization technology and/or UV sterilization technology. The medical attendant can also ensure that any insurance forms required by the user/patient for reimbursement are provided via a printer or some other means contained in the exterior and/or interior of the medical kiosk.

The medical kiosk can also contain one or more computers, which are connected to the internet and powers the one or more monitors and/or other type of equipment in the medical kiosk; however, this is not required. The exterior monitor on the medical kiosk can be used for patient registration and appointment selection that can be conducted in a touch screen format.

The method for providing medical services via a medical kiosk regarding protocols for scheduling, diagnosing, delivering and documenting telemedicine primary care can include:

a. Medical Provider Application—this application is used by the medical provider to provide clinical services. The application contains all that the medical provider requires to diagnose, deliver care and document the clinical episode. It runs on the physician's computer and can be integrated with the leading EMR applications.

b. Patient Application—this application is used by the patient to register with a medical kiosk and also captures the patient's medical history and/or vitals. It includes all the information required to administer clinical services to the patient. This includes financial/billing information and a Healthspot Electronic Medical Record (EMR), which can be accessed by the patient and the medical providers.

c. Integrated videoconferencing software—this application supports the live patient-clinician interaction required for delivery of the clinical services. It uses a secure connection to the servers and the provider via an internet connection.

To use a medical kiosk, the users/patients may go through one or more of the following steps:

a. Go Online, register and schedule an appointment at the nearest terminal or walk-in and register at the medical kiosk.

b. Use the scheduling engine to select an appointment time.

c. Input insurance, preferred pharmacy location and/or billing information, and remit payment.

d. Complete pre-appointment pathway to care.

e. Visit a medical kiosk and see a medical provider via the integrated care terminal.

f. Pick up prescription, if indicated, at the pharmacy of choice.

g. Optionally use website to manage user's care until user is better.

The following example is a non-limiting example as to what one user may encounter when using the medical kiosk of the present invention:

Jane Doe is not feeling well, suffering from severe nasal congestion and "cold symptoms" for several days. She realizes she should seek care, but finds it frustrating to schedule an appointment with her primary care physician and knows that this is not an appropriate reason to visit her local ER. However, she recently became aware of a medical kiosk in her neighborhood grocery store, and decides to drive to the store a few minutes from her home to see if she can get a walk-in appointment. Upon arrival, Jane is met by the attendant who helps her register at the exterior of the medical kiosk for the next available appointment in a few minutes. She completes the basic information about her medical condition in a short guided questionnaire via the monitor on the exterior of the terminal. The intake questionnaire captures demographic information that can include some or all of the following information: name, address, gender, race, native language, age, birthdate, fingerprint, simple medical history/medications, current symptoms, allergies, medical condition, medications currently used, preferred pharmacy, insurance information, and a debit/credit card payment and/or some other types of payment for the visit, and/or time of next available visit in kiosk. Information is gathered and stored securely to facilitate future visits. Jane then has a seat at a small waiting area near the medical kiosk. When the appointment prior Jane's ends by another user, Jane witnesses the attendant cleaning the appropriate surface areas of the interior of the medical kiosk, and the changing the protective covers of the instruments that were used.

Jane then proceeds to check-in to the kiosk by providing a password or some other type of ID. This check-in can occur with the registration station on the kiosk and/or with the medical attendant. Once checked-in, the medical attendant escorts the patient into the medical kiosk. The medical assistant also fits a blood pressure cuff on the patient, connects the blood pressure cuff to the medical kiosk, and then begins the vital capture process for the patient. The medical attendant may or may not be present during the complete vitals capture process. During the vitals capture process, the weight and temperature of the patient is also collected. The Patient Application provides information to the patient on how to proceed with the vitals capture process. Once the vital capture process is completed, the patient presses a button or indicates in some other manner that the patient is ready to proceed with the teleconference with the medical provider. During the vitals capture process, the medical provider can view Jane's medical history, current medications, symptoms and/or any other information that Jane's entered during the registration process. The medical provider can also view the results of the vitals that were captured during the vitals capture process. Once the medical provider receives information that the patient is ready for the teleconference, the medical provider selects the option to create such connection. The medical provide then appears on the Provider Screen in the medical kiosk and the patient appears on the screen being used by the medical provider. The medical provider can then question and examine Jane during the teleconference.

After the medical provider has spoken to Jane, he suspects a possible sinus infection. The medical provider then clicks on a button on the Provider Application which causes a door to a medical device cavity or compartment on the medical kiosk to open for the otoscope. The medical provider then instructs Jane to gently insert the device in her nose and takes a picture of her nasal mucosa. The picture is displayed on the medical provider's screen and optionally displayed on the Patient and/or Provider screen in the medical kiosk for Jane to see. The medical provider proceeds to instruct Jane to use the instrument to look in her ears and throat. The medical provider views the pictures and determines that the throat and nasal passages are inflamed which is indicative of an upper respiratory infection. Based on her symptoms and the examination, the medical provider tells Jane he believes that she has a sinus infection.

The medical provider can optionally prescribe a prescription for the appropriate antibiotic which can be e-prescribed by the medical provider and sent electronically to the pharmacy of Jane's choice, which in this case happens to be the pharmacy within the grocery store. Prior to or after Jane exits the medical kiosk, Jane may take a survey of the visit. Jane may optionally complete an insurance form from the attendant, which she can use to file with her insurance company for reimbursement. Jane then walks over to the pharmacy and waits on her prescription, which is available ten minutes later. She returns home and begins taking the medication to cure her sinus infection.

Some of the non-limiting features of the medical kiosk are:
Integrated Medical Devices.
Exterior Check-In Station.
Patient Waiting Area.
Integrated Wi-Fi Hot Spot.
Touch Screen User Interface.
HIPAA Compliant Design.
Instant Sterilization.
Video/Audio Conferencing.
Flexible Access.
   Handicap.
   Parent and Child.
Modular design for Pharmacy door deployment.
Small Footprint.
Fully Integrated Interior Design.
Expandable Device Rail.
Secure PC storage with access.
Open design feels comfortable.
Payment and Signature.
Finger Print Reader.
Integrated Printer.
Integrated Medical Devices.
   Thermometer—(e.g., temperature taken via ear, temperature taken via ear, IR thermometer to scan head or other area of body, etc.
   Scale built into the patient seat or floor for measuring the patient's weight.
   Otoscope—for examining the middle ear, exterior ear, nasal passages, mouth and throat.
   Oximeter which measures the blood oxygen saturation.
   Stethoscope for evaluation of heart, lung and bowel sounds.
   Blood Pressure Cuff to measure blood pressure.
   EKG which provides a snapshot of the heart rhythm and data regarding stress or injury to the heart muscle.
   Spirometer and transducer for measuring lung function.
   Blood Glucose measurement device and/or monitor to measure blood glucose levels.
   Retinal scan device to view structures in the eye.
   Dermascope to view the skin and/or throat.
Exterior Check-In Station—A monitor and keyboard is generally mounted on the outside of the medical kiosk to allow for new user/patient registration and check in. The station can be designed to take payment and/or a fingerprint. The station generally is located away from the entrance to the medical kiosk to allow a degree of separation from the patient inside the medical kiosk. The attendant can use this station for her work.

Patient Waiting Area—Can include a small area to put a few chairs outside the medical kiosk to act as a waiting area.

Integrated Wi-Fi Hot Spot—In order to minimize network connection cost, a Wi-Fi hot spot can partner with an ISP of choice (AT&T, Verizon, Sprint, T-Mobile, etc.).

Touch Screen User Interface—The patient can be allowed to interact while inside the medical kiosk by use of a touch screen interface.

HIPAA Compliant Design—HIPAA requires patient information to be secure. This will mean the medical kiosk will generally be sound proof and a passerby cannot see in and see any patient information. The medical kiosk generally is fully enclosed and lockable, but can allow exterior access in case of emergency.

Instant Sterilization—Because of the many germs and other contaminants that will be inside the medical kiosk, a sterilization technology can be used in the medical kiosk. One type of sterilization system that can be used is a built-in sanitizing misting system that dispenses from a series of misters between every appointment. Another or additional sterilization system that can be used is a UV lighting system that can be blasted between appointments. Other techniques and technologies can also or alternatively be used. The attendant can have the ability to activate one or more sterilization systems (e.g., via button, computer, etc.). The attendant can be required to keep track of records about the sanitization process and can ensure that the doors to the medical kiosk are closed/locked during the sterilization process.

Video/Audio Conferencing—The patient will communicate with the medical provider via video and audio conferencing technology. This environment can make the patient feel as close to the medical provider as actually being present as possible. A two-way glass can be used to place the camera in the center of the monitor to keep the patient looking head on, versus the Skype and current video conferencing solutions that keep users looking at the camera and back to the monitor.

Flexible Access—The medical kiosk should have a large enough door to accommodate a wheel chair. It should also be large enough inside to allow a parent to sit with a child and not feel constrained.

Modular design for Pharmacy door deployment—Most Pharmacies today only have a standard door. The medical kiosk is built in a manner that allows it to enter through the door and quickly be assembled.

Small Footprint—Because of the cost of retail space, the medical kiosk will be small enough to fit in most locations (e.g., 4-6 ft. wide and 7-10 ft. length).

Fully Integrated Interior Design—The interior of the medical kiosk can be designed to be cleaner, sleeker, nicer, more luxurious, than the experience they get at the average doctor's office.

Expandable Device Rail—The medical kiosk can include the latest medical devices and update such medical devices in a more rapid manner than the average doctors' office. The medical kiosk can include a mounting rail type system that allows medical devices in the medical kiosk to be easily accessed by the user. An indicator, such as a light, can be used to notify which medical device is to be used by the user.

Secure PC storage with access—Because uptime of the software is so important, electronics can be inserted in a compartment in the medical kiosk. Such area generally should be secure, cooled, and easily accessible for service.

Open design feels spacious—The medical kiosk is generally designed to feel bigger than it is such as by providing a glass window that wraps around the back half of the kiosk.

Payment and Signature—The medical kiosk can include an integrated credit card swipe for payment, and a signature pad for medical authorization.

Finger Print Reader—A finger print reader can be included on the medical kiosk to confirm patient ID under HIPAA.

Integrated Printer—An integrated printer can be included in the medical kiosk to print medical and insurance forms and/or receipts and/or prescription. The printer can also print coupons based upon diagnosis to promote product sales. Our software can be included to inform the attendant of low paper in the paper.

Video Playback—The recorded medical session can be partially or fully reviewed by the user to enable the user to again listen to information, instructions and/or advise from the medical provider. As can be appreciated, the video playback feature can also or alternatively be used for auditing purposes, compliance purposes, security purposes, quality control purposes, etc.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A medical kiosk configured to provide tele-med services to a user, said medical kiosk including an internal enclosure having a front section, a user video conferencing system and a plurality of medical devices, said user video conferencing system configured for the user to have a real-time or near real-time tele-conference with a medical provider located remotely from said medical kiosk, said user video conferencing system including a first and second video screens, a camera, and a microphone, said first video screen configured to display said medical provider during a video conference between said user and said medical provider, said second video screen being a touch screen configured for said user to provide information regarding said tele-med services, said first and second video screens and said camera are located at a front section of said enclosure, said plurality of medical devices is configured for use by the user to provide information to the medical provider about the user to enable the medical provider to provide real-time or near real-time medical advice to the user while the user is in said enclosure, said enclosure includes a plurality of remotely controlled medical compartments, each of said remotely controlled medical compartments includes at least one of said medical devices, each remotely controlled medical compartment including one of said medical devices that is different from any other of said medical devices located in any other of said remotely controlled medical compartments, each of said remotely controlled medical compartments includes a movable and lockable door that limits access to said at least one medical device in said medical compartment, said door moveable between a closed position and an open position, said closed position of said door limiting access to said medical device in said remotely controlled medical compartment, said open position providing access to said medical device in said remotely controlled medical compartment, each of said doors on each of said remotely controlled medical compartment is selectively unlockable by said medical provider to cause said door to move from said closed position to said open position.

2. The medical kiosk as defined in claim 1, said plurality of medical devices including two or more devices selected from the group consisting of a stethoscope, an otoscope, a thermometer, a dermascope, a spirometer, blood pressure cuff, a pulse oximeter, a heating pad, a magnifying glass, a tongue depressor, tweezers, a blood glucometer, an audiometer, and a 3-lead EKG.

3. The medical kiosk as defined in claim 1, wherein at least one said remotely controlled medical compartments is unlockable as the user progresses through a vitals capture program.

4. The medical kiosk as defined in claim 1, wherein including a floor scale.

5. The medical kiosk as defined in claim 1, wherein including a headphone jack.

6. The medical kiosk as defined in claim 1, including a mobile device application or network application, said mobile application or network application configured to provide the user access to various functions on a mobile device or computer, said functions in including one or more functions selected from the group consisting of 1) locating an available medical kiosk, 2) scheduling an appointment with the medical kiosk, 3) pre-registering symptoms for visit, 4) setting an appointment with the medical kiosk, 5) receiving reminders regarding appointments for the medical kiosk, 6) obtaining information about medical kiosk availability, 7) obtaining information about certain medical provider availability, 8) obtaining information about available medical providers, 9) selecting a certain medical provider, 10) obtaining map information regarding a selected medical kiosk, 11) locating the closest kiosk for an appointment with a certain medical provider in a certain field of medicine, 12) presubmitting medical insurance, 13) submitting payment information, 14) receiving information on payment status, 15) receiving information on insurance coverage, 16) receiving updates regarding appointment regarding appointments for the medical kiosk, 17) receiving prescription information, 18) submitting payment information for prescriptions, 19) answering surveys regarding the use of the medical kiosk, 20) receiving medication reminders, 21) pre-registering reasons for visit, 22) canceling an appointment with the medical kiosk, 23) selecting a certain medical provider in a certain field of medicine, 24) providing address information regarding a selected medical kiosk, 25) obtaining hours of operation information regarding a selected medical kiosk, 26) locating the closest kiosk for an appointment with a certain medical provider, 27) locating the closest kiosk availability for an appointment with a certain medical provider in a certain field of medicine, 28) locating the closest kiosk availability for an appointment with a certain medical provider, and 29) preclearing medical insurance.

7. The medical kiosk as defined in claim 1, including a medication adherence software application configured to provide the user access to one or more functions selected from the group consisting of 1) speaking to a pharmacist, 2) changing the user's medications alerts, 3) obtaining information about certain types of medical conditions, 4) checking medication orders status, 5) checking medication delivery status, 6) refilling prescriptions, 7) transferring prescriptions to a another location, 8) obtaining information about recommended medication dosages, 9) obtaining information about recommended times to take medications, 10) obtaining information about recommended frequency for taking medications, 11) obtaining information about medications, 12) obtaining information about generic brands available for medications, 13) requesting an appointment to speak with the medical provider, 14) entering information regarding compliance information regarding medication usage by user, 15) receiving compliance reports for users regarding medication usage, 16) paying for a prescription, 17) selecting between a generic and non-generic brand of medication, 18) comparing pricing options for medications, 19) providing reminders for users to take their medications, 20) monitoring progress reports regarding the user's adherence to medication usage, 21) enrolling the user in an electronic prescriptions network which sends their prescriptions to their choice of pharmacy, 22) comparing delivery options for medications, and 23) generating progress reports regarding the user's adherence to medication usage.

8. The medical kiosk as defined in claim 1, includes an exterior registration station located external to said internal enclosure, said registration station including a user input system that enables the user to enter information about the user prior to having said real-time or near real-time tele-conference with the medical provider, said user input system including one or more components selected from the group consisting of a key pad for identification, a key pad for data entry, key board for identification, a key board for data entry, a touch screen for identification, a touch screen for data entry, a microphone and voice recognition software for identification, a microphone and voice recognition software for data entry, a fingerprint scanner for identification, a fingerprint scanner for data entry, a retina scanner for identification, a retina scanner for data entry, camera, speaker, card reader, smart device reader/scanner, motion sensor, sound sensor, and temperature sensor, said registration station configured to provide the user access to one or more functions selected from the group consisting of a) entering the user's name, b) entering the user's address, c) entering the user's contact information, d) entering the user's age, e) entering the user's sex, f) entering the user's height, g) entering the user's weight, h) entering the user's race, i) entering the user's language, j) entering the user's medical history, k) entering medicines used by user, l) entering information on past medical condition, m) entering reason(s) for visit by the user, n) entering user's current symptoms, o) entering user's allergies, p) entering user's ID information, q) entering user's insurance information, r) entering user's payment information, s) entering consent information, t) requesting assistance from a medical attendant, u) entering date the user desires an appointment, v) entering user's current medical provider, w) requesting a specific medical provider, x) providing information to the user about the medical kiosk, y) providing information to the user on how to use the medial kiosk, z) providing information to the user on how to properly input/convey information to the medical kiosk, aa) providing the user information during the inputting/conveying of information by the user to the medical kiosk, bb) providing the user information on the wait time for the user's use of the medical kiosk, cc) providing the user with a number of other users waiting to use the medical kiosk, dd) providing the user with information regarding whether the medical kiosk is in use or is available, ee) entering time the user desires an appointment, and ff) requesting a medical provider having a particular medical specialty.

9. The medical kiosk as defined in claim 1, includes a display screen located external to said internal enclosure that can be used to provide one or more types of information selected from the group consisting of advertising information, information about the medical kiosk, information about wait time for the medical kiosk, information as to the order of users waiting to use the medical kiosk, information about whether a medical kiosk is available or in use, cable TV shows, satellite TV shows, local broadcast TV shows, infomercials, medical programs, DVD materials, Blu-ray materials, video programs, YouTube programs, and pictures, said display configured to only display information and to not accept data entry from the user.

10. The medical kiosk as defined in claim 1, said internal enclosure including a cleaning or sanitizing system to clean or sanitize at least a portion of said internal enclosure, said cleaning or sanitizing system including a system selected from the group consisting of a UV system and a mist system.

11. The medical kiosk as defined in claim 1, including a prescription drug system configured to provide the user access to one or more functions selected from the group consisting of 1) obtaining generated prescriptions from the medical provider, 2) ordering drugs, 3) selecting name brand and generic drugs, 4) selecting the supply quantity for the prescription, 5) the selection method by which the user will obtain a prescription 6) entering the user medical insurance for partial or full payment of the prescription, 7) entering the user's credit or debit card information to pay for the prescription, 8) entering the user's information for mail delivery of the prescription, 9) providing reminders to the user regarding medication refills, 10) providing notifications to the user when prescription has been mailed, 11) selecting the pharmacy where the user would like to pick-up the prescription, 12) providing reminders to the user regarding follow-up medical visits, and 13) providing notifications to the user when prescription is ready to be picked-up at the pharmacy.

12. The medical kiosk as defined in claim 1, including a moveable interior panel to allow access to one or more components located behind the moveable panel located in said internal enclosure, said one or more components including components selected from the group consisting of 1) electronics located behind the exterior check-in station, 2) electronics located behind the first and second video screens and 3) electronics used for network communication.

13. A method for providing a real-time or near real-time tele-conference with a medical provider located remotely from a medical kiosk and a user located at the medical kiosk, said method comprising the steps of:
 a. providing a medical kiosk, said medical kiosk including an internal enclosure having a front section, a user video conferencing system and a plurality of medical devices, said user video conferencing system configured for the user to have a real-time or near real-time tele-conference with a medical provider located remotely from said medical kiosk, said user video conferencing system including a first and second video screens, a camera, and a microphone, said first video screen configured to display said medical provider during a video conference between said user and said medical provider, said second video screen being a touch screen configured for said user to provide information regarding said tele-med services, said first and second video screens and said camera are located at a front section of said enclosure, said plurality of medical devices is configured for use by the user to provide information to the medical provider about the user to enable the medical provider to provide real-time or near real-time medical advice to the user while the user is in said enclosure, said enclosure includes a plurality of remotely controlled medical compartments, each of said remotely controlled medical compartments includes at least one of said medical devices, each remotely controlled medical compartment including one of said medical devices that is different from any other of said medical devices located in any other of said remotely controlled medical compartments, each of said remotely controlled medical compartments includes a movable and lockable door that limits access to said at least one medical device in said medical compartment, said door moveable between a closed position and an open position, said closed position of said door limiting access to said medical device in said remotely controlled medical compartment, said open position providing access to said medical device in said remotely controlled medical compartment, each of said doors on each of said remotely controlled medical compartment is selectively unlockable by said medical provider to cause said door to move from said closed position to said open position;
 b. providing one or more applications selected from the group consisting of an attendant application, an appointment application, a provider application, a schedule application, a patient portal application, medical adherence application, an administrator application, and a provider portal application; said attendant application includes software and/or hardware configured for an attendant to 1) monitor, modify and/or cancel existing appointments for the medical kiosk, 2) monitor whether a patient requires assistance, 3) monitor and/or assist a user during registration with the medical kiosk, 4) provide procedures and/or check lists for the attendant, and/or 5) provide information on the status of the medical kiosk, said attendant application configured to provide the attendant access to one or more functions selected from the group consisting of a) displaying one or more appointment fields of a user, said appointment fields include one or more fields selected from the group consisting of time of appointment, user name, medical provider name, status of appointment and action of the attendant, b) checking-in a user, c) cancelling and/or rescheduling an appointment, d) entering notes about a visit, e) entering notes about a canceled and/or rescheduled visit, f) viewing notes from the medical provider about a user, g) printing a visit summary, h) associating an emergency clean-up with a user appointment, i) viewing appointment information, j) validating user IDs, k) validating user insurance, l) modifying an appointment, m) clean protocols for the medical kiosk, n) selecting user records, o) entering BD and/or insurance information, p) providing notice of instructions and/or policies to be given to the user, q) updating user information, r) entering payment and/or copay information and/or payments for the user's visit, s) displaying a list of sanitation protocols and/or procedures, and t) activating automatic sanitation process; said appointment application configured to provide the user access to one or more functions selected from the group consisting of 1) identify user as a new and/or returning user, 2) scheduling a new appointment, verifying a previously confirmed appointment and/or canceling an appointment, 3) welcoming a user that has already scheduled an appointment, 4) providing the user with a privacy policy associated with the use of the medical kiosk, 5) providing the user with terms of service policy associated with the use of the medical kiosk, 6) requesting information as to why the user is using the user registration system, 7) requesting the user to enter a password, phone number, pin number, name, email address, address, date or birth and/or sex to identify the user, 8) requesting the user to verify if the user is at least a certain age, 9) requesting the user to identify one or more symptoms that the user is experiencing in which the user is seeking medical assistance, 10) requesting the user to answer one or more follow-up questions after the user enters the one or more symptoms, 11) informing the user to seek an in-person visit by the medical provider after the user has identified one or more symptoms that the user is experiencing, 12) requesting the user to identify one or more known allergies of the user, 13) requesting the user to identify one or more known medical conditions of the user, 14) requesting the user to identify one or more past medical procedures that have been performed on the user, 15) requesting the user to identify one or more medications the user is taking, 16) asking the user if the user has medical insurance, 17) requesting the user to enter in the medical insurance information and/or to scan the insurance card, 18) requesting the user to make a copay based the medical insurance or to fully pay for the medical visit, 19) enabling the user to request assistance, 20) listing one or more days and/or times that the medical kiosk is available for use by the user, 21) verifying all of the required information and payment information has been made by the user by displaying information on a screen, printing out verification for the user, emailing verification to user, texting verification to the user and/or leaving a voicemail of verification for the user, 22) updating user information, 23) storing information in a user file, 24) navigating the user through the vitals capture process, 25) navigating the user through the user consultation, and 26) navigating the user through a survey; said provider application is configured to have one or more features selected from the group consisting of a) displaying appointment information, b) displaying user information, c) viewing and/or modifying visit information, d) performing a consultation with the user, and e) accessing information from one or more medical devices in the medical kiosk, said provider application configured to provide the medical provider access to one or more functions selected from the group consisting of 1) viewing appointments that have been completed by the medical provider or are in progress for a certain day, 2) viewing appointments that have been made for a future time, 3) displaying one or more types of user appointment information, said user appointment information including information selected from the group consisting of time of appointment, user names, status of appointment, user payment status, user checked-in status, vitals collection status, status of video consultation status of data entry by the medical provider regarding video consultation, and status of appointment, 4) displaying a record about a user, such record information selected from the group consisting of user name, user date of birth, user sex, user symptoms, user medical conditions, date of last visit, diagnosis, allergies, medications, prior visit record of user, and medical records of user, 5) notifying the attendant that the user requires assistance, 6) limiting access to a user's information, 7) refusing an appointment that has been created for the medical provider, 8) beginning the conference with the user once the user is ready in the medical kiosk, 9) viewing the user on the medical provider's screen, 10) ending the consultation with the user, 11) viewing the user records, including the vitals capture process that has occurred or is occurring in the medical kiosk, 12) modifying a user's record, 13) adding and/or removing medication, medical conditions, allergies and/or symptoms information in the user's record, 14) entering notes about a user, diagnoses for a user, and/or follow-up care for a user, 15) controlling access to and/or activate one or more medical devices in the medical kiosk, 16) viewing the results from the use of one or more medical devices that have been used by the user, 17) creating a visit summary for a user, 18) creating a prescription for a user, 19) providing one or more visit documents and/or other types of documents to the user, 20) contacting another medical provider on the provider screen and/or enable the other medical provider to be viewed by the user, 21) engaging a translator to facilitate communication between the user and medical provider, and 22) contacting a third party to obtain information about and/or authorization for a user using the medical kiosk; said scheduling application includes one or more functions selected from the group consisting of 1) enabling a user to select a particular medical provider, 2) making an appointment on a medical kiosk at a particular time and place, 3) enabling a user to select the medical provider or type of medical provider based on the particular need of the user, 4) locating available locations of medical kiosks, 5) enabling a user to enter information about the user, 6) checking past, current and/or future appointments of the user regarding use of the medical kiosk, 7) entering a partial or full payment for use of the medical kiosk, 8) entering medical insurance information, 9) making payment information, 10) enabling a user to request assistance, 11) enabling a user to enter consents and/or consent forms, and 12) enabling the user to receive reminders about the appointment; said patient portal application configured to provide the medical provider access to one or more functions selected from the group consisting of 1) locating an available medical kiosk, 2) scheduling an appointment with the medical kiosk, 3) pre-registering symptoms and/or reasons for visit, 4) setting and/or canceling an appointment with the medical kiosk, 5) receiving reminders and/or updates regarding appointments for the medical kiosk, 6) obtaining information about medical kiosk availability, 7) obtaining information about certain medical provider availability, 8) obtaining information about the available medical provider, 9) selecting a certain medical provider and/or medical provider in a certain field of medicine, 10) obtaining map information, address information and/or hours of operation information regarding a selected medical kiosk, 11) locating the closest kiosk and/or kiosk availability for a certain medical provider and/or medical provider in a certain field of medicine, 12) presubmitting and/or preclearing medical insurance, 13) submitting payment information, 14) receiving information on payment status, 15) receiving information on insurance coverage, 16) receiving appointment reminders and/or updates, 17) receiving prescription information, 18) submitting payment information for medical visit and/or prescription, 19) answering surveys regarding the use of the medical kiosk, and 20) receiving medication reminders; said medical adherence application is configured to assist user with regard to medications, said medical adherence application including one or more functions selected from the group consisting of 1) reminding users to take their meds, 2) automatically creating a log when the user takes their medication, 3) tracking a user's compliance to taking their medication on time, 4) providing automatic progress reports, 4) referring the user to a pharmacist to answer any questions and/or for additional consultation, 5) automatically enrolling the user in a e-script network, which network sends their prescriptions to the pharmacy of their choice, 6) assisting in improving user satisfaction regarding medication compliance, 7) accessible on a screen in the medical kiosk, and/or on a computer screen and/or mobile device, 8) allowing a user to speak to a pharmacist, 9) allowing a user to change medication alerts 9) providing information to a user about various medical condition, 10) allowing the user to check medication order status, 11) allowing the user to refill prescriptions, 12) allowing user to transfer prescriptions to a pharmacy, 13) providing user with information about recommended dosages of medication, 14) providing information to user regarding period for taking medications, 15) providing user with information regarding frequency for taking medications, 16) providing information to user regarding information about medications, 17) providing information to user regarding generic brands available for medications, 18) allowing a user to request an appointment to speak with the medical provider, 19) allowing the user to enter compliance information regarding medication usage by user, 20) providing user with medication alerts, 21) allowing the user to change medication alerts, 22) allowing the user to select how information will be sent to user, and 23) providing the user with medication guidelines and/or medical plans; said an administrator application configured so that a medical administrator can remotely access one or more components of the medical kiosk; said administrator application including one or more functions selected from the group consisting of 1) allowing remote access to one or more medical devices in the medical kiosk, 2) allowing remote access to one or more computers in the medical kiosk, 3) allowing remote access to one or more routers in the medical kiosk, 4) allowing remote access to one or more displays on the medical kiosk, 5) allowing diagnostics to be executed from a remote location on one or more electronic components in the medical kiosk, 6) allowing the rebooting and/or reinitializing from a remote location of one or more electronic components in the medical kiosk, 7) allowing for review of the current and/or past status from a remote location of one or more electronic components in the medical kiosk, 8) allowing remote access to one or more power supplies in the medical kiosk, 9) allowing remote access to one or more servers in the medical kiosk, 10) allowing remote access to one or more harddrives in the medical kiosk, 11) allowing hardware and/or software updates to be remotely sent and/or loaded onto one or more electronic components in the medical kiosk, and 12) allowing software to be loaded onto and/or removed from one or more electronic components in the medical kiosk; said provider portal application configured to provide the medical provider access to one or more functions selected from the group consisting of 1) accessing another medical provider, 2) enabling two or more medical providers to be simultaneously viewed and/or heard by the user in the medical kiosk, 3) enabling the medical provider to switch to a new medical provider such that only the new medical provider is not viewed by the user in the medical kiosk, and 4) allowing a second medical provider to listen and/or communicate with the user in the medical kiosk.

14. The method as defined in claim 13, said plurality of medical devices including two or more devices selected from the group consisting of a stethoscope, an otoscope, a thermometer, a dermascope, a spirometer, blood pressure cuff, a pulse oximeter, a heating pad, a magnifying glass, a tongue depressor, tweezers, a blood glucometer, an audiometer, and a 3-lead EKG.

15. The method as defined in claim 14, wherein at least one said remotely controlled medical compartments is unlockable as the user progresses through a vitals capture program, and including the further step of causing said at least one remotely controlled medical compartment to unlock as the user progresses through a certain portion of the vitals capture program.

16. The method as defined in claim 13, wherein said medical kiosk includes a floor scale.

17. The method as defined in claim 13, wherein said medical kiosk includes a headphone jack.

18. The method as defined in claim 13, including a mobile device application or network application, said mobile application or network application configured to provide the user access to various functions on a mobile device or computer, said functions in including one or more functions selected from the group consisting of 1) locating an available medical kiosk, 2) scheduling an appointment with the medical kiosk, 3) pre-registering symptoms for visit, 4) setting an appointment with the medical kiosk, 5) receiving reminders regarding appointments for the medical kiosk, 6) obtaining information about medical kiosk availability, 7) obtaining information about certain medical provider availability, 8) obtaining information about available medical providers, 9) selecting a certain medical provider, 10) obtaining map information regarding a selected medical kiosk, 11) locating the closest kiosk for an appointment with a certain medical provider in a certain field of medicine, 12) presubmitting medical insurance, 13) submitting payment information, 14) receiving information on payment status, 15) receiving information on insurance coverage, 16) receiving updates regarding appointment regarding appointments for the medical kiosk, 17) receiving prescription information, 18) submitting payment information for prescriptions, 19) answering surveys regarding the use of the medical kiosk, 20) receiving medication reminders, 21) pre-registering reasons for visit, 22) canceling an appointment with the medical kiosk, 23) selecting a certain medical provider in a certain field of medicine, 24) providing address information regarding a selected medical kiosk, 25) obtaining hours of operation information regarding a selected medical kiosk, 26) locating the closest kiosk for an appointment with a certain medical provider, 27) locating the closest kiosk availability for an appointment with a certain medical provider in a certain field of medicine, 28)

locating the closest kiosk availability for an appointment with a certain medical provider, and 29) preclearing medical insurance.

19. The method as defined in claim 13, wherein said medical kiosk includes an exterior registration station located external to said internal enclosure, said registration station including a user input system that enables the user to enter information about the user prior to having said real-time or near real-time tele-conference with the medical provider, said user input system including one or more components selected from the group consisting of a key pad for identification, a key pad for data entry, key board for identification, a key board for data entry, a touch screen for identification, a touch screen for data entry, a microphone and voice recognition software for identification, a microphone and voice recognition software for data entry, a fingerprint scanner for identification a fingerprint scanner for data entry, a retina scanner for identification, a retina scanner for data entry, camera, speaker, card reader, smart device reader/scanner, motion sensor, sound sensor, and temperature sensor, said registration station configured to provide the user access to one or more functions selected from the group consisting of a) entering the user's name, b) entering the user's address, c) entering the user's contact information, d) entering the user's age, e) entering the user's sex, f) entering the user's height, g) entering the user's weight, h) entering the user's race, i) entering the user's language, j) entering the user's medical history, k) entering medicines used by user, l) entering information on past medical condition, m) entering reason(s) for visit by the user, n) entering user's current symptoms, o) entering user's allergies, p) entering user's ID information, q) entering user's insurance information, r) entering user's payment information, s) entering consent information, t) requesting assistance from a medical attendant, u) entering date the user desires an appointment, v) entering user's current medical provider, w) requesting a specific medical provider x) providing information to the user about the medical kiosk, y) providing information to the user on how to use the medial kiosk, z) providing information to the user on how to properly input/convey information to the medical kiosk, aa) providing the user information during the inputting/conveying of information by the user to the medical kiosk, bb) providing the user information on the wait time for the user's use of the medical kiosk, cc) providing the user with a number of other users waiting to use the medical kiosk, dd) providing the user with information regarding whether the medical kiosk is in use or is available, ee) entering time the user desires an appointment, and ff) requesting a medical provider having a particular medical specialty.

20. The method as defined in claim 13, wherein said medical kiosk includes a includes a display screen located external to said internal enclosure that can be used to provide one or more types of information selected from the group consisting of advertising information, information about the medical kiosk, information about wait time for the medical kiosk, information as to the order of users waiting to use the medical kiosk, information about whether a medical kiosk is available or in use, cable TV shows, satellite TV shows, local broadcast TV shows, infomercials, medical programs, DVD materials, Blu-ray materials, video programs, YouTube programs, and pictures, said display configured to only display information and to not accept data entry from the user.

21. The method as defined in claim 13, wherein said internal enclosure of said medical kiosk includes a cleaning or sanitizing system to clean or sanitize at least a portion of said internal enclosure, said cleaning or sanitizing system including a system selected from the group consisting of a UV system and a mist system.

22. The method as defined in claim 13, wherein said medical kiosk includes a moveable interior panel to allow access to one or more components located behind the moveable panel located in said internal enclosure, said one or more components including components selected from the group consisting of 1) electronics located behind the exterior check-in station, 2) electronics located behind the first and second video screens and 3) electronics used for network communication.

* * * * *